United States Patent
Chen et al.

(10) Patent No.: US 10,195,200 B2
(45) Date of Patent: Feb. 5, 2019

(54) COVALENT INHIBITORS OF CDK-7

(71) Applicant: Newave Pharmaceutical Inc., Pleasanton, CA (US)

(72) Inventors: Yi Chen, Pleasanton, CA (US); Yan Lou, Pleasonton, CA (US)

(73) Assignee: Newave Pharmaceutical Inc., Pleasanton, CA (US)

(*) Notice: Subject to any disclaimer, the term of this patent is extended or adjusted under 35 U.S.C. 154(b) by 0 days.

(21) Appl. No.: 15/706,980

(22) Filed: Sep. 18, 2017

(65) Prior Publication Data
US 2018/0008604 A1 Jan. 11, 2018

Related U.S. Application Data

(63) Continuation of application No. PCT/US2016/021722, filed on Mar. 10, 2016.

(60) Provisional application No. 62/135,147, filed on Mar. 18, 2015.

(51) Int. Cl.

| | | |
|---|---|---|
| A61K 31/506 | (2006.01) | |
| A61K 31/165 | (2006.01) | |
| A61K 31/397 | (2006.01) | |
| A61K 31/4015 | (2006.01) | |
| A61K 31/45 | (2006.01) | |
| A61K 31/497 | (2006.01) | |
| C07D 498/08 | (2006.01) | |
| C07D 491/06 | (2006.01) | |
| C07D 325/00 | (2006.01) | |

(52) U.S. Cl.
CPC .......... *A61K 31/506* (2013.01); *A61K 31/165* (2013.01); *C07D 325/00* (2013.01); *C07D 491/06* (2013.01); *C07D 498/08* (2013.01); *A61K 31/397* (2013.01); *A61K 31/4015* (2013.01); *A61K 31/45* (2013.01); *A61K 31/497* (2013.01)

(58) Field of Classification Search
CPC ................ A61K 31/165; A61K 31/397; A61K 31/4015; A61K 31/45; A61K 31/497; A61K 31/506; C07D 325/00
See application file for complete search history.

(56) References Cited

U.S. PATENT DOCUMENTS

| 9,133,214 B2 * | 9/2015 | Blanchard ............ C07D 498/06 |
| 2004/0209895 A1 | 10/2004 | Luecking et al. |
| 2013/0172338 A1 | 7/2013 | Blanchard et al. |

FOREIGN PATENT DOCUMENTS

WO 2008060248 A1 5/2008

OTHER PUBLICATIONS

Wolff, Manfred E., Burger's Medicinal Chemistry and Drug Discovery, Fifth Ed., vol. 1: Principles and Practice, John Wiley & Sons, 1995, 975. (Year: 1995).*
Banker, Gilbert S. et al., Modern Pharmaceutics, Marcel Dekker, New York, 1996. (Year: 1996).*
West, Anthony R., Solid State Chemistry and Its Applications, Wiley, New York, 1988, 358. (Year: 1988).*

* cited by examiner

*Primary Examiner* — Erich A Leeser
(74) *Attorney, Agent, or Firm* — McCarter & English, LLP; Yu Lu; Wei Song

(57) ABSTRACT

The disclosure includes compounds of Formula (I)

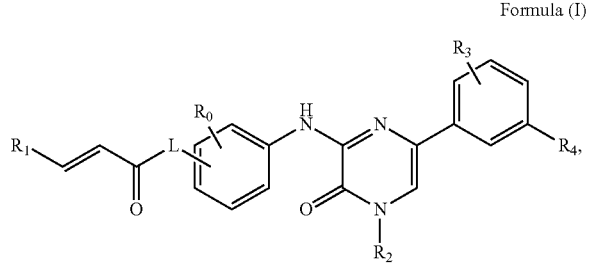

Formula (I)

wherein $R_0$, $R_1$, $R_2$, $R_3$, $R_4$, $R_5$, and L are defined herein. Also disclosed is a method for treating a neoplastic disease, autoimmune disease, and inflammatory disorder with these compounds.

18 Claims, No Drawings

COVALENT INHIBITORS OF CDK-7

REFERENCE TO RELATED APPLICATION

This application is a continuation of International Patent Application No. PCT/US2016/021722, filed on Mar. 10, 2016, which claims the benefit of the filing date, under 35 U.S.C. 119(e), of U.S. Provisional Application No. 62/135,147 filed on Mar. 18, 2015. The entire contents of each of the aforementioned applications are incorporated herein by reference.

BACKGROUND

The members of the cyclin-dependent kinase (CDK) family play critical regulatory roles in proliferation. There are currently 20 known mammalian CDKs. While CDK7-13 have been linked to transcription, only CDK1, 2, 4, and 6 show demonstrable association with the cell cycle. Unique among the mammalian CDKs, CDK7 has consolidated kinase activities, regulating both the cell cycle and transcription. In the cytosol, CDK7 exists as a heterotrimeric complex and is believed to function as a CDK1/2-activating kinase (CAK), whereby phosphorylation of conserved residues in CDK1/2 by CDK7 is required for full catalytic CDK activity and cell cycle progression (Desai et al., "Effects of phosphorylation by CAK on cyclin binding by CDC2 and CDK2," *Mol. Cell Biol.*, 15:345-350 (1995); Kaldis et al., "Analysis of CAK activities from human cells," *Eur. J. Biochem.*, 267:4213-4221 (2000); Larochelle et al., "Requirements for CDK7 in the assembly of CDK1/cyclin B and activation of CDK2 revealed by chemical genetics in human cells," *Mol. Cell*, 25:839-850 (2007)).

In the nucleus, CDK7 forms the kinase core of the RNA polymerase (RNAP) II general transcription factor complex and is charged with phosphorylating the C-terminal domain (CTD) of RNAP II, a requisite step in gene transcriptional initiation (Serizawa et al., "Association of CDK-activating kinase subunits with transcription factor TFIIH," *Nature*, 374:280-282 (1995); Shiekhattar et al., "CDK-activating kinase complex is a component of human transcription factor TFIIH," *Nature*, 374:283-287 (1995); Drapkin et al., "Human cyclin-dependent kinase-activating kinase exists in three distinct complexes," *Proc. Natl. Acad. Sci. U.S.A.*, 93:6488-6493 (1996); Liu et al., "Two cyclin-dependent kinases promote RNA polymerase II transcription and formation of the scaffold complex," *Mol. Cell Biol.*, 24:1721-1735 (2004); Akhtar et al., "TFIIH kinase places bivalent marks on the carboxy-terminal domain of RNA polymerase II," *Mol. Cell*, 34:387-393 (2009); Glover-Cutter et al., "TFIIH-associated CDK7 kinase functions in phosphorylation of C-terminal domain Ser7 residues, promoter-proximal pausing, and termination by RNA polymerase II," *Mol. Cell Biol.*, 29:5455-5464 (2009)). Together, the two functions of CDK7, i.e., CAK and CTD phosphorylation, support critical facets of cellular proliferation, cell cycling, and transcription.

Disruption of RNAP II CTD phosphorylation has been shown to preferentially effect proteins with short half-lives, including those of the anti-apoptotic BCL-2 family (Konig et al., "The novel cyclin-dependent kinase inhibitor flavopiridol downregulates Bcl-2 and induces growth arrest and apoptosis in chronic B-cell leukemia lines," *Blood*, 1:4307-4312 (1997); Gojo et al., "The cyclin-dependent kinase inhibitor flavopiridol induces apoptosis in multiple myeloma cells through transcriptional repression and down-regulation of Mcl-1," *Clin. Cancer Res.*, 8:3527-3538 (2002)). Cancer cells have demonstrated ability to circumvent pro-cell death signaling through upregulation of BCL-2 family members (Llambi et al., "Apoptosis and oncogenesis: give and take in the BCL-2 family," *Curr. Opin. Genet. Dev.*, 21:12-20 (2011)).

Inhibition of human CDK7 kinase activity is likely to result in anti-proliferative activity, and pharmacological inhibition could be used to treat proliferative disorders, including cancer. Indeed, flavopiridol, a non-selective pan-CDK inhibitor that targets CTD kinases, has demonstrated efficacy for the treatment of chronic lymphocytic leukemia (CLL), but suffers from a poor toxicity profile (Lin et al., "Phase II study of flavopiridol in relapsed chronic lymphocytic leukemia demonstrating high response rates in genetically high-risk disease," *J. Clin. Oncol.*, 27:6012-6018 (2009); Christian et al., "Flavopiridol in chronic lymphocytic leukemia: a concise review," *Clin. Lymphoma Myeloma*, 9 Suppl. 3: S179-S185 (2009)). A covalent/selective CDK7 inhibitor may hold promise as a therapeutic agent for the treatment of cancers associated with aberrant activity of CDK 7.

SUMMARY OF THE INVENTION

This invention provides compounds of the Formula (I), or an N-oxide thereof, or a pharmaceutically acceptable salt, solvate, polymorph, tautomer, stereoisomer, an isotopic form, or a prodrug of said compound of Formula (I) or N-oxide thereof:

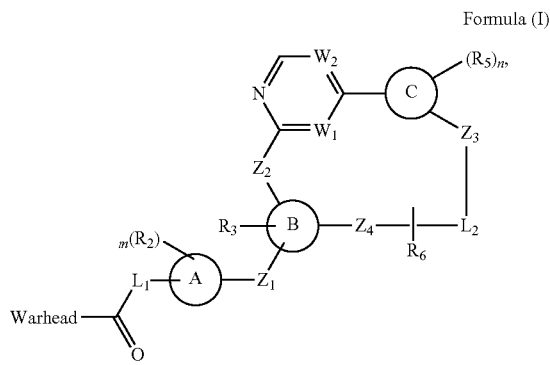

Formula (I)

wherein

A is cycloalkyl, heterocycloalkyl, cycloalkenyl, heterocycloalkenyl, aryl, heteroaryl, fused hetero-bicyclic, or spiro-heterocyclic;

each of B, and C, independently, is cycloalkyl, cycloalkenyl, heterocycloalkyl, heterocycloalkenyl, aryl, or heteroaryl;

each of $Z_1$, $Z_2$, $Z_3$, and $Z_4$ independently, is a bond, $(CR^aR^b)_p$, $(CR^aR^b)_pN(R^a)(CR^aR^b)_q$, $N(R^a)(CR^aR^b)_qN(R^a)$, $(CR^aR^b)_pO(CR^aR^b)_q$, $(CR^aR^b)_pC\!\!=\!\!C(CR^aR^b)_q$, $(CR^aR^b)_pC\!\!\equiv\!\!C(CR^aR^b)_q$, $C(R^a)\!\!=\!\!N$, O, S, C(O), $N(R^a)$, $S(O_2)$, OC(O), C(O)O, $OSO_2$, $S(O_2)O$, C(O)S, SC(O), C(O)C(O), $C(O)N(R^a)$, $N(R^a)C(O)$, $S(O_2)N(R^a)$, $N(R^a)S(O_2)$, OC(O)O, OC(O)S, $OC(O)N(R^a)$, $OC(O)N(R^a)(CR^aR^b)_{p+1}N(R^a)(CR^aR^b)_q$, $N(R^a)C(O)O$, $N(R^a)C(O)S$, $N(R^a)C(O)N(R^b)$, $(CR^aR^b)_pN(R^a)C(O)(CR^aR^b)_q$, or $(CR^aR^b)_pC(O)N(R^a)(CR^aR^b)_q$;

each of m, n, p, and q independently, is 0, 1, 2, 3, or 4;
Warhead is

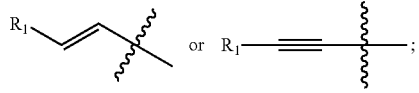

$L_1$ is $N(R_7)$ if the atom which $L_1$ connects to ring A is a carbon atom; or $L_1$ is a direct bond if ring A is a heterocycloalkyl, heterocycloalkenyl, or heteroaryl and the atom which $L_1$ connects to ring A is a nitrogen atom;

$L_2$ is $(CR^aR^b)_sC=C(CR^aR^b)_r$ in which each of r, and s independently, is 1, 2, 3, or 4;

each of $W_1$, and $W_2$ independently, is $C(R_4)$ or N;

each of $R_1$, $R_2$, $R_3$, $R_4$, $R_5$, $R_6$, and $R_7$, independently, is H, alkyl, alkenyl, alkynyl, cycloalkyl, cycloalkenyl, heterocycloalkyl, heterocycloalkenyl, aryl, heteroaryl, halo, nitro, oxo, cyano, —$OR_a$, —$SR_a$, —$NR_bR_c$, —$C(O)R_a$, —$S(O)R_a$, —$SO_2R_a$, —$P(O)R_bR_c$, —$C(O)N(R_b)R_c$, —$N(R_b)C(O)R_c$, —$C(O)OR_a$, —$OC(O)R_a$, —$SO_2N(R_b)R_c$, —$N(R_b)SO_2R_c$, -alkyl-$R_a$, -alkyl-$C(O)R_a$, -alkyl-$NR_bR_c$, -alkyl-$C(O)N(R_b)R_c$, -alkyl-$N(R_b)R_cC(O)$, or -alkyl-$N(R_b)SO_2R_c$; and each of $R^a$, $R^b$, $R_a$, $R_b$, and $R_c$, independently, is H, alkyl, alkenyl, alkynyl, cycloalkyl, cycloalkenyl, heterocycloalkyl, heterocycloalkenyl, aryl, heteroaryl, halo, cyano, amine, nitro, hydroxy, —C(O)NHOH, alkoxy, alkoxyalkyl, haloalkyl, hydroxyalkyl, aminoalkyl, alkylcarbonyl, alkoxycarbonyl, alkylcarbonylamino, dialkylamino, or alkylamino.

In preferred embodiments, the compound is represented by Formula (II)

Formula (II)

[Formula II structure]

in which each of $Z_1$, $Z_2$, $Z_3$, and $Z_4$ independently, is a bond, $(CH_2)_p$, $(CH_2)_pNR_a(CH_2)_q$, $NR_a(CH_2)_qNR_a$, $(CH_2)_pO(CH_2)_q$, CH=N, O, S, C(O), NH, $S(O_2)$, OC(O), C(O)O, $OSO_2$, $S(O_2)O$, C(O)S, SC(O), C(O)C(O), C(O)NH, NHC(O), $S(O_2)NH$, $NHS(O_2)$, OC(O)O, OC(O)S, OC(O)NH, $OC(O)NH(CH_2)_{p+1}NH(CH_2)_q$, NHC(O)O, NHC(O)S, NHC(O)NH, $(CH_2)_pNHC(O)(CH_2)_q$, or $(CH_2)_pC(O)NH(CH_2)_q$; $R_1$ is H, alkyl, or alkyl-$NR_bR_c$; and each of $R_2$, $R_3$, $R_4$, $R_5$, $R_6$, and $R_7$, independently, is H, alkyl, alkenyl, alkynyl, cycloalkyl, cycloalkenyl, heterocycloalkyl, heterocycloalkenyl, halo, nitro, oxo, cyano, —$OR_a$, —$SR_a$, —$NR_bR_c$, —$C(O)R_a$, —$SO_2R_a$, —$C(O)NHR_c$, —$NHC(O)R_c$, —$SO_2NHR_c$, —$NHSO_2R_c$, -alkyl-$R_a$, -alkyl-$C(O)R_a$, -alkyl-$NHR_c$, -alkyl-$C(O)NHR_c$, -alkyl-NHC(O), or -alkyl-$NHSO_2R_c$.

In more preferred embodiments, the compound is represented by Formula (III)

Formula (III)

[Formula III structure]

in which t, is 0, 1, 2, 3 or 4; $R_1$ is H, low alkyl, or low alkyl-$NR_bR_c$; each of $R_3$, $R_4$, and $R_5$, independently, is H, alkyl, alkenyl, alkynyl, halo, or haloalkyl; and M is $(CH_2)_p$, O, or $N(R_a)$.

In more preferred embodiments, the compound is represented by Formula (IV)

Formula (IV)

[Formula IV structure]

In more preferred embodiments, $R_1$ is H, $CH_3$, or $CH_2$—$N(CH_3)CH_3$; $R_4$ is H, $CH_3$, $CF_3$, CN, or halo.

In any of the preceding embodiments, A may be

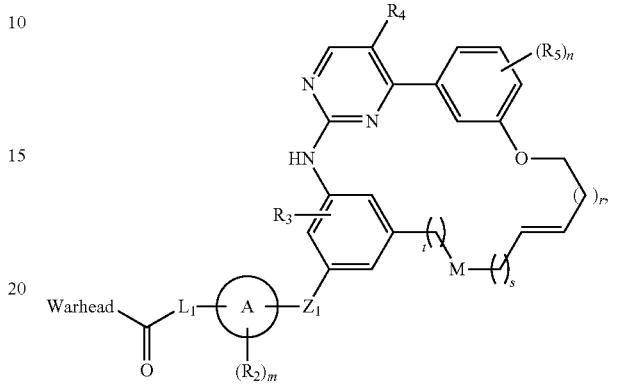

-continued
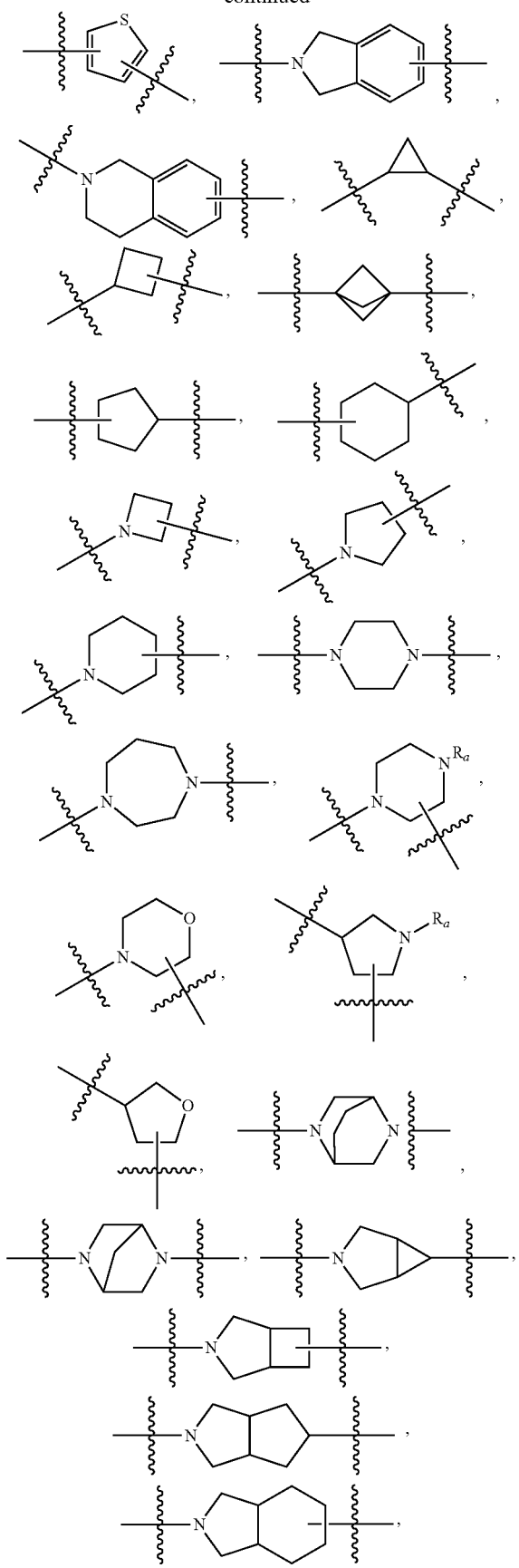
-continued
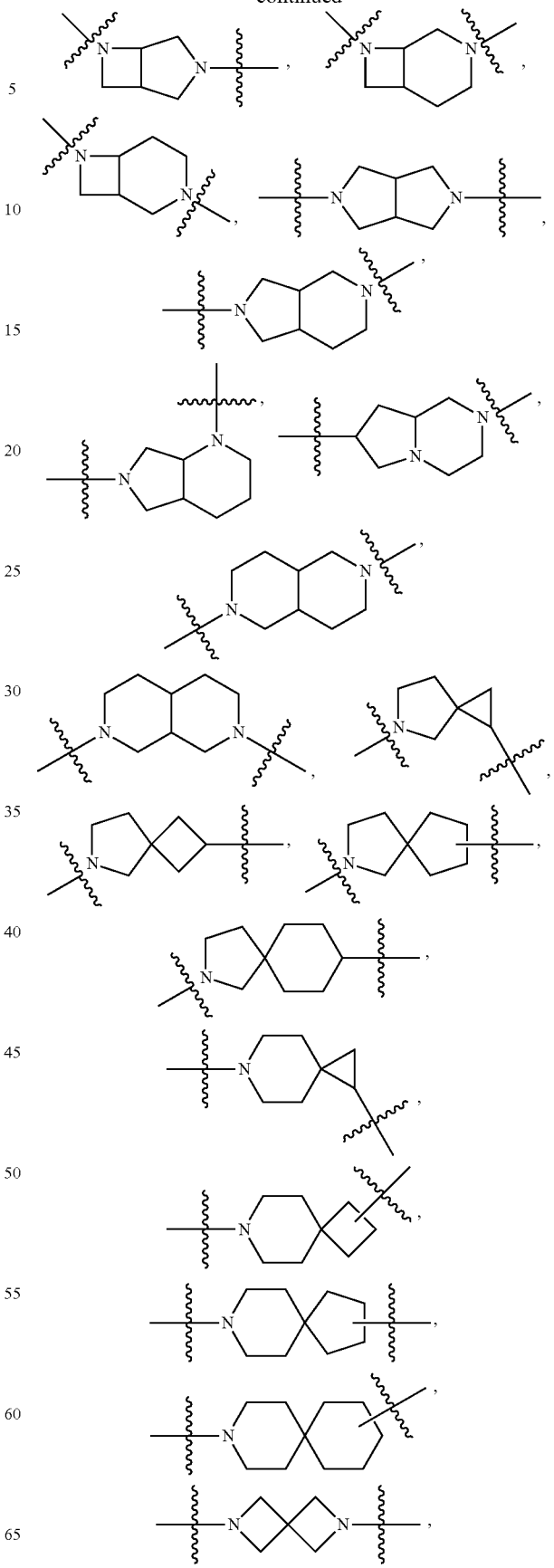

-continued

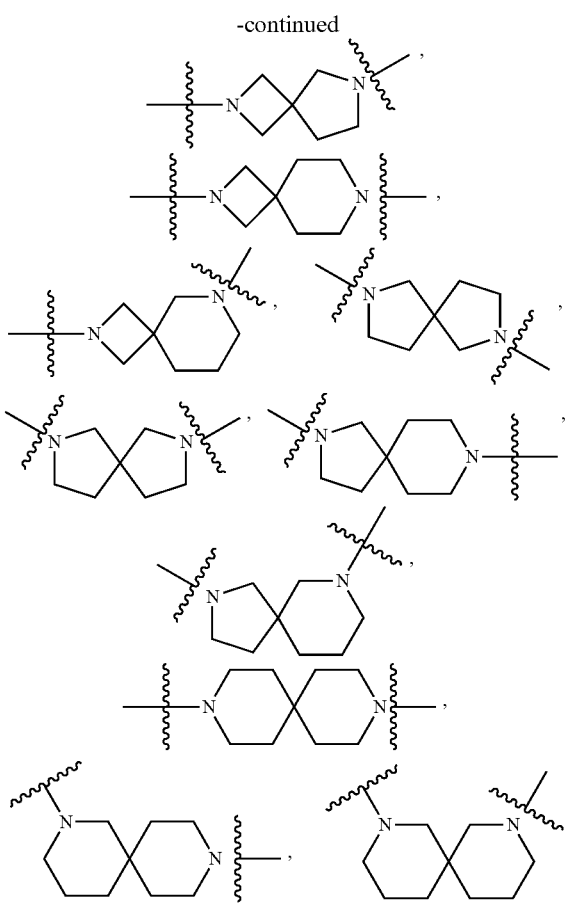

or, in which $L_1$ and $Z_1$ can be linked to A via either left

or right

Compounds of the invention may contain one or more asymmetric carbon atoms. Accordingly, the compounds may exist as diastereomers, enantiomers, or mixtures thereof. Each of the asymmetric carbon atoms may be in the R or S configuration, and both of these configurations are within the scope of the invention.

A modified compound of any one of such compounds including a modification having an improved (e.g., enhanced, greater) pharmaceutical solubility, stability, bioavailability, and/or therapeutic index as compared to the unmodified compound is also contemplated. Exemplary modifications include (but are not limited to) applicable prodrug derivatives, and deuterium-enriched compounds.

It should be recognized that the compounds of the present invention may be present and optionally administered in the form of salts or solvates. The invention encompasses any pharmaceutically acceptable salts and solvates of any one of the above-described compounds and modifications thereof.

Also within the scope of this invention is a pharmaceutical composition containing one or more of the compounds, modifications, and/or salts and thereof described above for use in treating a neoplastic disease, therapeutic uses thereof, and use of the compounds for the manufacture of a medicament for treating the disease/disorder.

This invention also relates to a method of treating a neoplastic disease, including but not limited to lung cancer, head and neck cancer, central nervous system cancer, prostate cancer, testicular cancer, colorectal cancer, pancreatic cancer, liver cancer, stomach cancer, biliary tract cancer, esophageal cancer, gastrointestinal stromal tumor, breast cancer, cervical cancer, ovarian cancer, uterine cancer, leukemia, lymphomas, multiple myeloma, melanoma, basal cell carcinoma, squamous cell carcinoma, bladder cancer, renal cancer, sarcoma, mesothelioma, thymoma, myelodysplastic syndrome, or myeloproliferative disease, by administering to a subject in need thereof an effective amount of one or more of the compounds, modifications, and/or salts, and compositions thereof described above.

The details of one or more embodiments of the invention are set forth in the description below. Other features, objects, and advantages of the invention will be apparent from the description and from the claims. It should be understood that all embodiments/features of the invention (compounds, pharmaceutical compositions, methods of make/use, etc.) described herein, including any specific features described in the examples and original claims, can combine with one another unless not applicable or explicitly disclaimed.

DETAILED DESCRIPTION OF THE INVENTION

Exemplary compounds described herein include, but are not limited to, the following:

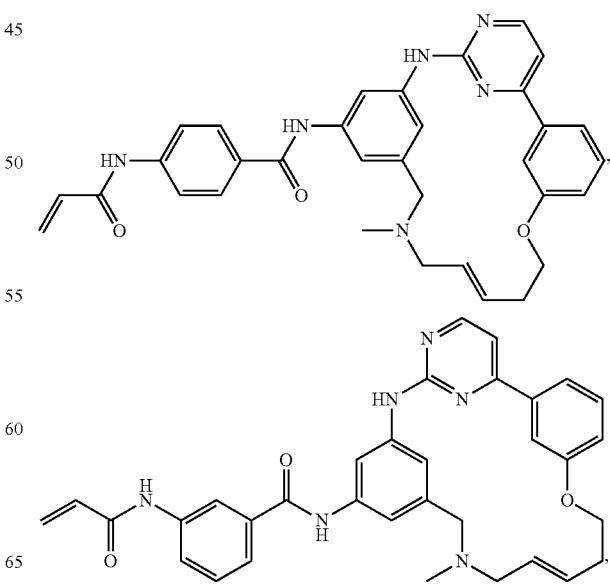

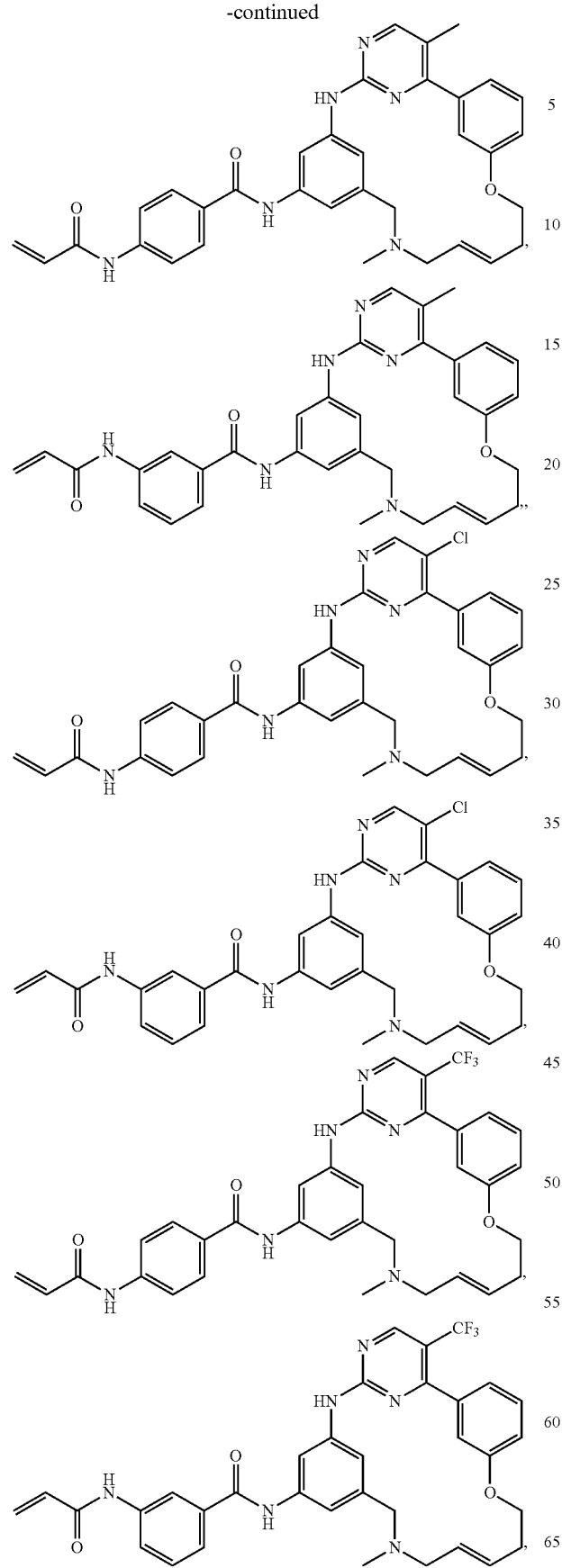
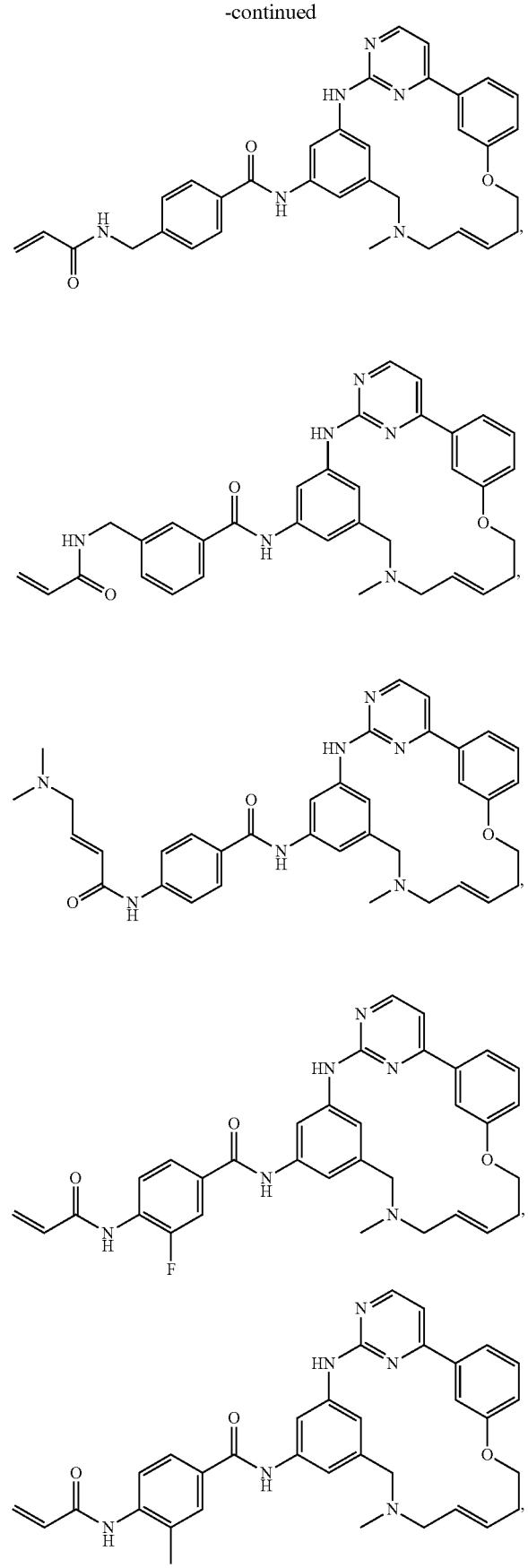

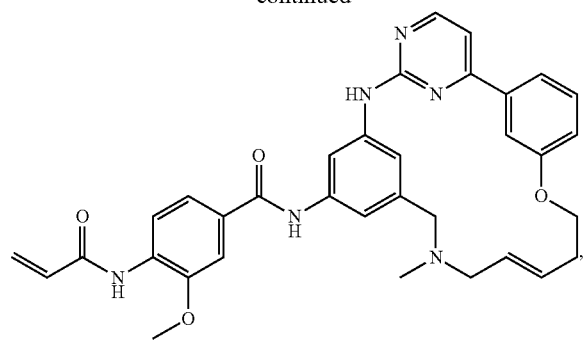
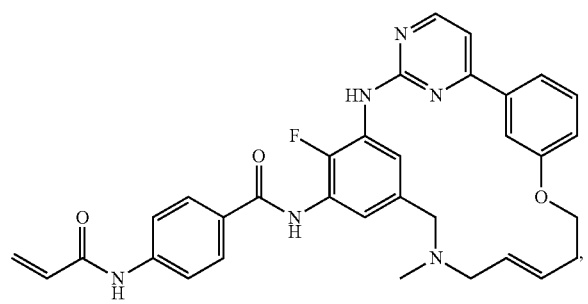
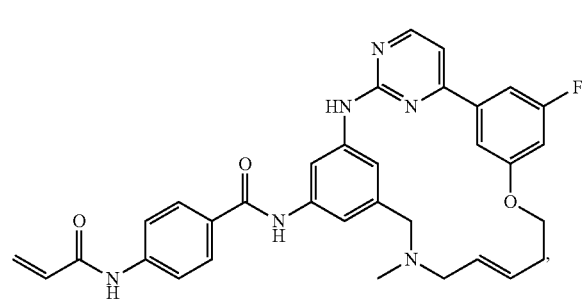
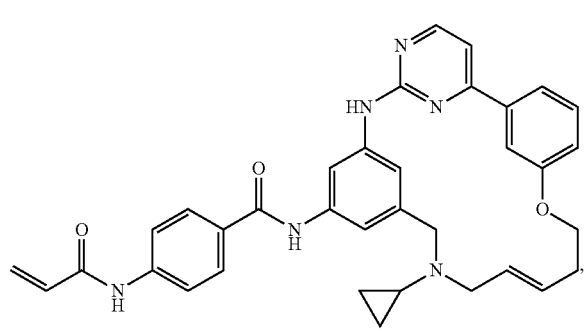
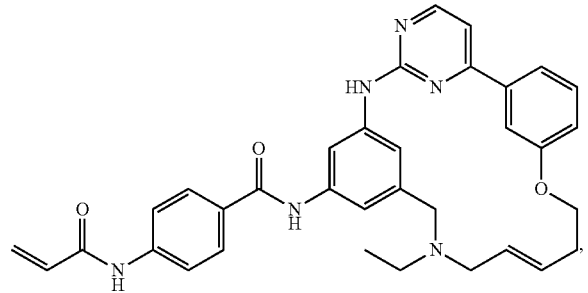
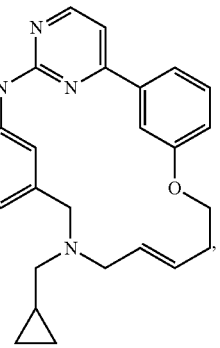
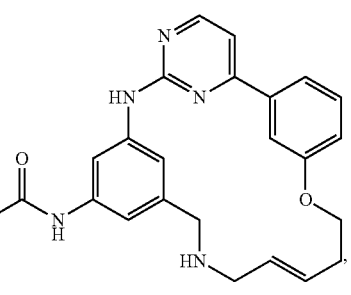
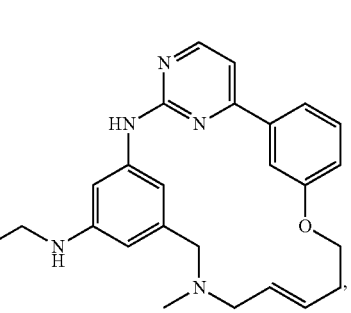
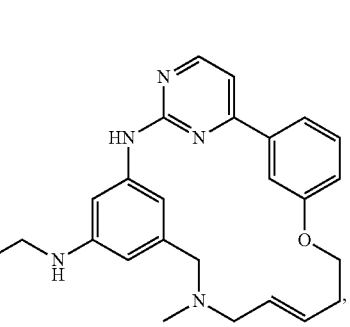
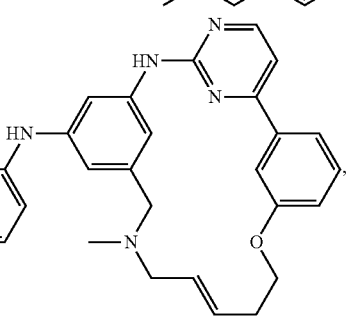

13
-continued
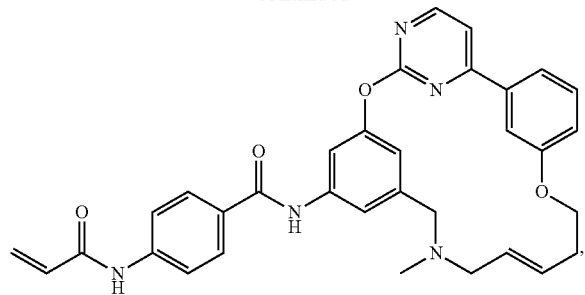
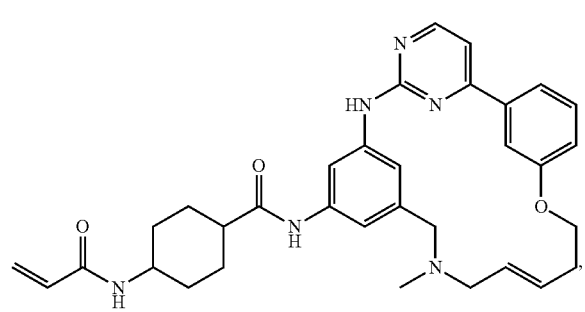
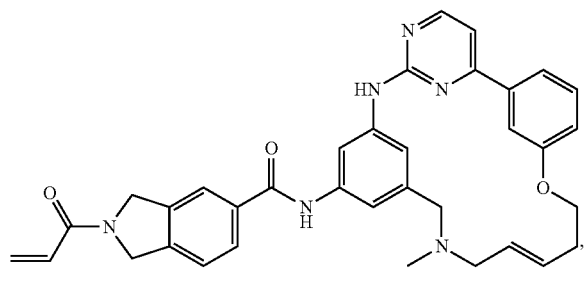
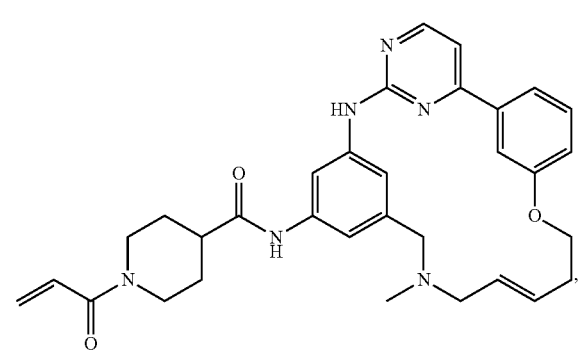
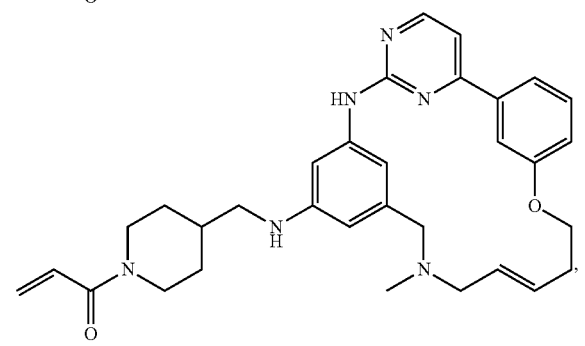
14
-continued
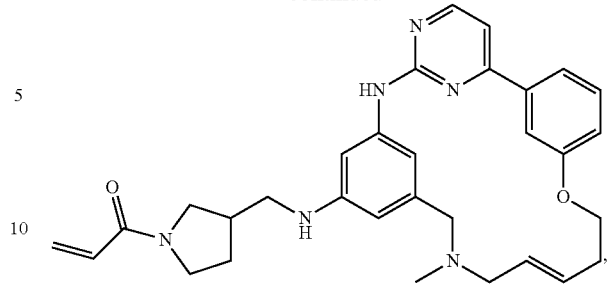
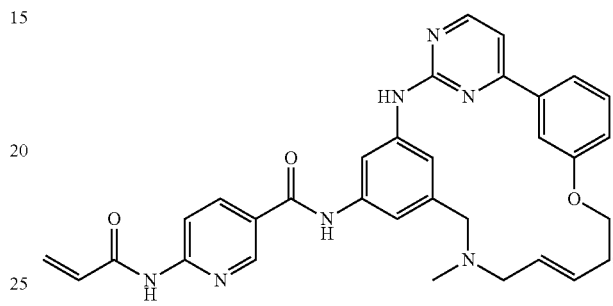
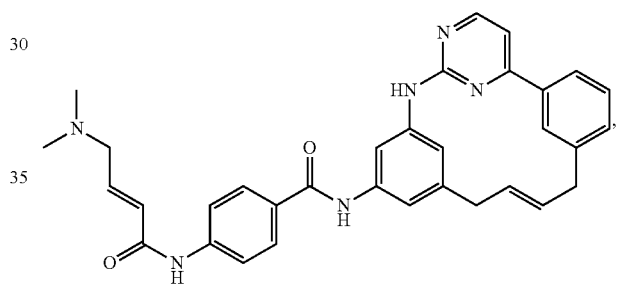
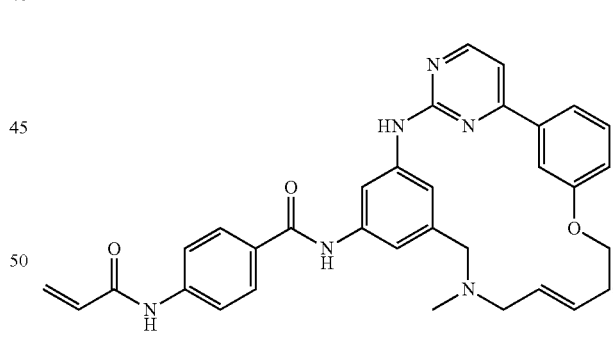
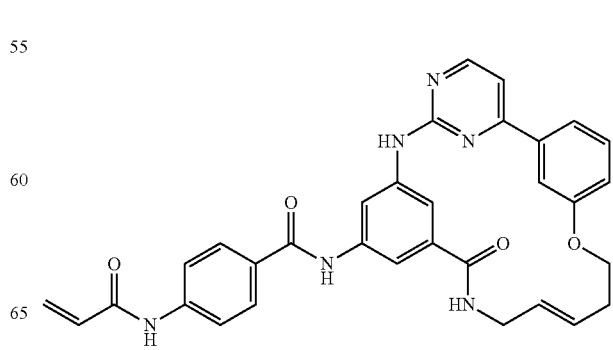

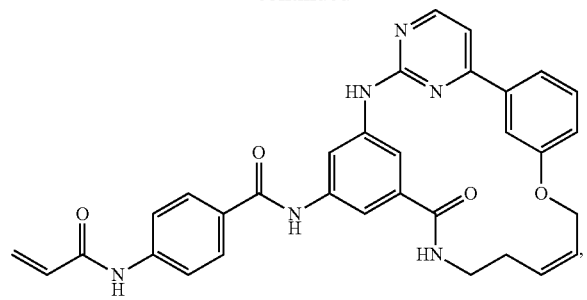
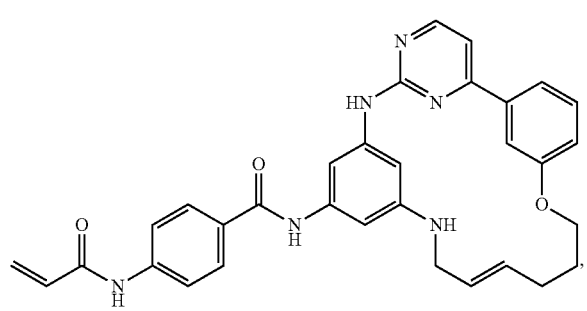
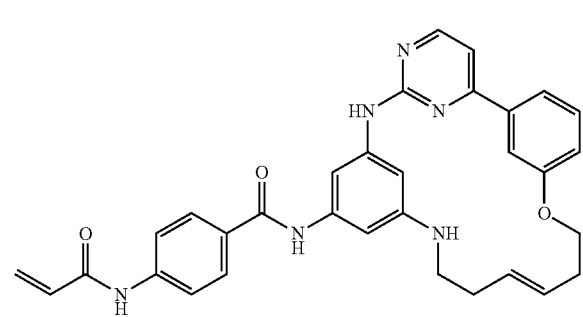
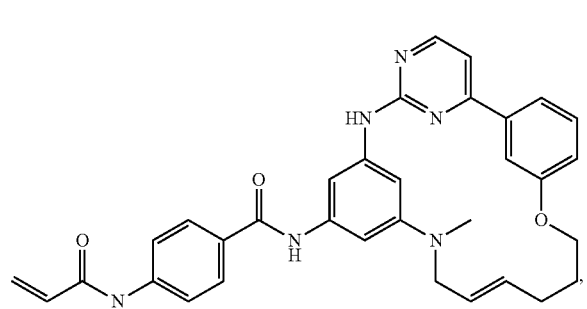
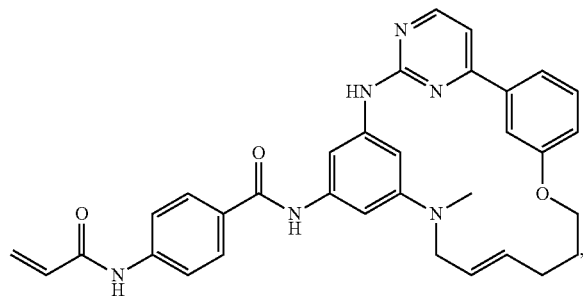
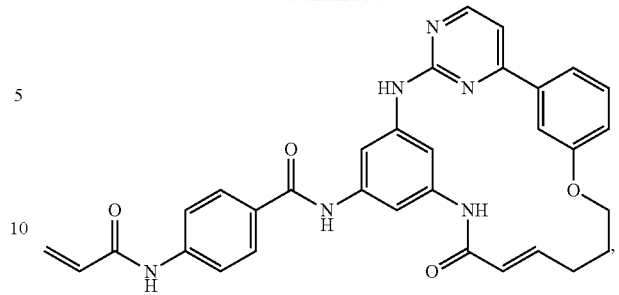
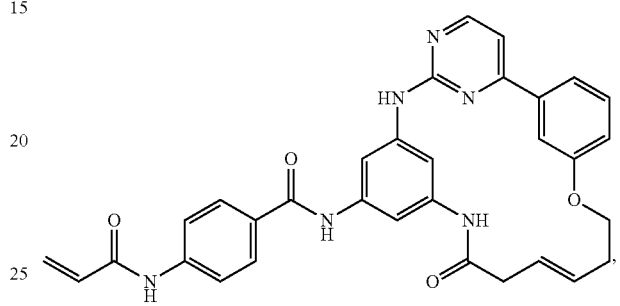
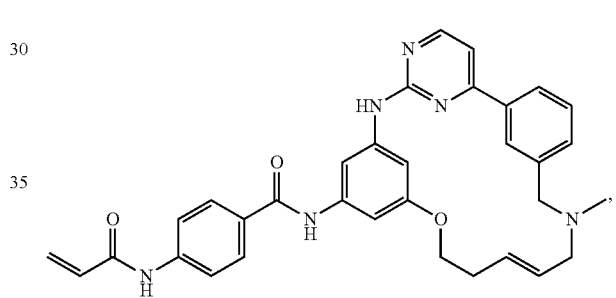
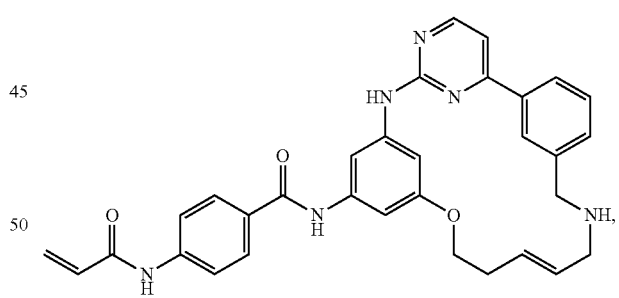
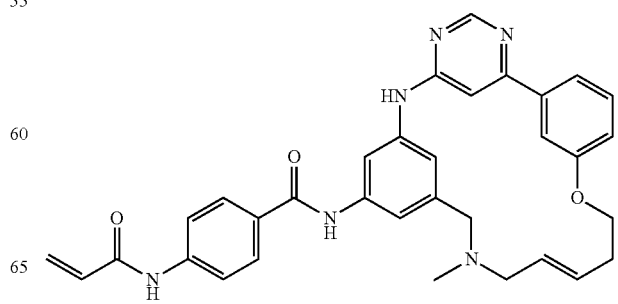

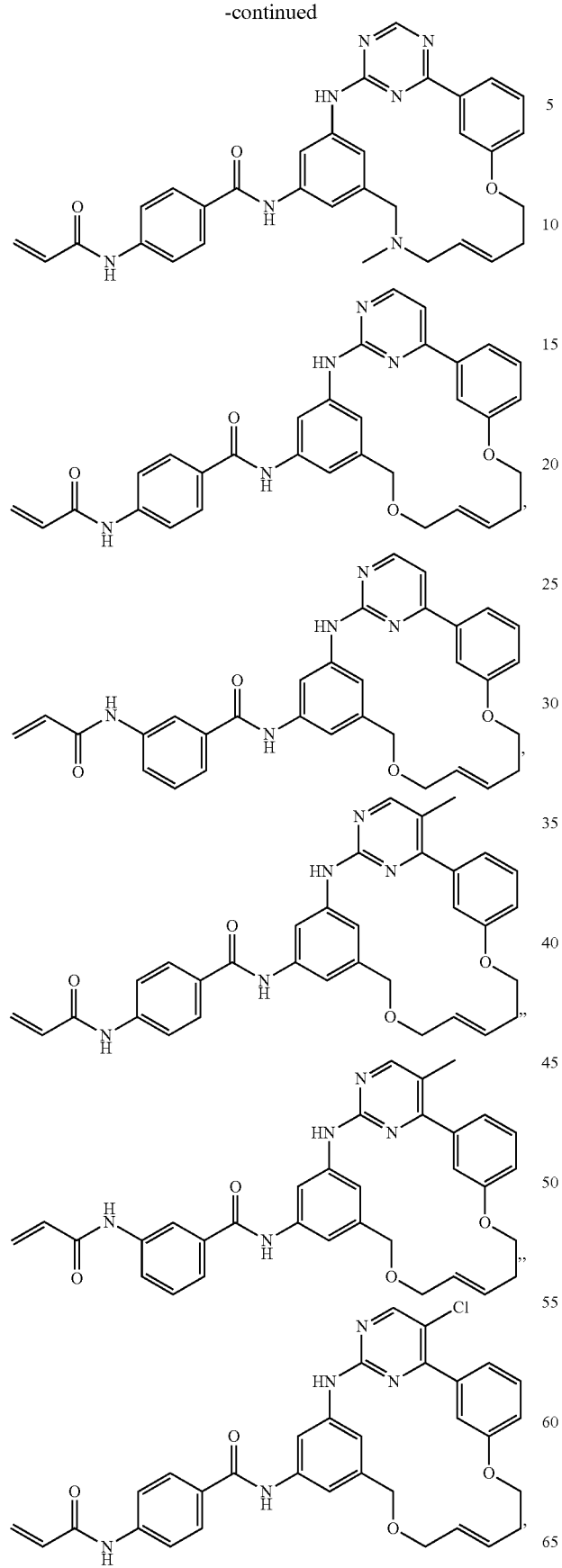
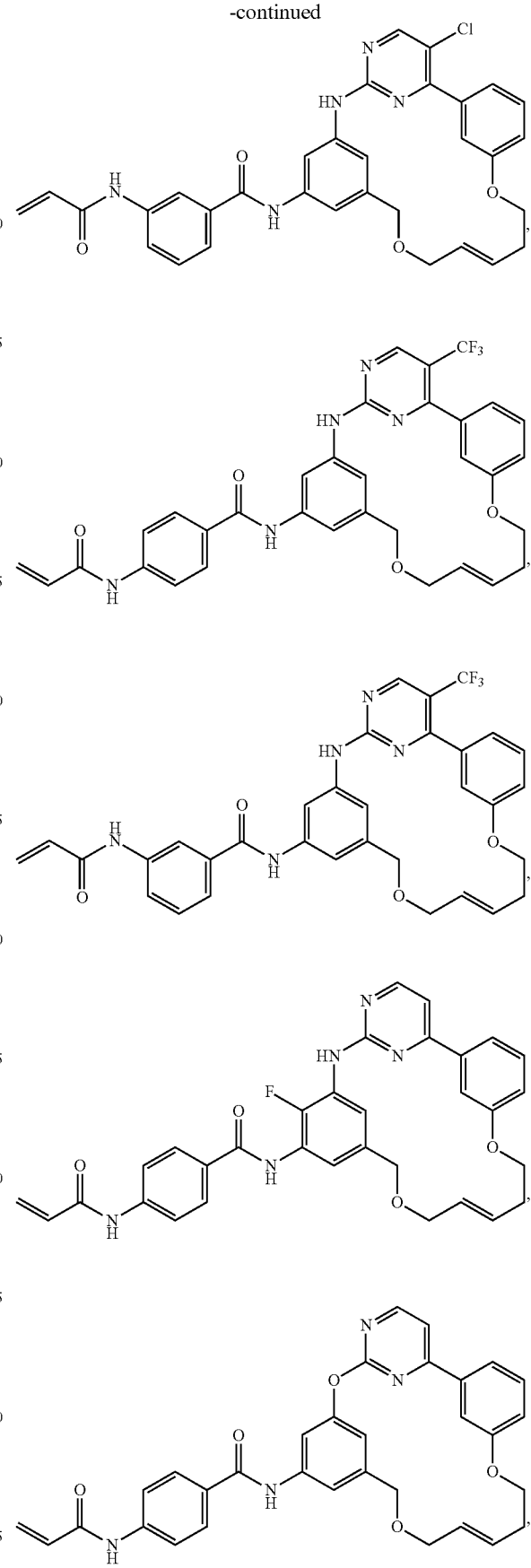

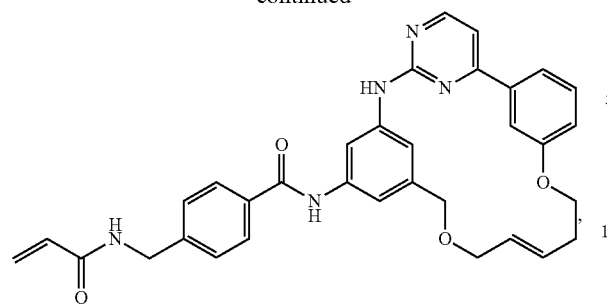
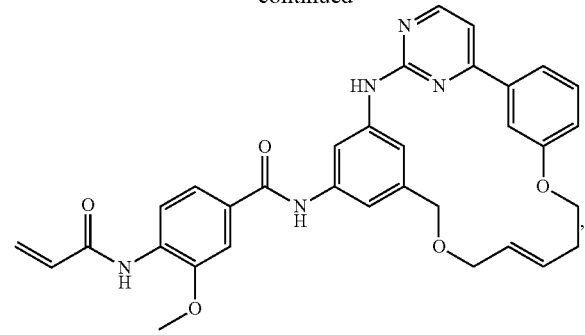
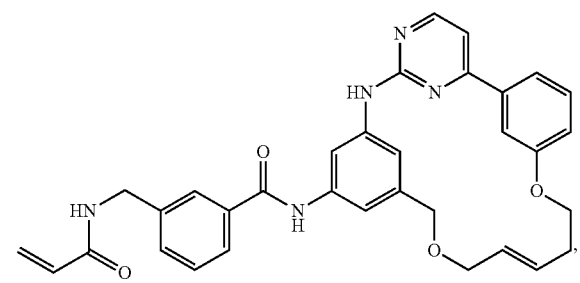
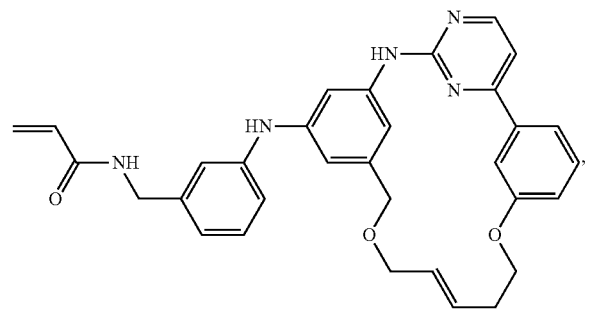
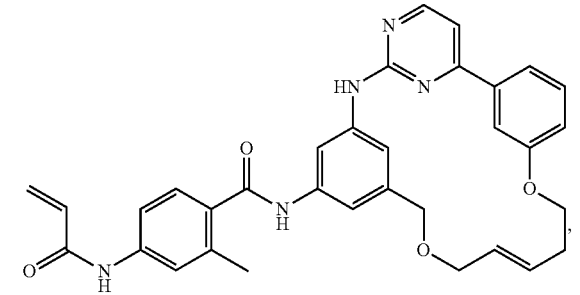
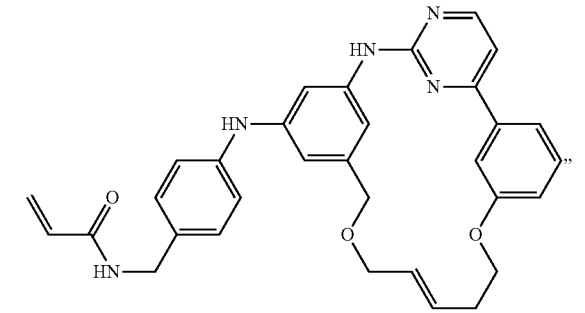
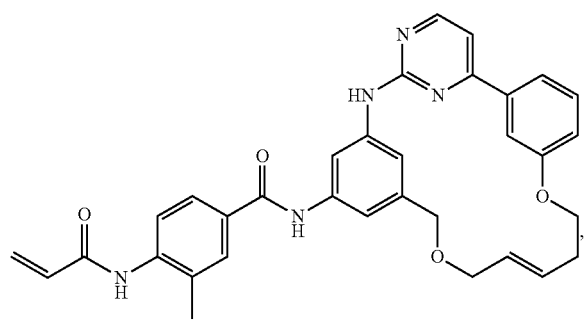
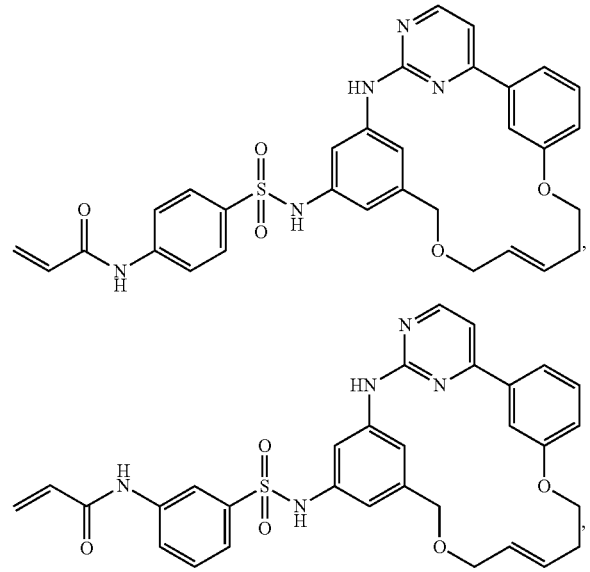

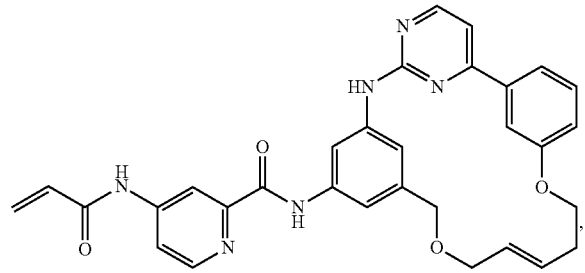
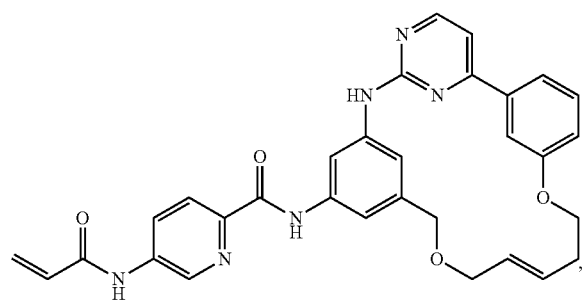
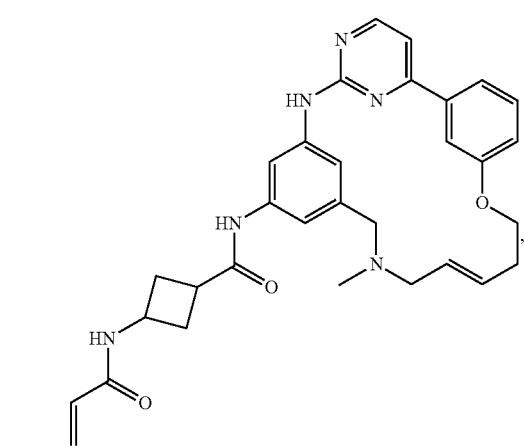
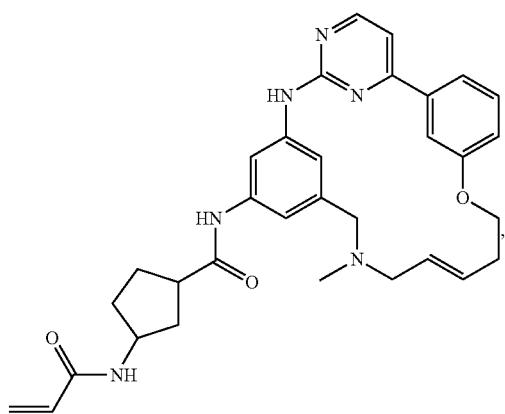
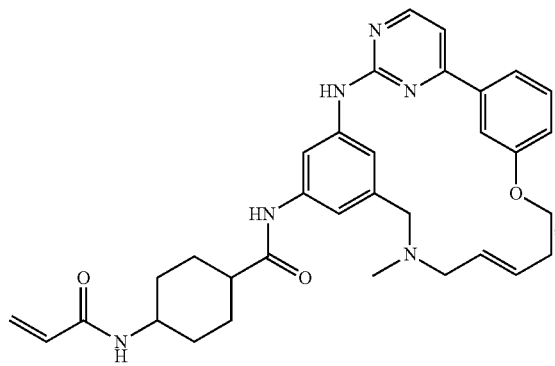
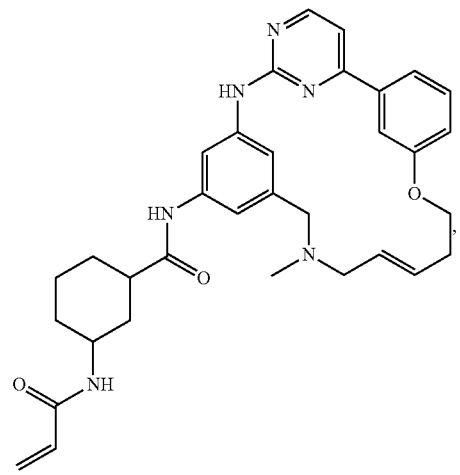
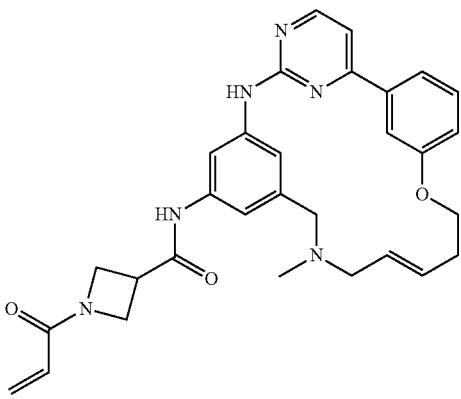
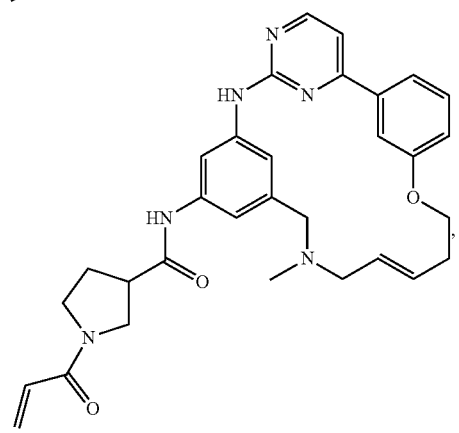

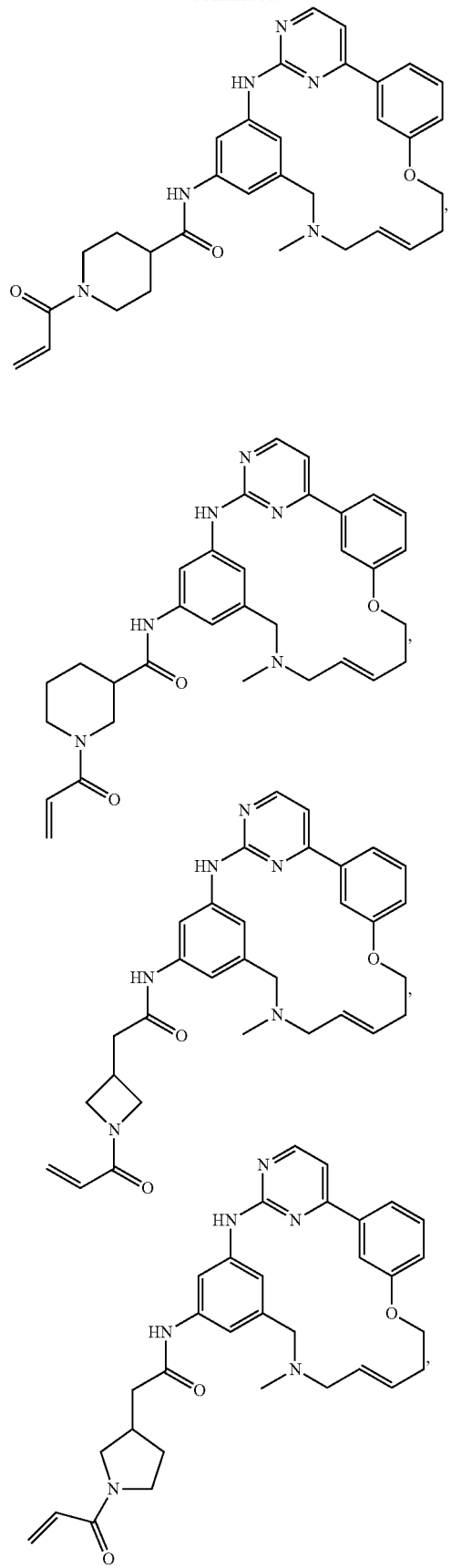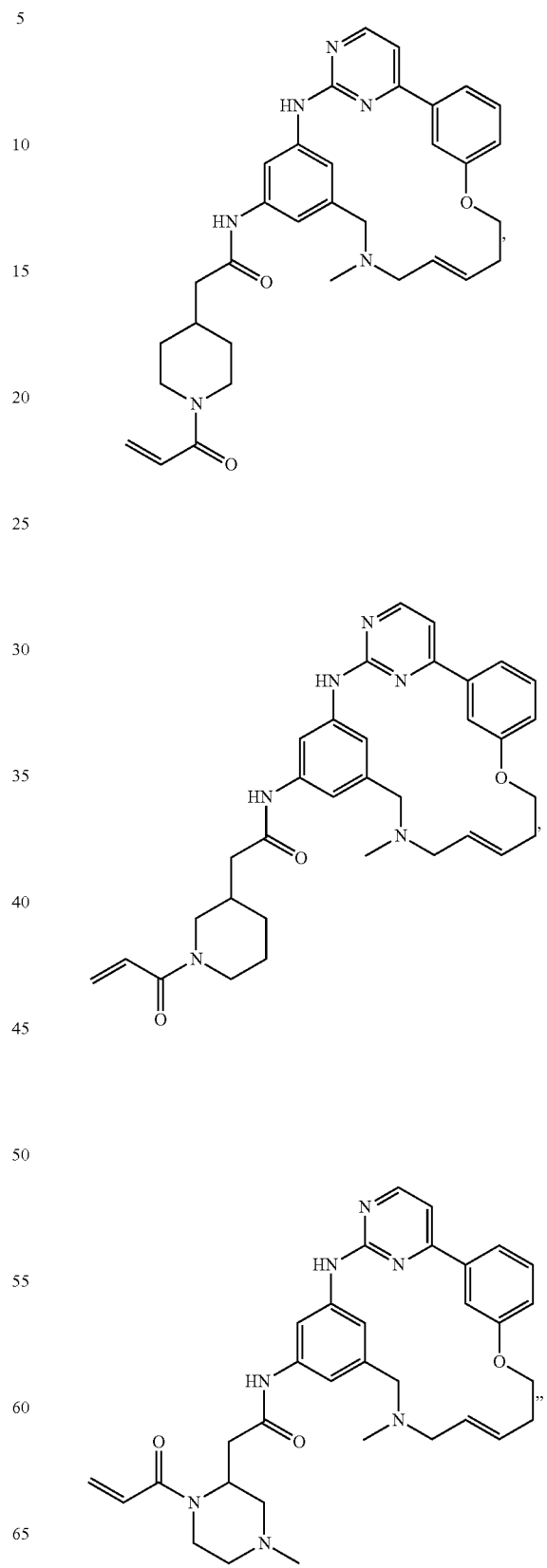

25
-continued
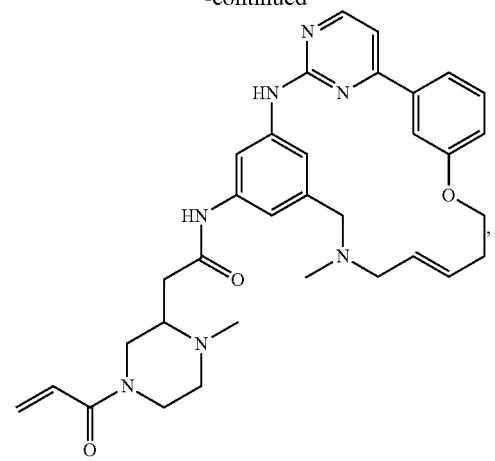
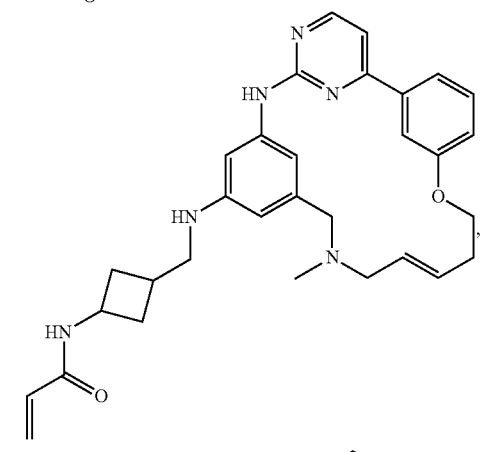
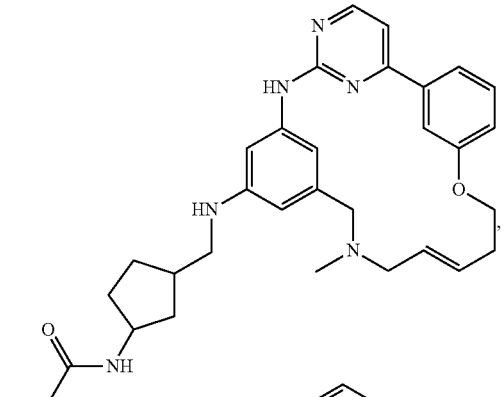
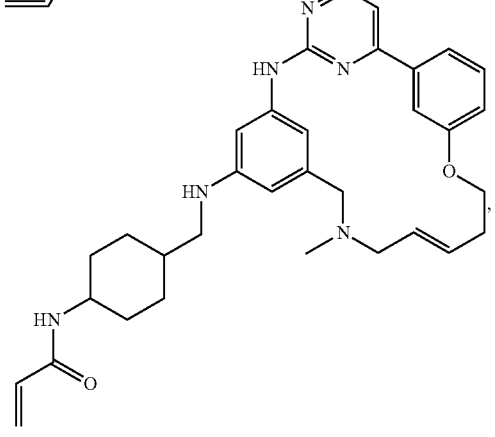
26
-continued
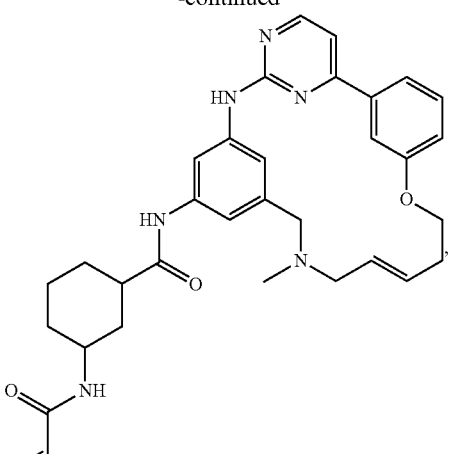
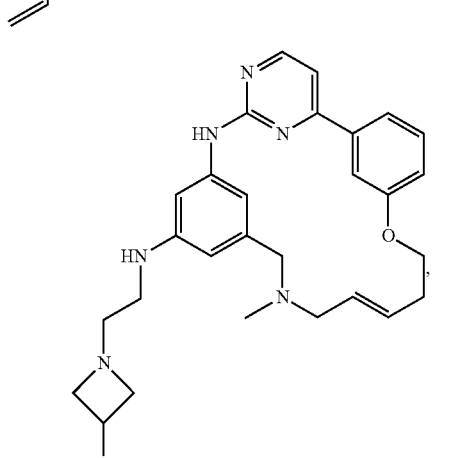
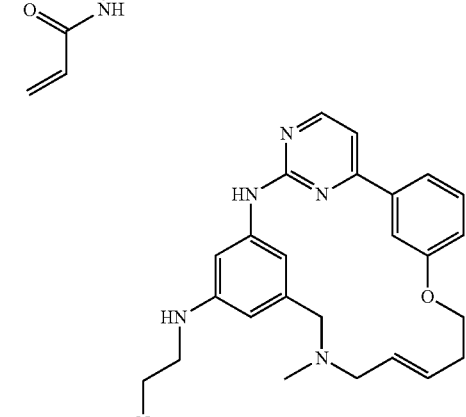

-continued
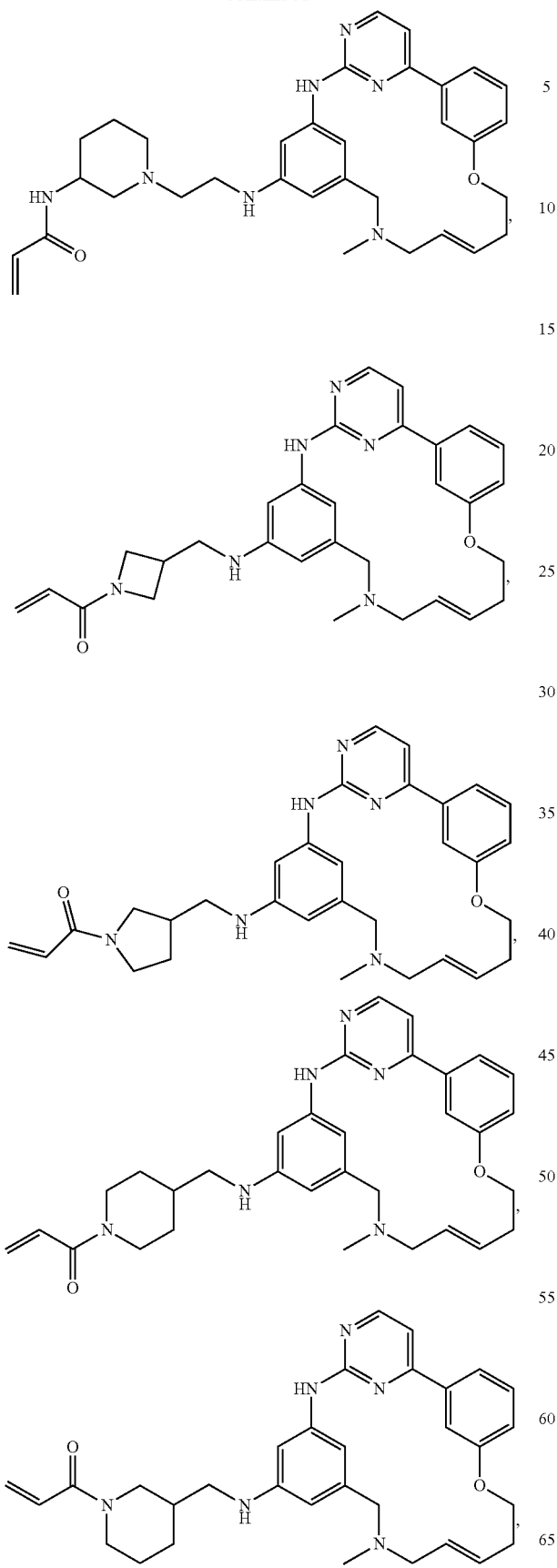
-continued
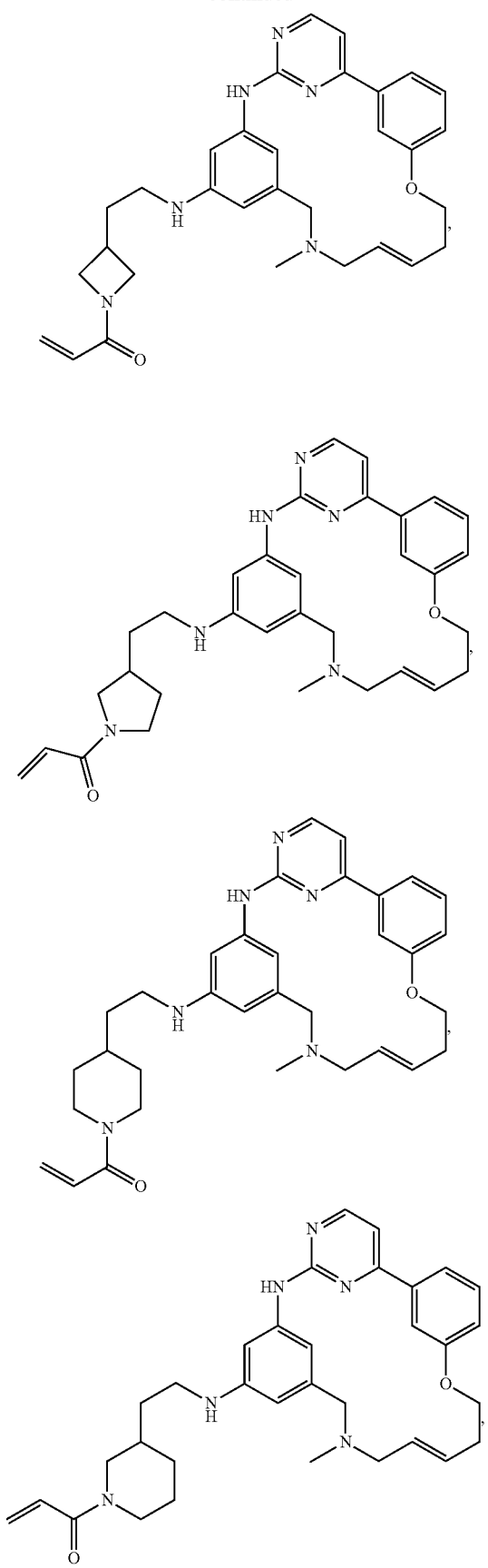

29
-continued
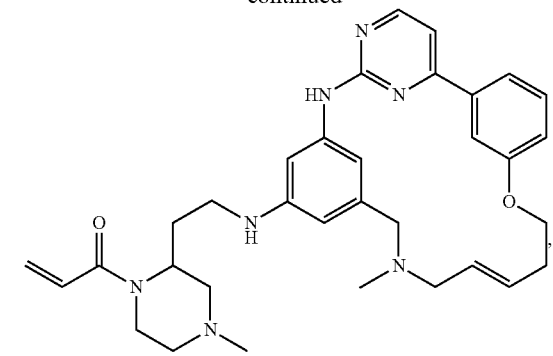
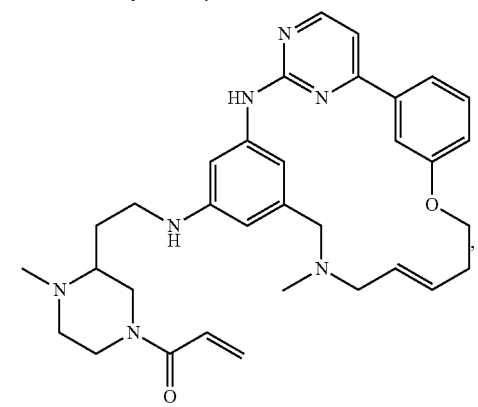
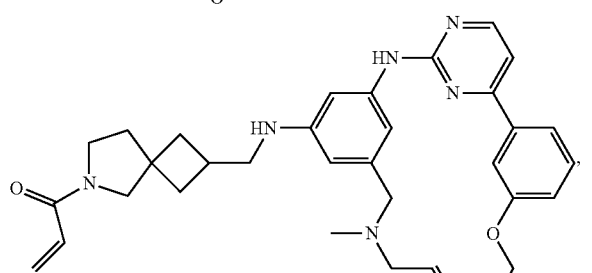
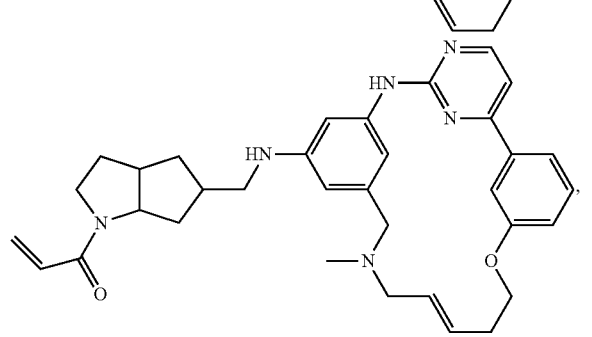
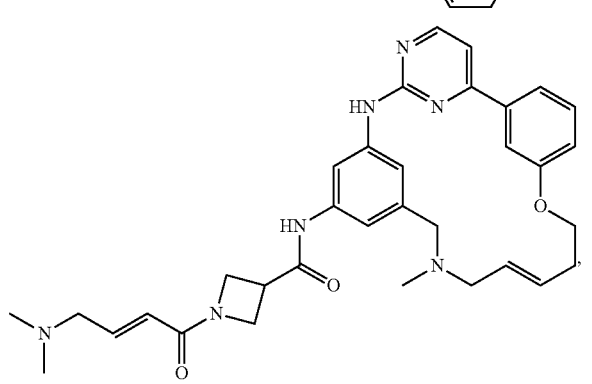
30
-continued
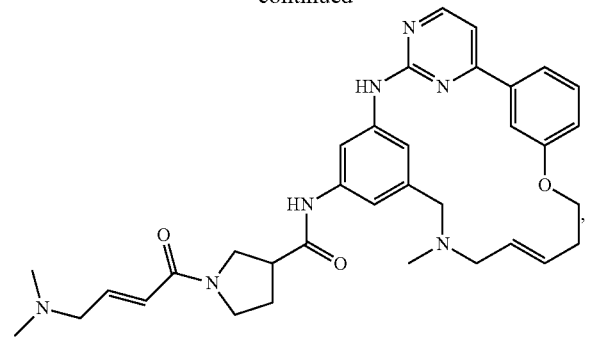
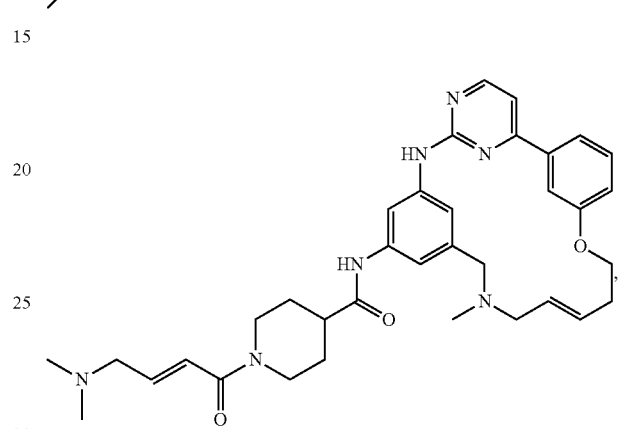
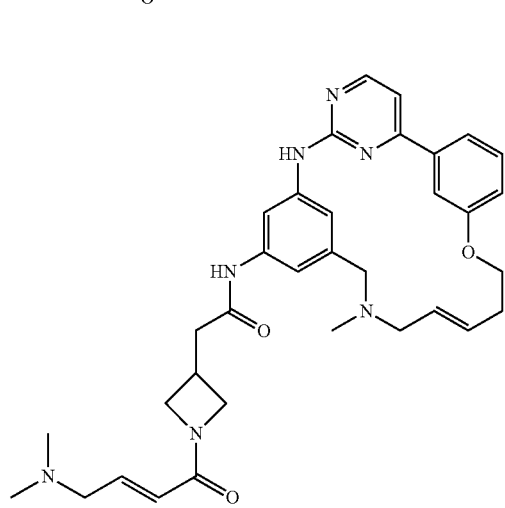
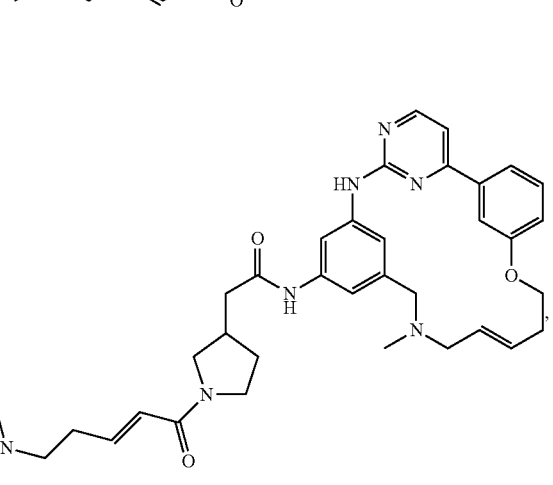

31
-continued
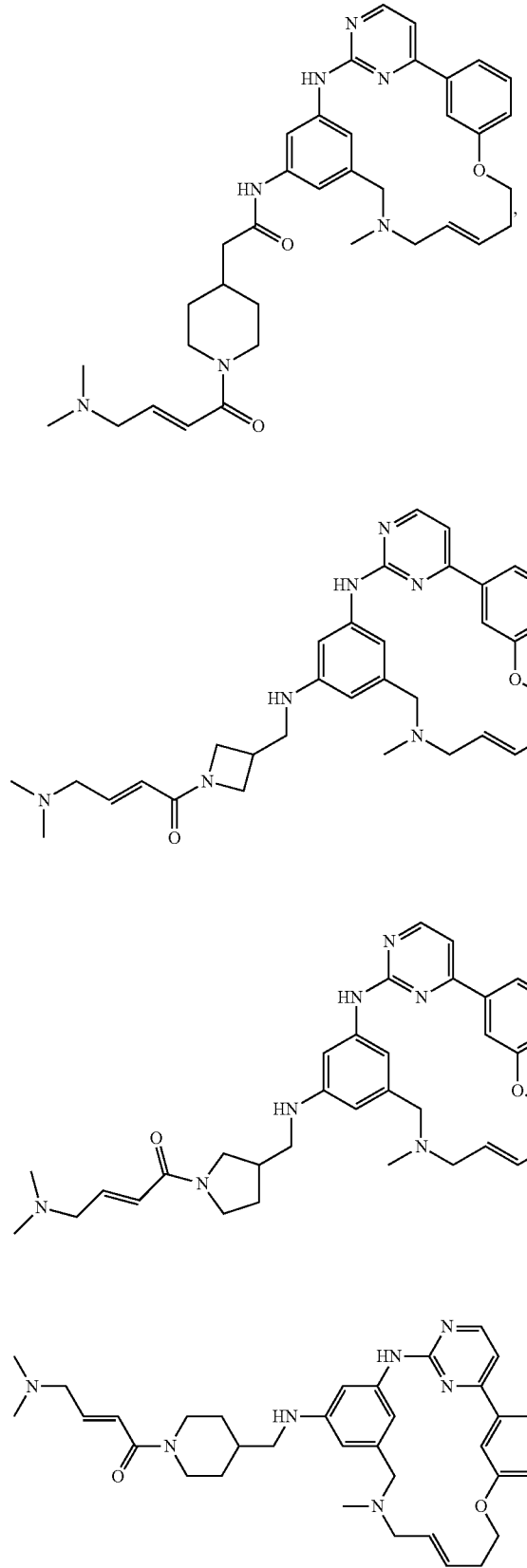
32
-continued
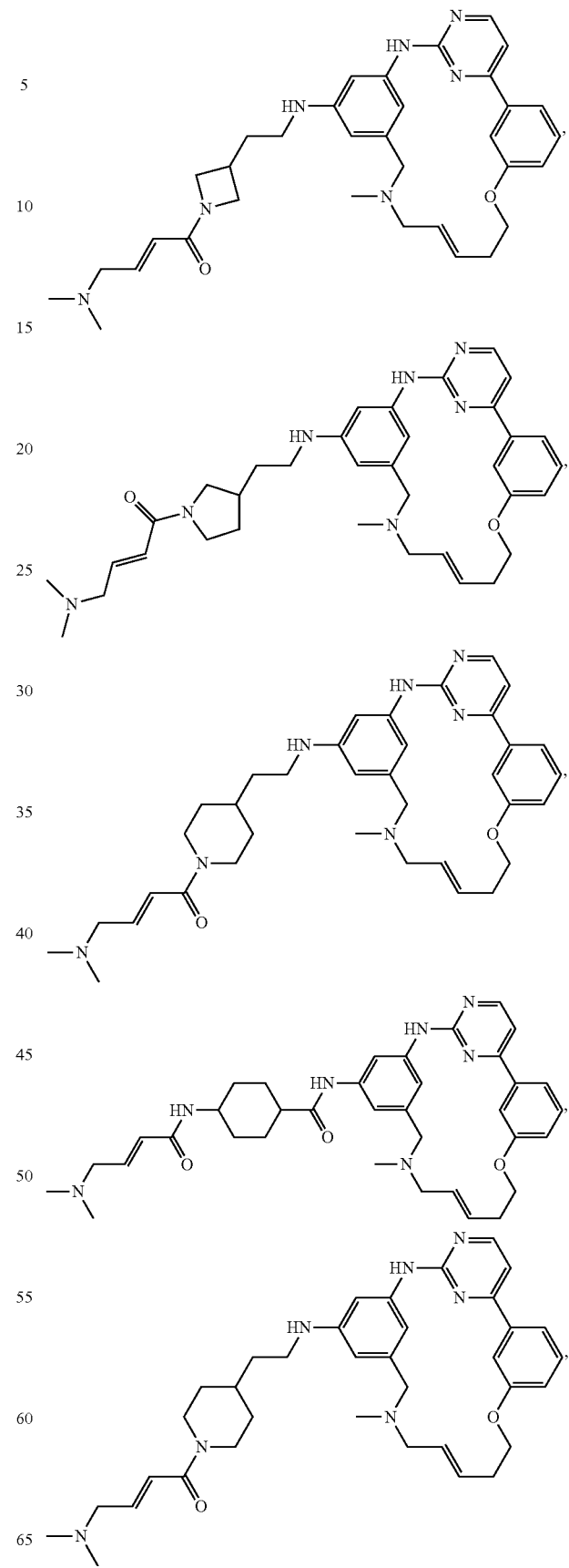

33
-continued
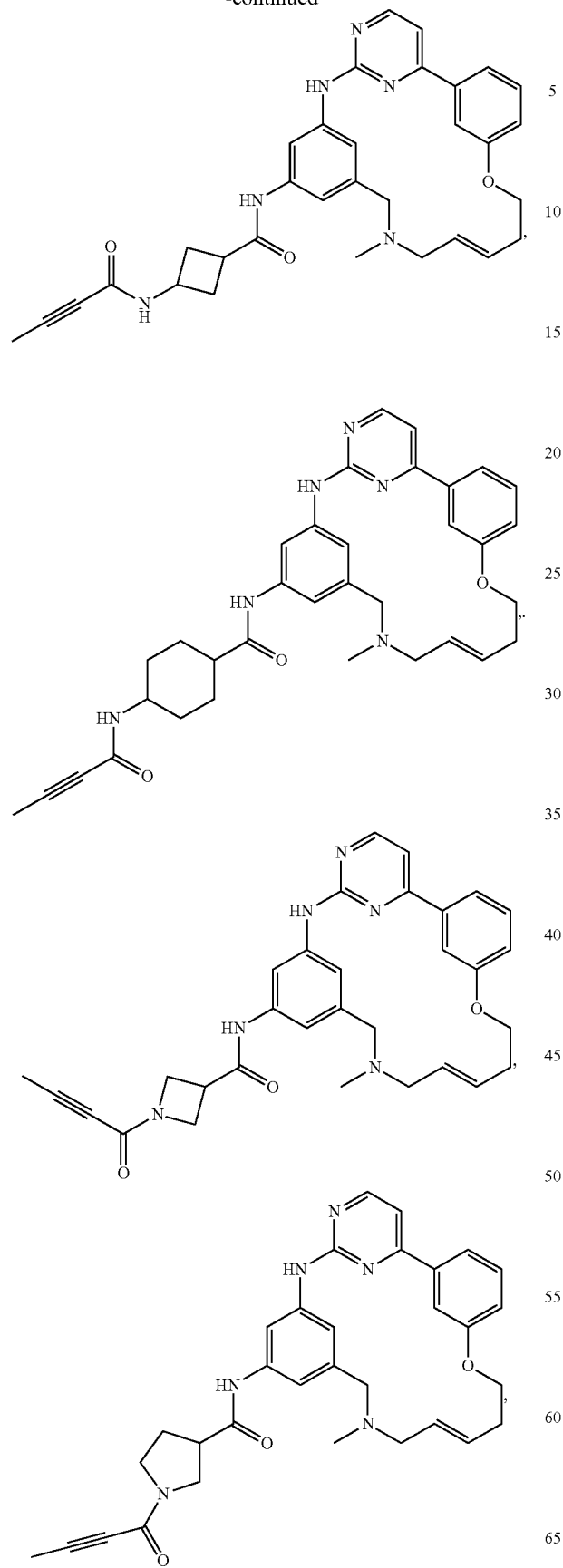
34
-continued
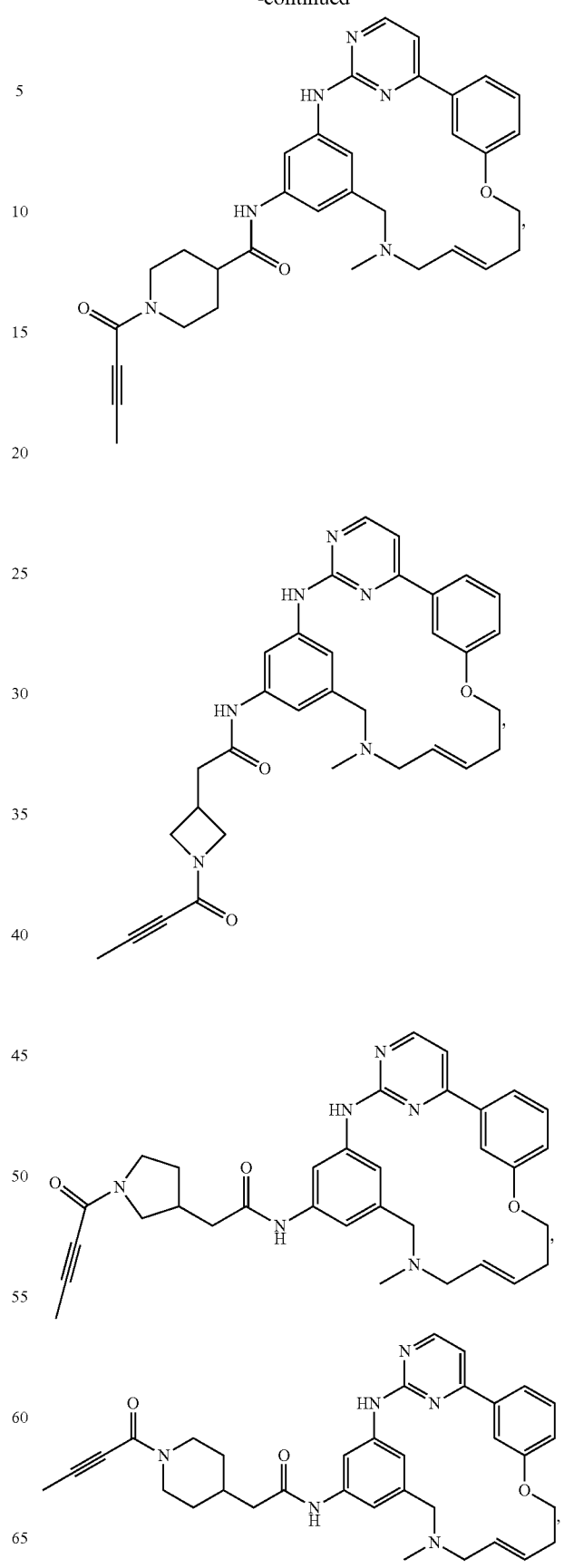

35
-continued
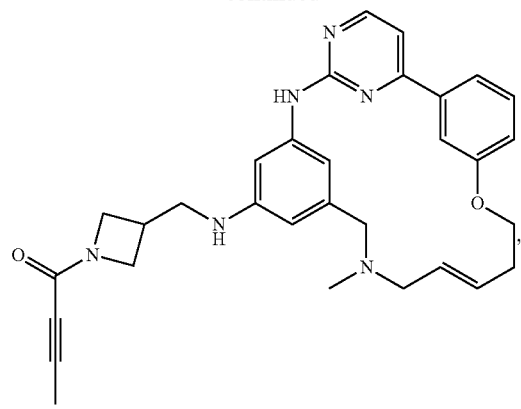
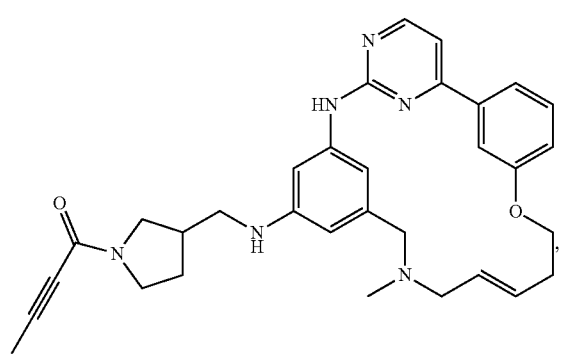
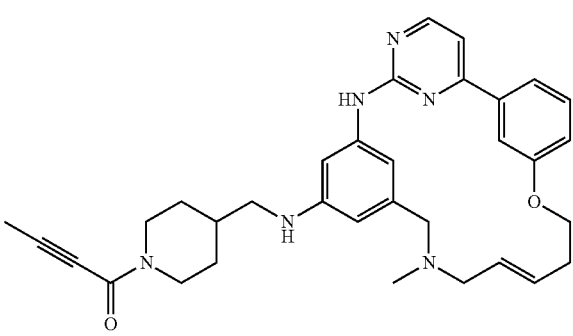
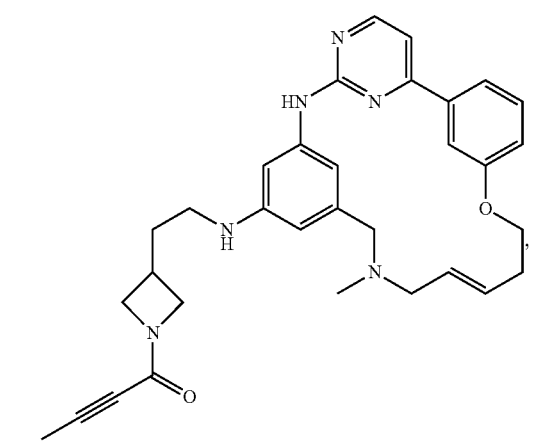
36
-continued
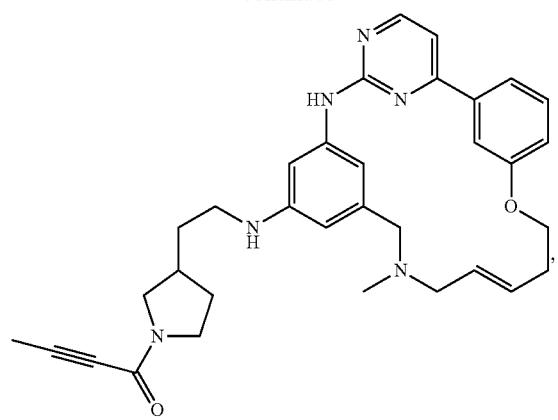
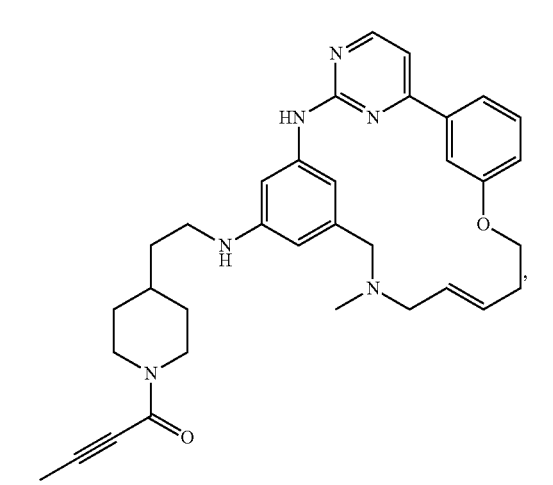
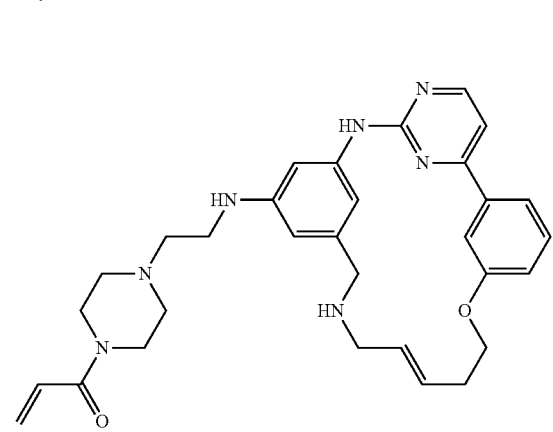
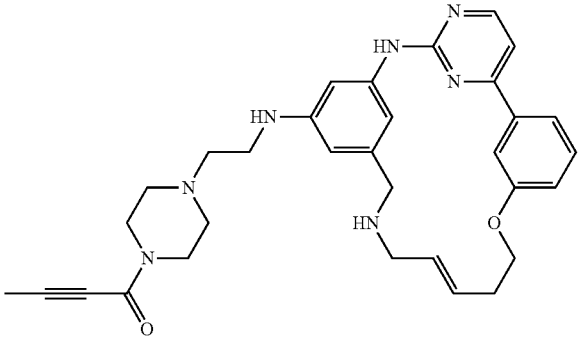

37
-continued
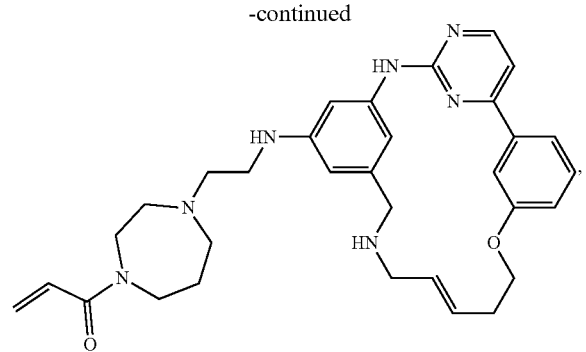
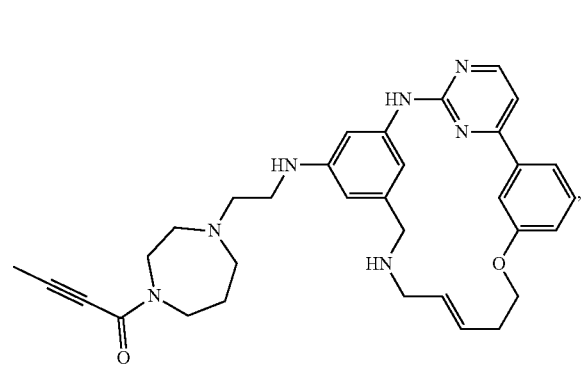
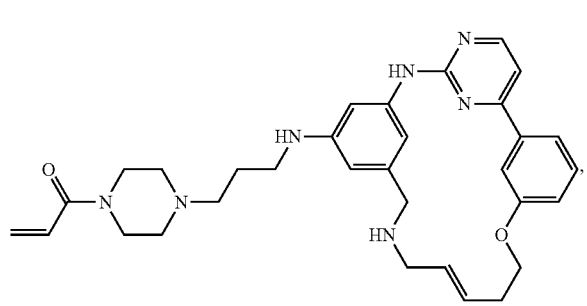
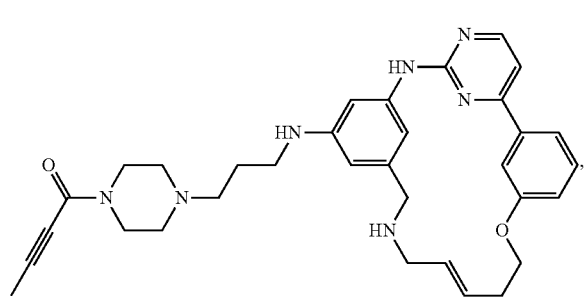
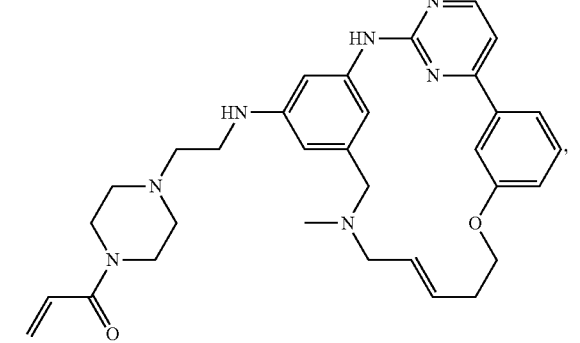
38
-continued
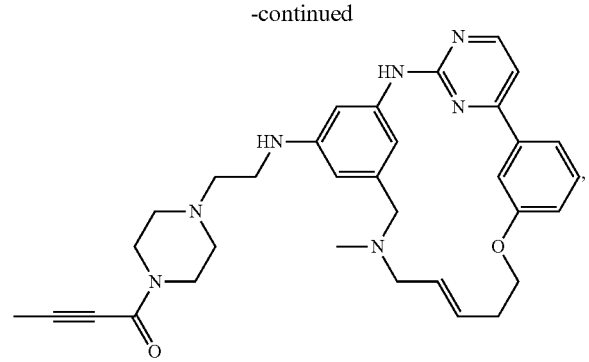
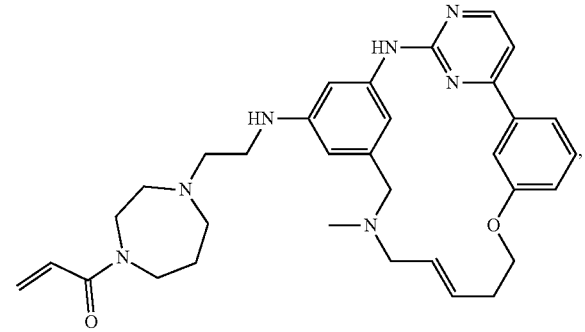
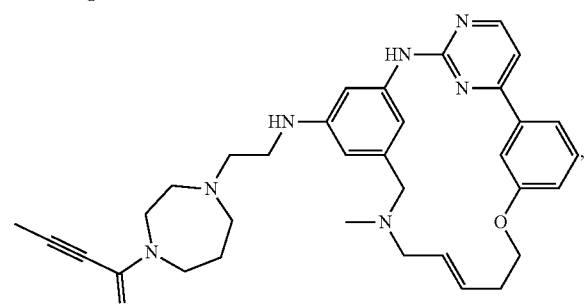
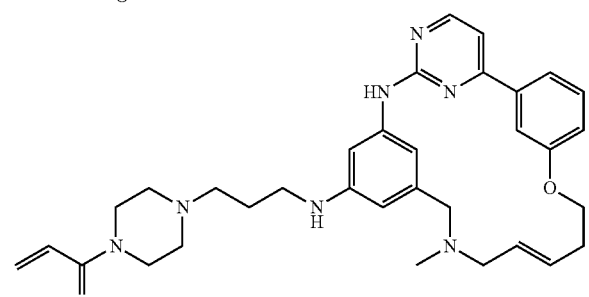
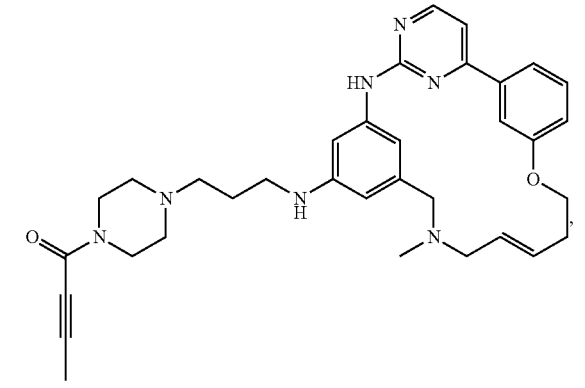

39
-continued
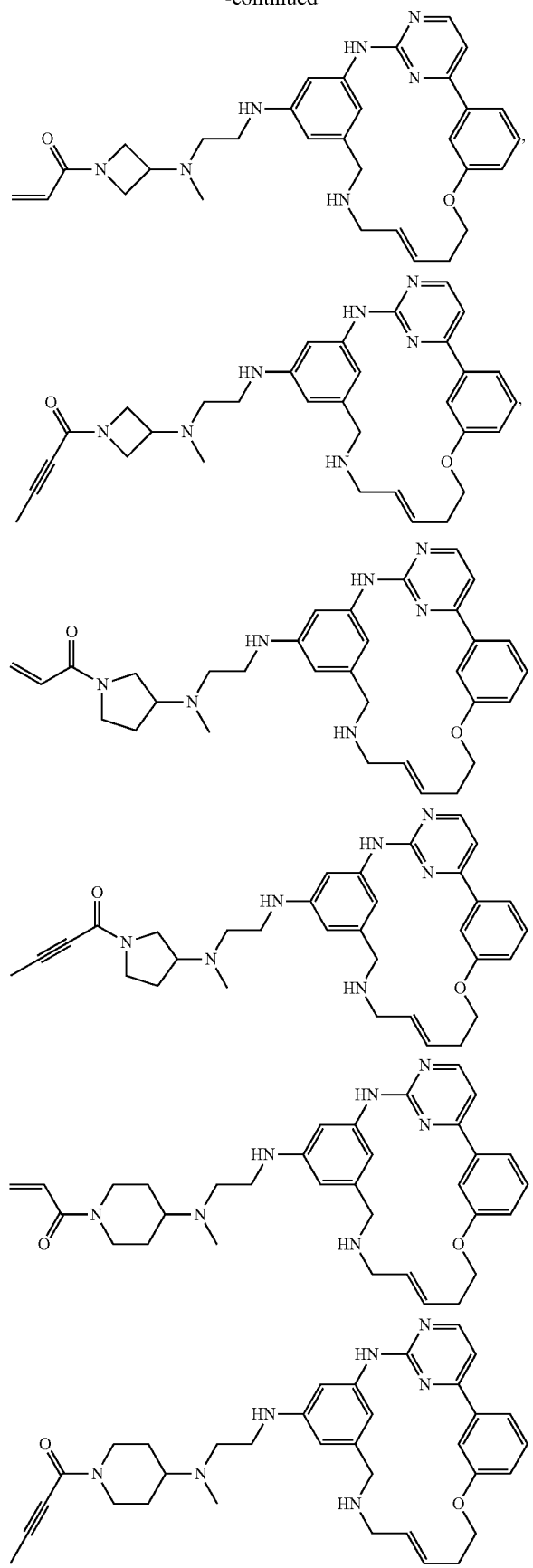
40
-continued
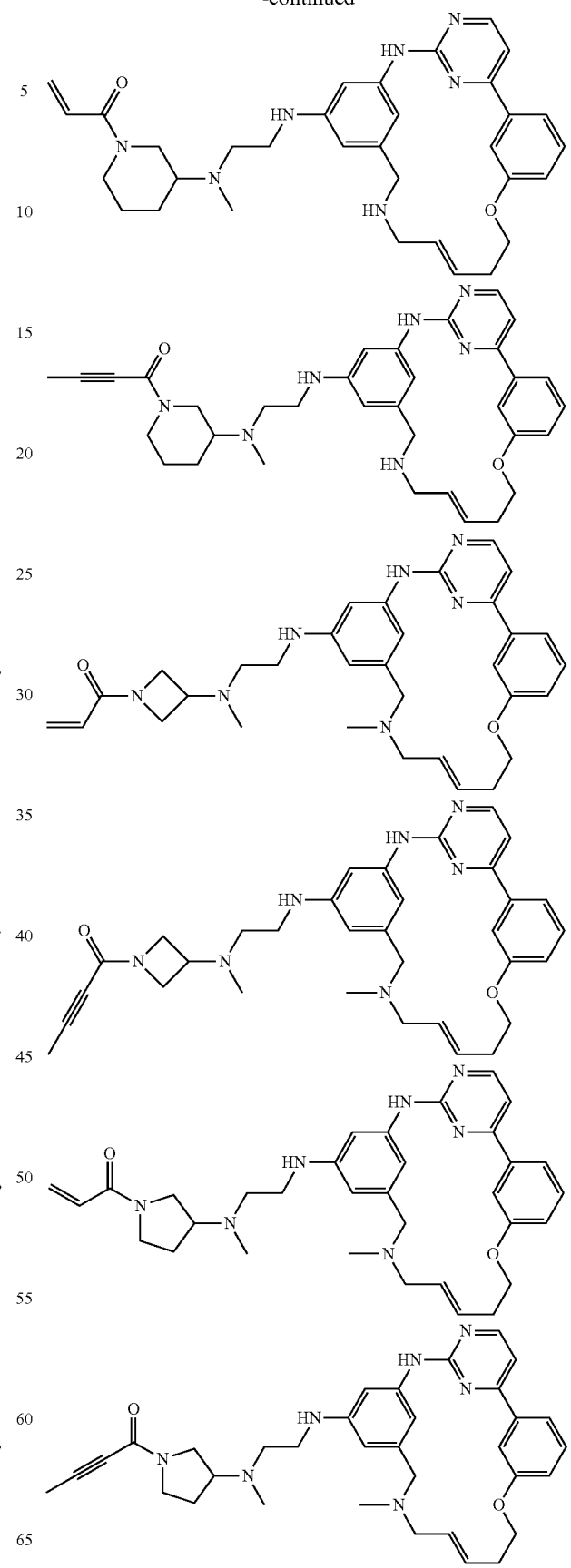

41
-continued
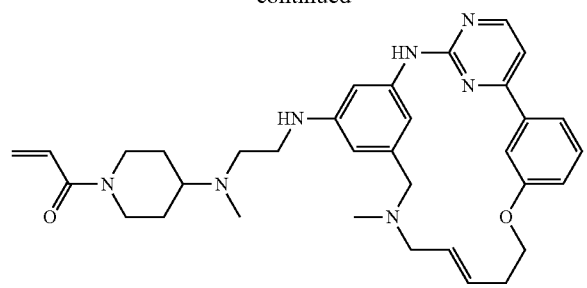
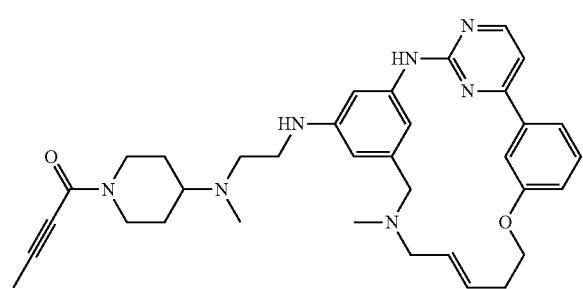
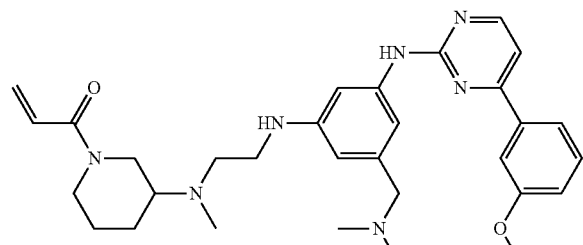
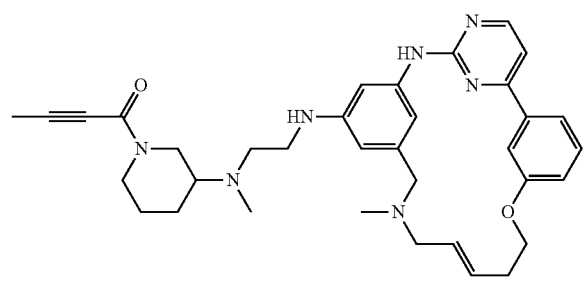
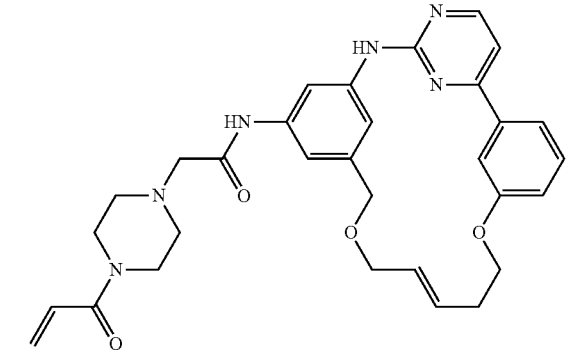
42
-continued
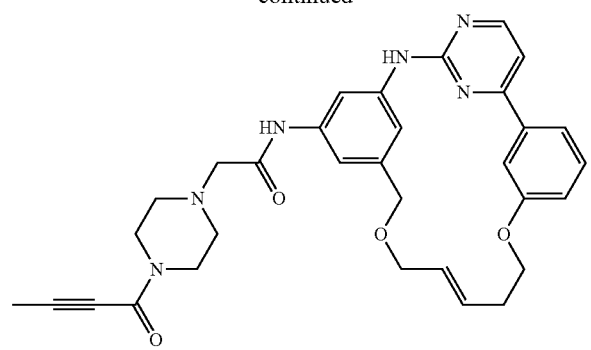
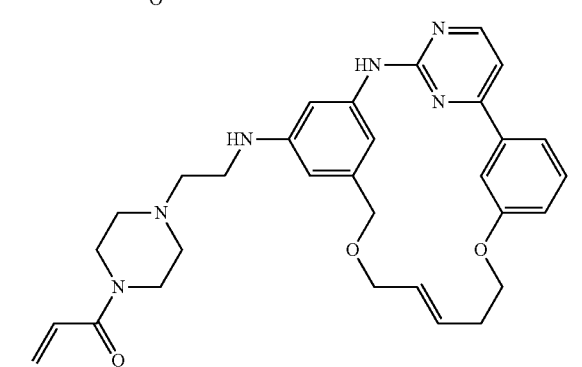
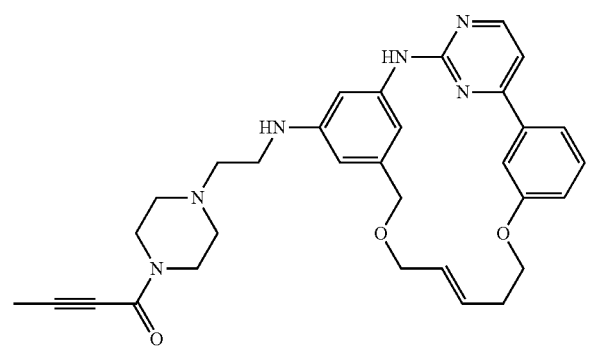
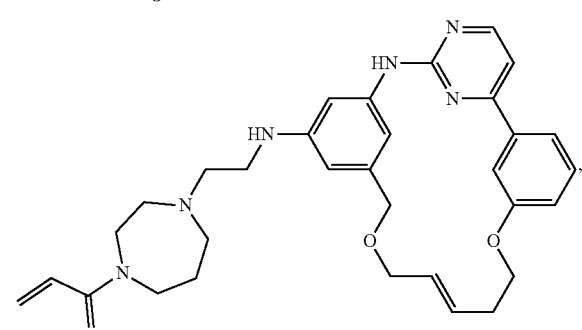
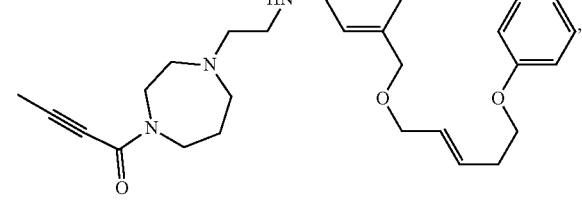

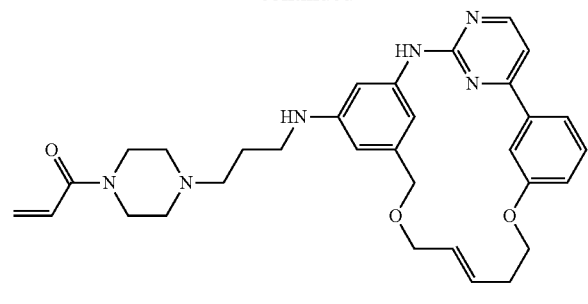
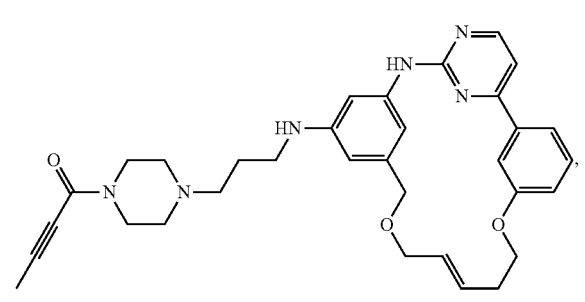
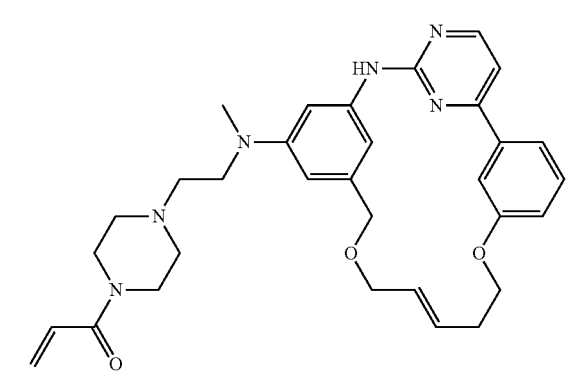
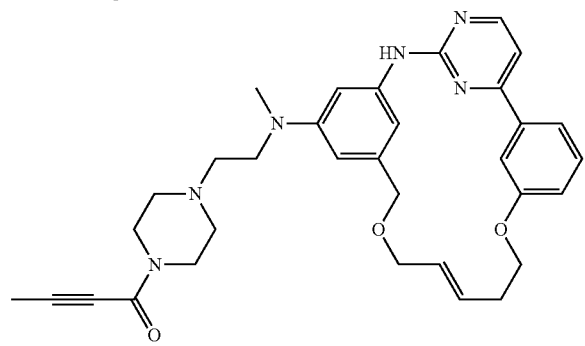
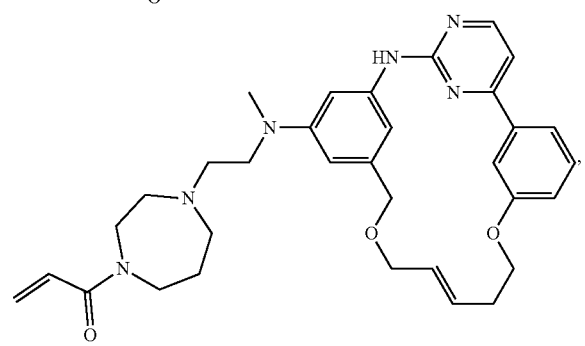
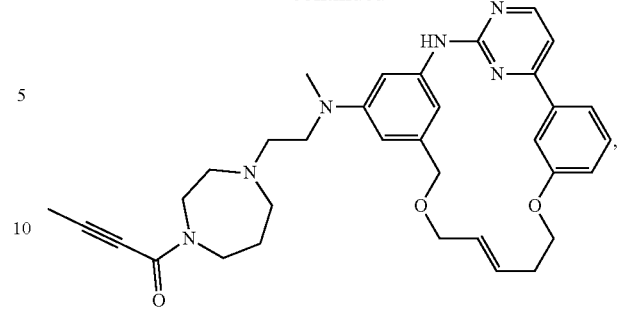
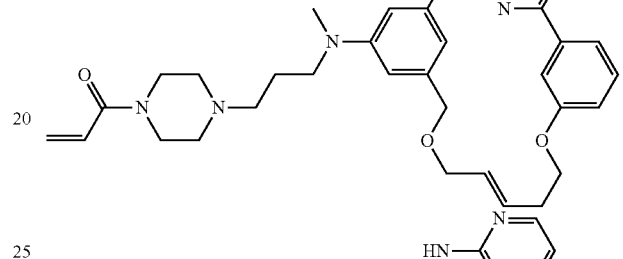
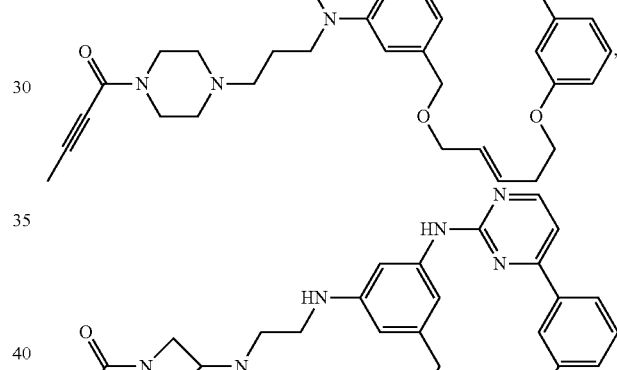
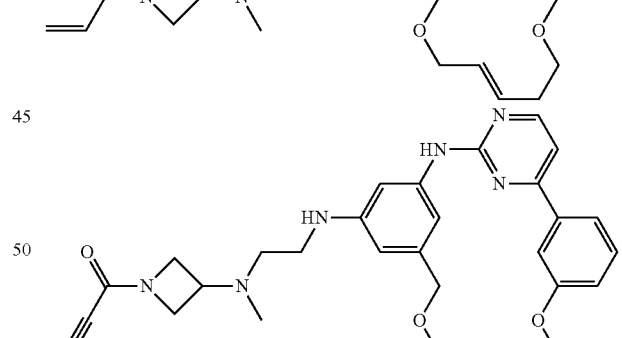
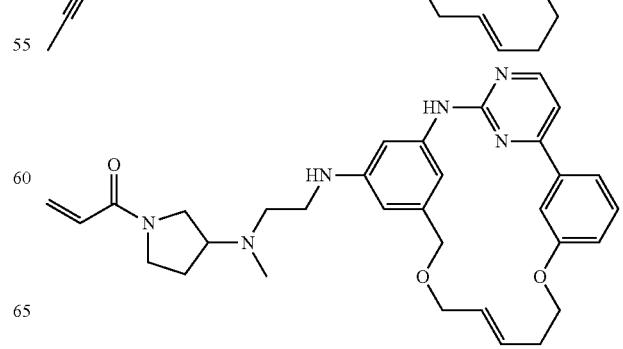

45
-continued
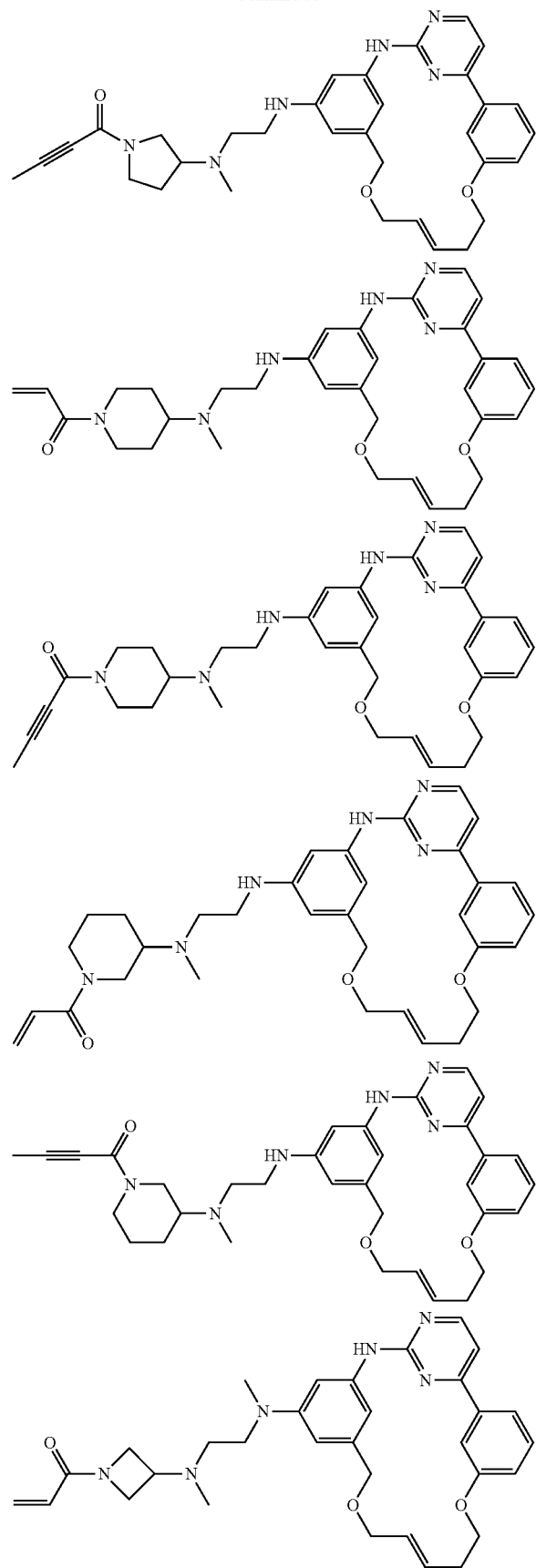
46
-continued
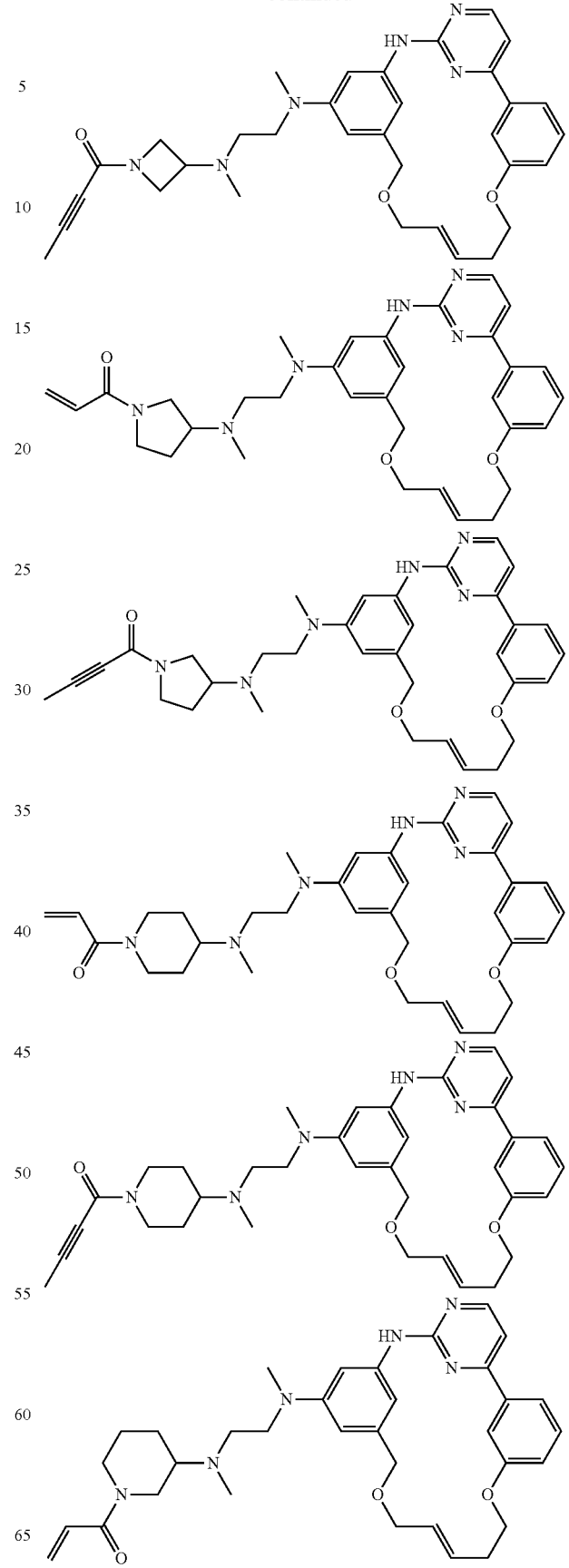

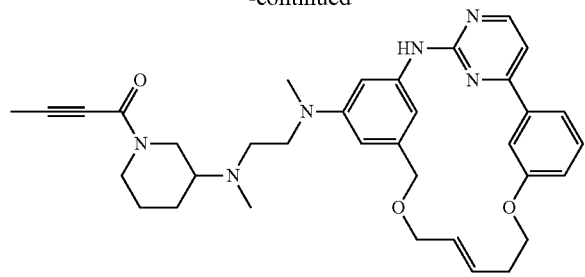

Compounds of the invention may contain one or more asymmetric carbon atoms. Accordingly, the compounds may exist as diastereomers, enantiomers or mixtures thereof. The syntheses of the compounds may employ racemates, diastereomers or enantiomers as starting materials or as intermediates. Diastereomeric compounds may be separated by chromatographic or crystallization methods. Similarly, enantiomeric mixtures may be separated using the same techniques or others known in the art. Each of the asymmetric carbon atoms may be in the R or S configuration and both of these configurations are within the scope of the invention.

A modified compound of any one of such compounds including a modification having an improved (e.g., enhanced, greater) pharmaceutical solubility, stability, bioavailability and/or therapeutic index as compared to the unmodified compound is also contemplated. The examples of modifications include but not limited to the prodrug derivatives, and the deuterium-enriched compounds. For example:

Prodrug derivatives: prodrugs, upon administration to a subject, will converted in vivo into active compounds of the present invention (*Nature Reviews of Drug Discovery*, 2008, 7:255). It is noted that in many instances, the prodrugs themselves also fall within the scope of the range of compounds according to the present invention. The prodrugs of the compounds of the present invention can be prepared by standard organic reaction, for example, by reacting with a carbamylating agent (e.g., 1,1-acyloxyalkylcarbonochloridate, para-nitrophenyl carbonate, or the like) or an acylating agent. Further examples of methods and strategies of making prodrugs are described in *Bioorganic and Medicinal Chemistry Letters*, 1994, 4:1985.

Deuterium-enriched compounds: deuterium (D or $^2H$) is H) a stable, non-radioactive isotope of hydrogen and has an atomic weight of 2.0144. Hydrogen naturally occurs as a mixture of the isotopes $^XH$ (hydrogen or protium), D ($^2H$ or deuterium), and T ($^3H$ or tritium). The natural abundance of deuterium is 0.015%. One of ordinary skill in the art recognizes that in all chemical compounds with a H atom, the H atom actually represents a mixture of H and D, with about 0.015% being D. Thus, compounds with a level of deuterium that has been enriched to be greater than its natural abundance of 0.015%, should be considered unnatural and, as a result, novel over their nonenriched counterparts.

It should be recognized that the compounds of the present invention may be present and optionally administered in the form of salts, and solvates. For example, it is within the scope of the present invention to convert the compounds of the present invention into and use them in the form of their pharmaceutically acceptable salts derived from various organic and inorganic acids and bases in accordance with procedures well known in the art.

When the compounds of the present invention possess a free base form, the compounds can be prepared as a pharmaceutically acceptable acid addition salt by reacting the free base form of the compound with a pharmaceutically acceptable inorganic or organic acid, e.g., hydrohalides such as hydrochloride, hydrobromide, hydroiodide; other mineral acids such as sulfate, nitrate, phosphate, etc.; and alkyl and monoarylsulfonates such as ethanesulfonate, toluenesulfonate and benzenesulfonate; and other organic acids and their corresponding salts such as acetate, tartrate, maleate, succinate, citrate, benzoate, salicylate and ascorbate. Further acid addition salts of the present invention include, but are not limited to: adipate, alginate, arginate, aspartate, bisulfate, bisulfite, bromide, butyrate, camphorate, camphorsulfonate, caprylate, chloride, chlorobenzoate, cyclopentanepropionate, digluconate, dihydrogenphosphate, dinitrobenzoate, dodecylsulfate, fumarate, galacterate (from mucic acid), galacturonate, glucoheptaoate, gluconate, glutamate, glycerophosphate, hemisuccinate, hemisulfate, heptanoate, hexanoate, hippurate, 2-hydroxyethanesulfonate, iodide, isethionate, iso-butyrate, lactate, lactobionate, malonate, mandelate, metaphosphate, methanesulfonate, methylbenzoate, monohydrogenphosphate, 2-naphthalenesulfonate, nicotinate, oxalate, oleate, pamoate, pectinate, persulfate, phenylacetate, 3-phenylpropionate, phosphonate and phthalate. It should be recognized that the free base forms will typically differ from their respective salt forms somewhat in physical properties such as solubility in polar solvents, but otherwise the salts are equivalent to their respective free base forms for the purposes of the present invention.

When the compounds of the present invention possess a free acid form, a pharmaceutically acceptable base addition salt can be prepared by reacting the free acid form of the compound with a pharmaceutically acceptable inorganic or organic base. Examples of such bases are alkali metal hydroxides including potassium, sodium and lithium hydroxides; alkaline earth metal hydroxides such as barium and calcium hydroxides; alkali metal alkoxides, e.g., potassium ethanolate and sodium propanolate; and various organic bases such as ammonium hydroxide, piperidine, diethanolamine and N-methylglutamine. Also included are the aluminum salts of the compounds of the present invention. Further base salts of the present invention include, but are not limited to: copper, ferric, ferrous, lithium, magnesium, manganic, manganous, potassium, sodium and zinc salts. Organic base salts include, but are not limited to, salts of primary, secondary and tertiary amines, substituted amines including naturally occurring substituted amines, cyclic amines and basic ion exchange resins, e.g., arginine, betaine, caffeine, chloroprocaine, choline, N,N'-dibenzylethylenediamine (benzathine), dicyclohexylamine, diethanolamine, 2-diethylaminoethanol, 2-dimethylaminoethanol, ethanolamine, ethylenediamine, N-ethylmorpholine, N-ethylpiperidine, glucamine, glucosamine, histidine, hydrabamine, iso-propylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris-(hydroxymethyl)-methylamine (tromethamine). It should be recognized that the free acid forms will typically differ from their respective salt forms somewhat in physical properties such as solubility in polar solvents, but otherwise the salts are equivalent to their respective free acid forms for the purposes of the present invention.

In one aspect, a pharmaceutically acceptable salt is a hydrochloride salt, hydrobromide salt, methanesulfonate, toluenesulfonate, acetate, fumarate, sulfate, bisulfate, succinate, citrate, phosphate, maleate, nitrate, tartrate, benzoate, biocarbonate, carbonate, sodium hydroxide salt, calcium hydroxide salt, potassium hydroxide salt, tromethamine salt, or mixtures thereof.

Compounds of the present invention that comprise tertiary nitrogen-containing groups may be quaternized with such agents as $(C_{1-4})$ alkyl halides, e.g., methyl, ethyl, iso-propyl and tert-butyl chlorides, bromides and iodides; di-$(C_{1-4})$ alkyl sulfates, e.g., dimethyl, diethyl and diamyl sulfates; alkyl halides, e.g., decyl, dodecyl, lauryl, myristyl and stearyl chlorides, bromides and iodides; and aryl $(C_{1-4})$ alkyl halides, e.g., benzyl chloride and phenethyl bromide. Such salts permit the preparation of both water- and oil-soluble compounds of the invention.

Amine oxides, also known as amine-N-oxide and N-oxide, of anti-cancer agents with tertiary nitrogen atoms have been developed as prodrugs (*Mol. Cancer Therapy*, 2004 March; 3(3):233-244). Compounds of the present invention that comprise tertiary nitrogen atoms may be oxidized by such agents as hydrogen peroxide ($H_2O_2$), Caro's acid or peracids like meta-Chloroperoxybenzoic acid (mCPBA) to from amine oxide.

The invention encompasses pharmaceutical compositions comprising the compound of the present invention and pharmaceutical excipients, as well as other conventional pharmaceutically inactive agents. Any inert excipient that is commonly used as a carrier or diluent may be used in compositions of the present invention, such as sugars, polyalcohols, soluble polymers, salts and lipids. Sugars and polyalcohols which may be employed include, without limitation, lactose, sucrose, mannitol, and sorbitol. Illustrative of the soluble polymers which may be employed are polyoxyethylene, poloxamers, polyvinylpyrrolidone, and dextran. Useful salts include, without limitation, sodium chloride, magnesium chloride, and calcium chloride. Lipids which may be employed include, without limitation, fatty acids, glycerol fatty acid esters, glycolipids, and phospholipids.

In addition, the pharmaceutical compositions may further comprise binders (e.g., acacia, cornstarch, gelatin, carbomer, ethyl cellulose, guar gum, hydroxypropyl cellulose, hydroxypropyl methyl cellulose, povidone), disintegrating agents (e.g., cornstarch, potato starch, alginic acid, silicon dioxide, croscarmellose sodium, crospovidone, guar gum, sodium starch glycolate, Primogel), buffers (e.g., tris-HCL, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g., sodium lauryl sulfate), permeation enhancers, solubilizing agents (e.g., glycerol, polyethylene glycerol, cyclodextrins), a glidant (e.g., colloidal silicon dioxide), anti-oxidants (e.g., ascorbic acid, sodium metabisulfite, butylated hydroxyanisole), stabilizers (e.g., hydroxypropyl cellulose, hydroxypropylmethyl cellulose), viscosity increasing agents (e.g., carbomer, colloidal silicon dioxide, ethyl cellulose, guar gum), sweeteners (e.g., sucrose, aspartame, citric acid), flavoring agents (e.g., peppermint, methyl salicylate, or orange flavoring), preservatives (e.g., Thimerosal, benzyl alcohol, parabens), lubricants (e.g., stearic acid, magnesium stearate, polyethylene glycol, sodium lauryl sulfate), flow-aids (e.g., colloidal silicon dioxide), plasticizers (e.g., diethyl phthalate, triethyl citrate), emulsifiers (e.g., carbomer, hydroxypropyl cellulose, sodium lauryl sulfate, methyl cellulose, hydroxyethyl cellulose, carboxymethylcellulose sodium), polymer coatings (e.g., poloxamers or poloxamines), coating and film forming agents (e.g., ethyl cellulose, acrylates, polymethacrylates) and/or adjuvants.

In one embodiment, the pharmaceutical compositions are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Additionally, the invention encompasses pharmaceutical compositions comprising any solid or liquid physical form of the compound of the invention. For example, the compounds can be in a crystalline form, in amorphous form, and have any particle size. The particles may be micronized, or may be agglomerated, particulate granules, powders, oils, oily suspensions or any other form of solid or liquid physical form.

When compounds according to the present invention exhibit insufficient solubility, methods for solubilizing the compounds may be used. Such methods are known to those of skill in this art, and include, but are not limited to, pH adjustment and salt formation, using co-solvents, such as ethanol, propylene glycol, polyethylene glycol (PEG) 300, PEG 400, DMA (10-30%), DMSO (10-20%), NMP (10-20%), using surfactants, such as polysorbate 80, polysorbate 20 (1-10%), cremophor EL, Cremophor RH40, Cremophor RH60 (5-10%), Pluronic F68/Poloxamer 188 (20-50%), Solutol HS15 (20-50%), Vitamin E TPGS, and d-α-tocopheryl PEG 1000 succinate (20-50%), using complexation such as HPβCD and SBEβCD (10-40%), and using advanced approaches such as micelle, addition of a polymer, nanoparticle suspensions, and liposome formation.

A wide variety of administration methods may be used in conjunction with the compounds of the present invention. Compounds of the present invention may be administered or coadministered orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, or intrathecally. The compounds according to the invention may also be administered or coadministered in slow release dosage forms. Compounds may be in gaseous, liquid, semi-liquid or solid form, formulated in a manner suitable for the route of administration to be used. For oral administration, suitable solid oral formulations include tablets, capsules, pills, granules, pellets, sachets and effervescent, powders, and the like. Suitable liquid oral formulations include solutions, suspensions, dispersions, emulsions, oils and the like. For parenteral administration, reconstitution of a lyophilized powder is typically used.

As used herein, "acyl" means a carbonyl containing substituent represented by the formula —C(O)—R in which R is H, alkyl, a carbocycle, a heterocycle, carbocycle-substituted alkyl or heterocycle-substituted alkyl wherein the alkyl, alkoxy, carbocycle and heterocycle are as defined herein. Acyl groups include alkanoyl (e.g. acetyl), aroyl (e.g. benzoyl), and heteroaroyl.

"Aliphatic" means a moiety characterized by a straight or branched chain arrangement of constituent carbon atoms and may be saturated or partially unsaturated with one or more double or triple bonds.

The term "alkyl" refers to a straight or branched hydrocarbon containing 1-20 carbon atoms (e.g., $C_1$-$C_{10}$). Examples of alkyl include, but are not limited to, methyl, methylene, ethyl, ethylene, n-propyl, i-propyl, n-butyl, i-butyl, and t-butyl. Preferably, the alkyl group has one to ten carbon atoms. More preferably, the alkyl group has one to four carbon atoms.

The term "alkenyl" refers to a straight or branched hydrocarbon containing 2-20 carbon atoms (e.g., $C_2$-$C_{10}$) and one or more double bonds. Examples of alkenyl include, but are not limited to, ethenyl, propenyl, and allyl. Preferably, the alkylene group has two to ten carbon atoms. More preferably, the alkylene group has two to four carbon atoms.

The term "alkynyl" refers to a straight or branched hydrocarbon containing 2-20 carbon atoms (e.g., $C_2$-$C_{10}$) and one or more triple bonds. Examples of alkynyl include, but are not limited to, ethynyl, 1-propynyl, 1- and 2-butynyl, and 1-methyl-2-butynyl. Preferably, the alkynyl group has two to ten carbon atoms. More preferably, the alkynyl group has two to four carbon atoms.

The term "alkylamino" refers to an —N(R)-alkyl in which R can be H, alkyl, alkenyl, alkynyl, cycloalkyl, cycloalkenyl, heterocycloalkyl, heterocycloalkenyl, aryl, or heteroaryl.

"Alkoxy" means an oxygen moiety having a further alkyl substituent.

"Alkoxycarbonyl" means an alkoxy group attached to a carbonyl group.

"Oxoalkyl" means an alkyl, further substituted with a carbonyl group. The carbonyl group may be an aldehyde, ketone, ester, amide, acid or acid chloride.

The term "cycloalkyl" refers to a saturated hydrocarbon ring system having 3 to 30 carbon atoms (e.g., $C_3$-$C_{12}$, $C_3$-$C_8$, $C_3$-$C_6$). Examples of cycloalkyl include, but are not limited to, cyclopropyl, cyclobutyl, cyclopentyl, cyclohexyl, cycloheptyl, and cyclooctyl. The term "cycloalkenyl" refers to a non-aromatic hydrocarbon ring system having 3 to 30 carbons (e.g., $C_3$-$C_{12}$) and one or more double bonds. Examples include cyclopentenyl, cyclohexenyl, and cycloheptenyl.

The term "heterocycloalkyl" refers to a nonaromatic 5-8 membered monocyclic, 8-12 membered bicyclic, or 11-14 membered tricyclic ring system having one or more heteroatoms (such as O, N, S, P, or Se). Examples of heterocycloalkyl groups include, but are not limited to, piperazinyl, pyrrolidinyl, dioxanyl, morpholinyl, and tetrahydrofuranyl.

The term "heterocycloalkenyl" refers to a nonaromatic 5-8 membered monocyclic, 8-12 membered bicyclic, or 11-14 membered tricyclic ring system having one or more heteroatoms (such as O, N, S, P, or Se) and one or more double bonds.

The term "aryl" refers to a 6-carbon monocyclic, 10-carbon bicyclic, 14-carbon tricyclic aromatic ring system. Examples of aryl groups include, but are not limited to, phenyl, naphthyl, and anthracenyl. The term "heteroaryl" refers to an aromatic 5-8 membered monocyclic, 8-12 membered bicyclic, or 11-14 membered tricyclic ring system having one or more heteroatoms (such as O, N, S, P, or Se).

Examples of heteroaryl groups include pyridyl, furyl, imidazolyl, benzimidazolyl, pyrimidinyl, thienyl, quinolinyl, indolyl, and thiazolyl.

Alkyl, alkenyl, alkynyl, cycloalkyl, heterocycloalkyl, cycloalkenyl, heterocycloalkenyl, alkylamino, aryl, and heteroaryl mentioned above include both substituted and unsubstituted moieties. Possible substituents on alkylamino, cycloalkyl, heterocycloalkyl, cycloalkenyl, heterocycloalkenyl, aryl, and heteroaryl include, but are not limited to, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, $C_1$-$C_{10}$ alkoxy, aryl, aryloxy, heteroaryl, heteroaryloxy, amino, $C_1$-$C_{10}$ alkylamino, arylamino, hydroxy, halo, oxo (O=), thioxo (S=), thio, silyl, $C_1$-$C_{10}$ alkylthio, arylthio, $C_1$-$C_{10}$ alkylsulfonyl, arylsulfonyl, acylamino, aminoacyl, aminothioacyl, amidino, mercapto, amido, thioureido, thiocyanato, sulfonamido, guanidine, ureido, cyano, nitro, acyl, thioacyl, acyloxy, carbamido, carbamyl, carboxyl, and carboxylic ester. On the other hand, possible substituents on alkyl, alkenyl, or alkynyl include all of the above-recited substituents except $C_1$-$C_{10}$ alkyl. Cycloalkyl, cycloalkenyl, heterocycloalkyl, heterocycloalkenyl, aryl, and heteroaryl can also be fused with each other.

"Amino" means a nitrogen moiety having two further substituents where each substituent has a hydrogen or carbon atom alpha bonded to the nitrogen. Unless indicated otherwise, the compounds of the invention containing amino moieties may include protected derivatives thereof. Suitable protecting groups for amino moieties include acetyl, tert-butoxycarbonyl, benzyloxycarbonyl, and the like.

"Aromatic" means a moiety wherein the constituent atoms make up an unsaturated ring system, all atoms in the ring system are sp2 hybridized and the total number of pi electrons is equal to 4n+2. An aromatic ring may be such that the ring atoms are only carbon atoms or may include carbon and non-carbon atoms (see Heteroaryl).

"Carbamoyl" means the radical —OC(O)NR$_a$R$_b$ where R$_a$ and R$_b$ are each independently two further substituents where a hydrogen or carbon atom is alpha to the nitrogen. It is noted that carbamoyl moieties may include protected derivatives thereof. Examples of suitable protecting groups for carbamoyl moieties include acetyl, tert-butoxycarbonyl, benzyloxycarbonyl, and the like. It is noted that both the unprotected and protected derivatives fall within the scope of the invention.

"Carbonyl" means the radical —C(O)—. It is noted that the carbonyl radical may be further substituted with a variety of substituents to form different carbonyl groups including acids, acid halides, amides, esters, and ketones.

"Carboxy" means the radical —C(O)O—. It is noted that compounds of the invention containing carboxy moieties may include protected derivatives thereof, i.e., where the oxygen is substituted with a protecting group. Suitable protecting groups for carboxy moieties include benzyl, tert-butyl, and the like.

"Cyano" means the radical —CN.

"Formyl" means the radical —CH=O.

"Formimino" means the radical —HC=NH.

"Halo" means fluoro, chloro, bromo or iodo.

"Halo-substituted alkyl," as an isolated group or part of a larger group, means "alkyl" substituted by one or more "halo" atoms, as such terms are defined in this Application. Halo-substituted alkyl includes haloalkyl, dihaloalkyl, trihaloalkyl, perhaloalkyl and the like.

"Hydroxy" means the radical —OH.

"Imine derivative" means a derivative comprising the moiety —C(=NR)—, wherein R comprises a hydrogen or carbon atom alpha to the nitrogen.

"Isomers" mean any compound having identical molecular formulae but differing in the nature or sequence of bonding of their atoms or in the arrangement of their atoms in space. Isomers that differ in the arrangement of their atoms in space are termed "stereoisomers." Stereoisomers that are not mirror images of one another are termed "diastereomers" and stereoisomers that are nonsuperimposable mirror images are termed "enantiomers" or sometimes "optical isomers." A carbon atom bonded to four nonidentical substituents is termed a "chiral center." A compound with one chiral center has two enantiomeric forms of opposite chirality. A mixture of the two enantiomeric forms is termed a "racemic mixture."

"Nitro" means the radical —$NO_2$.

"Protected derivatives" means derivatives of compounds in which a reactive site are blocked with protecting groups. Protected derivatives are useful in the preparation of pharmaceuticals or in themselves may be active as inhibitors. A comprehensive list of suitable protecting groups can be found in T. W. Greene, *Protecting Groups in Organic Synthesis,* 3rd edition, Wiley & Sons, 1999.

The term "substituted" means that an atom or group of atoms has replaced hydrogen as the substituent attached to another group. For aryl and heteroaryl groups, the term "substituted" refers to any level of substitution, namely mono-, di-, tri-, tetra-, or penta-substitution, where such substitution is permitted. The substituents are independently selected, and substitution may be at any chemically accessible position. The term "unsubstituted" means that a given moiety may consist of only hydrogen substituents through available valencies (unsubstituted).

If a functional group is described as being "optionally substituted," the function group may be either (1) not substituted, or (2) substituted. If a carbon of a functional group is described as being optionally substituted with one or more of a list of substituents, one or more of the hydrogen atoms on the carbon (to the extent there are any) may separately and/or together be replaced with an independently selected optional substituent.

"Sulfide" means —S—R wherein R is H, alkyl, carbocycle, heterocycle, carbocycloalkyl or heterocycloalkyl. Particular sulfide groups are mercapto, alkylsulfide, for example methylsulfide (—S-Me); arylsulfide, e.g., phenylsulfide; aralkylsulfide, e.g., benzylsulfide.

"Sulfinyl" means the radical —S(O)—. It is noted that the sulfinyl radical may be further substituted with a variety of substituents to form different sulfinyl groups including sulfinic acids, sulfinamides, sulfinyl esters, and sulfoxides.

"Sulfonyl" means the radical —S(O)(O)—. It is noted that the sulfonyl radical may be further substituted with a variety of substituents to form different sulfonyl groups including sulfonic acids, sulfonamides, sulfonate esters, and sulfones.

"Thiocarbonyl" means the radical —C(S)—. It is noted that the thiocarbonyl radical may be further substituted with a variety of substituents to form different thiocarbonyl groups including thioacids, thioamides, thioesters, and thioketones.

"Animal" includes humans, non-human mammals (e.g., non-human primates, rodents, mice, rats, hamsters, dogs, cats, rabbits, cattle, horses, sheep, goats, swine, deer, and the like) and non-mammals (e.g., birds, and the like).

"Bioavailability" as used herein is the fraction or percentage of an administered dose of a drug or pharmaceutical composition that reaches the systemic circulation intact. In general, when a medication is administered intravenously, its bioavailability is 100%. However, when a medication is administered via other routes (e.g., orally), its bioavailability decreases (e.g., due to incomplete absorption and first-pass metabolism). Methods to improve the bioavailability include prodrug approach, salt synthesis, particle size reduction, complexation, change in physical form, solid dispersions, spray drying, and hot-melt extrusion.

"Disease" specifically includes any unhealthy condition of an animal or part thereof and includes an unhealthy condition that may be caused by, or incident to, medical or veterinary therapy applied to that animal, i.e., the "side effects" of such therapy.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means organic or inorganic salts of compounds of the present invention which are pharmaceutically acceptable, as defined above, and which possess the desired pharmacological activity. Such salts include acid addition salts formed with inorganic acids, or with organic acids. Pharmaceutically acceptable salts also include base addition salts which may be formed when acidic protons present are capable of reacting with inorganic or organic bases. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate," ethanesulfonate, benzenesulfonate, p-toluenesulfonate, pamoate (i.e., 1,1'-methylene-bis-(2-hydroxy-3-naphthoate)) salts, alkali metal (e.g., sodium and potassium) salts, alkaline earth metal (e.g., magnesium) salts, and ammonium salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

"Pharmaceutically acceptable carrier" means a non-toxic solvent, dispersant, excipient, adjuvant, or other material which is mixed with the compounds of the present invention in order to form a pharmaceutical composition, i.e., a dose form capable of administration to the patient. Examples of pharmaceutically acceptable carrier includes suitable polyethylene glycol (e.g., PEG400), surfactant (e.g., Cremophor), or cyclopolysaccharide (e.g., hydroxypropyl-β-cyclodextrin or sulfobutyl ether β-cyclodextrins), polymer, liposome, micelle, nanosphere, etc.

"Pharmacophore," as defined by The International Union of Pure and Applied Chemistry, is an ensemble of steric and electronic features that is necessary to ensure the optimal supramolecular interactions with a specific biological target and to trigger (or block) its biological response. For example, Camptothecin is the pharmacophore of the well known drug topotecan and irinotecan. Mechlorethamine is the pharmacophore of a list of widely used nitrogen mustard drugs like Melphalan, Cyclophosphamide, Bendamustine, and so on.

"Prodrug" means a compound that is convertible in vivo metabolically into an active pharmaceutical according to the present invention. For example, an inhibitor comprising a hydroxyl group may be administered as an ester that is converted by hydrolysis in vivo to the hydroxyl compound.

"Stability" in general refers to the length of time a drug retains its properties without loss of potency. Sometimes this is referred to as shelf life. Factors affecting drug stability include, among other things, the chemical structure of the drug, impurity in the formulation, pH, moisture content, as well as environmental factors such as temperature, oxidization, light, and relative humidity. Stability can be improved by providing suitable chemical and/or crystal modifications (e.g., surface modifications that can change hydration kinetics; different crystals that can have different properties), excipients (e.g., anything other than the active substance in the dosage form), packaging conditions, storage conditions, etc.

"Therapeutically effective amount" of a composition described herein is meant an amount of the composition which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). An effective amount of the composition described above may range from about 0.1 mg/kg to about 500 mg/kg, preferably from about 0.2 to about 50 mg/kg. Effective doses will also vary depending on route of administration, as well as the possibility of co-usage with other agents. It will be understood, however, that the total daily usage of the compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

As used herein, the term "treating" refers to administering a compound to a subject that has a neoplastic or immune disorder, or has a symptom of or a predisposition toward it, with the purpose to cure, heal, alleviate, relieve, alter, remedy, ameliorate, improve, or affect the disorder, the symptoms of or the predisposition toward the disorder. The term "an effective amount" refers to the amount of the active agent that is required to confer the intended therapeutic effect in the subject. Effective amounts may vary, as recognized by those skilled in the art, depending on route of administration, excipient usage, and the possibility of co-usage with other agents.

A "subject" refers to a human and a non-human animal. Examples of a non-human animal include all vertebrates, e.g., mammals, such as non-human primates (particularly higher primates), dog, rodent (e.g., mouse or rat), guinea pig, cat, and non-mammals, such as birds, amphibians, reptiles, etc. In a preferred embodiment, the subject is a human. In another embodiment, the subject is an experimental animal or animal suitable as a disease model.

"Combination therapy" includes the administration of the subject compounds of the present invention in further combination with other biologically active ingredients (such as, but not limited to, a second and different antineoplastic agent) and non-drug therapies (such as, but not limited to, surgery or radiation treatment). For instance, the compounds of the invention can be used in combination with other pharmaceutically active compounds, or non-drug therapies, preferably compounds that are able to enhance the effect of the compounds of the invention. The compounds of the invention can be administered simultaneously (as a single preparation or separate preparation) or sequentially to the other therapies. In general, a combination therapy envisions administration of two or more drugs/treatments during a single cycle or course of therapy.

In one embodiment, the compounds of the invention are administered in combination with one or more of traditional chemotherapeutic agents. The traditional chemotherapeutic agents encompass a wide range of therapeutic treatments in the field of oncology. These agents are administered at various stages of the disease for the purposes of shrinking tumors, destroying remaining cancer cells left over after surgery, inducing remission, maintaining remission and/or alleviating symptoms relating to the cancer or its treatment. Examples of such agents include, but are not limited to, alkylating agents such as Nitrogen Mustards (e.g., Bendamustine, Cyclophosphamide, Melphalan, Chlorambucil, Isofosfamide), Nitrosureas (e.g., Carmustine, Lomustine and Streptozocin), ethylenimines (e.g., thiotepa, hexamethylmelanine), Alkylsulfonates (e.g., Busulfan), Hydrazines and Triazines (e.g., Altretamine, Procarbazine, Dacarbazine and Temozolomide), and platinum based agents (e.g., Carboplatin, Cisplatin, and Oxaliplatin); plant alkaloids such as Podophyllotoxins (e.g., Etoposide and Tenisopide), Taxanes (e.g., Paclitaxel and Docetaxel), Vinca alkaloids (e.g., Vincristine, Vinblastine and Vinorelbine); anti-tumor antibiotics such as Chromomycins (e.g., Dactinomycin and Plicamycin), Anthracyclines (e.g., Doxorubicin, Daunorubicin, Epirubicin, Mitoxantrone, and Idarubicin), and miscellaneous antibiotics such as Mitomycin and Bleomycin; anti-metabolites such as folic acid antagonists (e.g., Methotrexate), pyrimidine antagonists (e.g., 5-Fluorouracil, Foxuridine, Cytarabine, Capecitabine, and Gemcitabine), purine antagonists (e.g., 6-Mercaptopurine and 6-Thioguanine) and adenosine deaminase inhibitors (e.g., Cladribine, Fludarabine, Nelarabine and Pentostatin); topoisomerase inhibitors such as topoisomerase I inhibitors (Topotecan, Irinotecan), topoisomerase II inhibitors (e.g., Amsacrine, Etoposide, Etoposide phosphate, Teniposide), and miscellaneous antineoplastics such as ribonucleotide reductase inhibitors (Hydroxyurea), adrenocortical steroid inhibitor (Mitotane), anti-microtubule agents (Estramustine), and retinoids (Bexarotene, Isotretinoin, Tretinoin (ATRA).

In one aspect of the invention, the compounds may be administered in combination with one or more targeted anti-cancer agents that modulate protein kinases involved in various disease states. Examples of such kinases may include, but are not limited ABL1, ABL2/ARG, ACK1, AKT1, AKT2, AKT3, ALK, ALK1/ACVRL1, ALK2/ACVR1, ALK4/ACVR1B, ALK5/TGFBR1, ALK6/BMPR1B, AMPK(A1/B1/G1), AMPK(A1/B1/G2), AMPK(A1/B1/G3), AMPK(A1/B2/G1), AMPK(A2/B1/G1), AMPK(A2/B2/G1), AMPK(A2/B2/G2), ARAF, ARK5/NUAK1, ASK1/MAP3K5, ATM, Aurora A, Aurora B, Aurora C, AXL, BLK, BMPR2, BMX/ETK, BRAF, BRK, BRSK1, BRSK2, BTK, CAMK1a, CAMK1b, CAMK1d, CAMK1g, CAMKIIa, CAMKIIb, CAMKIId, CAMKIIg, CAMK4, CAMKK1, CAMKK2, CDC7-DBF4, CDK1-cyclin A, CDK1-cyclin B, CDK1-cyclin E, CDK2-cyclin A, CDK2-cyclin A1, CDK2-cyclin E, CDK3-cyclin E, CDK4-cyclin D1, CDK4-cyclin D3, CDK5-p25, CDK5-p35, CDK6-cyclin D1, CDK6-cyclin D3, CDK7-cyclin H, CDK9-cyclin K, CDK9-cyclin T1, CHK1, CHK2, CK1a1, CK1d, CK1epsilon, CK1g1, CK1g2, CK1g3, CK2a, CK2a2, c-KIT, CLK1, CLK2, CLK3, CLK4, c-MER, c-MET, COT1/MAP3K8, CSK, c-SRC, CTK/MATK, DAPK1, DAPK2, DCAMKL1, DCAMKL2, DDR1, DDR2, DLK/MAP3K12, DMPK, DMPK2/CDC42BPG, DNA-PK, DRAK1/STK17A, DYRK1/DYRK1A, DYRK1B, DYRK2, DYRK3, DYRK4, EEF2K, EGFR, EIF2AK1, EIF2AK2, EIF2AK3, EIF2AK4/GCN2, EPHA1, EPHA2, EPHA3, EPHA4, EPHA5, EPHA6, EPHA7, EPHA8, EPHB1, EPHB2, EPHB3, EPHB4, ERBB2/HER2, ERBB4/HER4, ERK1/MAPK3, ERK2/MAPK1, ERK5/MAPK7, FAK/PTK2, FER, FES/FPS, FGFR1, FGFR2, FGFR3, FGFR4, FGR, FLT1/VEGFR1, FLT3, FLT4/VEGFR3, FMS, FRK/PTK5, FYN, GCK/MAP4K2, GRK1, GRK2, GRK3, GRK4, GRK5, GRK6, GRK7, GSK3a, GSK3b, Haspin, HCK, HGK/MAP4K4, HIPK1, HIPK2, HIPK3, HIPK4, HPK1/MAP4K1, IGF1R, IKKa/CHUK, IKKb/IKBKB, IKKe/IKBKE, IR, IRAK1, IRAK4, IRR/INSRR, ITK, JAK1, JAK2, JAK3, JNK1, JNK2, JNK3, KDR/VEGFR2, KHS/MAP4K5, LATS1, LATS2, LCK, LCK2/ICK, LKB1, LIMK1, LOK/STK10, LRRK2, LYN, LYNB, MAPKAPK2, MAPKAPK3, MAPKAPK5/PRAK, MARK1, MARK2/PAR-1Ba, MARK3, MARK4, MEK1, MEK2, MEKK1, MEKK2, MEKK3, MELK, MINK/MINK1, MKK4, MKK6, MLCK/MYLK, MLCK2/MYLK2, MLK1/MAP3K9, MLK2/MAP3K10, MLK3/MAP3K11, MNK1, MNK2, MRCKa/, CDC42BPA, MRCKb/, CDC42BPB, MSK1/RPS6KA5, MSK2/RPS6KA4, MSSK1/STK23, MST1/STK4, MST2/STK3, MST3/STK24, MST4, mTOR/FRAP1, MUSK, MYLK3, MYO3b, NEK1, NEK2, NEK3, NEK4, NEK6, NEK7, NEK9, NEK11, NIK/MAP3K14, NLK, OSR1/OXSR1, P38a/MAPK14, P38b/MAPK11, P38d/MAPK13, P38g/MAPK12, P70S6K/RPS6KB1, p70S6Kb/, RPS6KB2, PAK1, PAK2, PAK3, PAK4, PAK5, PAK6, PASK, PBK/TOPK, PDGFRa, PDGFRb, PDK1/PDPK1, PDK1/PDHK1, PDK2/PDHK2, PDK3/PDHK3, PDK4/PDHK4, PHKg1, PHKg2, PI3Ka, (p110a/p85a), PI3Kb, (p110b/p85a), PI3Kd, (p110d/p85a), PI3Kg(p120g), PIM1, PIM2, PIM3, PKA, PKAcb, PKAcg, PKCa, PKCb1, PKCb2, PKCd, PKCepsilon, PKCeta, PKCg, PKCiota, PKCmu/PRKD1, PKCnu/PRKD3, PKCtheta, PKCzeta, PKD2/PRKD2, PKG1a, PKG1b, PKG2/PRKG2, PKN1/PRK1, PKN2/PRK2, PKN3/PRK3, PLK1, PLK2, PLK3, PLK4/SAK, PRKX, PYK2, RAF1, RET, RIPK2, RIPK3, RIPK5, ROCK1, ROCK2, RON/MST1R, ROS/ROS1, RSK1, RSK2, RSK3, RSK4, SGK1, SGK2, SGK3/SGKL, SIK1, SIK2, SLK/STK2, SNARK/NUAK2, SRMS, SSTK/TSSK6, STK16, STK22D/TSSK1, STK25/YSK1, STK32b/YANK2, STK32c/YANK3, STK33, STK38/NDR1, STK38L/NDR2, STK39/STLK3, SRPK1, SRPK2, SYK, TAK1, TAOK1, TAOK2/TAO1, TAOK3/JIK, TBK1, TEC, TESK1, TGFBR2, TIE2/TEK, TLK1, TLK2, TNIK, TNK1, TRKA, TRKB, TRKC, TRPM7/CHAK1, TSSK2, TSSK3/STK22C, TTBK1, TTBK2, TTK, TXK, TYK1/LTK, TYK2, TYRO3/SKY, ULK1, ULK2, ULK3, VRK1, VRK2, WEE1, WNK1, WNK2, WNK3, YES/YES1, ZAK/MLTK, ZAP70, ZIPK/DAPK3, KINASE, MUTANTS, ABL1(E255K), ABL1(F317I), ABL1(G250E), ABL1(H396P), ABL1(M351T), ABL1(Q252H), ABL1(T315I), ABL1(Y253F), ALK (C1156Y), ALK(L1196M), ALK (F1174L), ALK (R1275Q), BRAF(V599E), BTK(E41K), CHK2(I157T), c-Kit(A829P), c-KIT(D816H), c-KIT(D816V), c-Kit(D820E), c-Kit(N822K), C-Kit (T670I), c-Kit(V559D), c-Kit(V559D/V654A), c-Kit(V559D/T670I), C-Kit (V560G), c-KIT(V654A), C-MET(D1228H), C-MET (D1228N), C-MET(F1200I), c-MET(M1250T), C-MET (Y1230A), C-MET(Y1230C), C-MET(Y1230D), C-MET (Y1230H), c-Src(T341M), EGFR(G719C), EGFR(G719S), EGFR(L858R), EGFR(L861Q), EGFR(T790M), EGFR, (L858R,T790M), EGFR(d746-750/T790M), EGFR(d746-750), EGFR(d747-749/A750P), EGFR(d747-752/P753S), EGFR(d752-759), FGFR1(V561M), FGFR2(N549H), FGFR3(G697C), FGFR3(K650E), FGFR3(K650M), FGFR4(N535K), FGFR4(V550E), FGFR4(V550L), FLT3 (D835Y), FLT3(ITD), JAK2 (V617F), LRRK2 (G2019S), LRRK2 (I2020T), LRRK2 (R1441C), p38a(T106M), PDGFRa(D842V), PDGFRa(T674I), PDGFRa(V561D), RET (E762Q), RET(G691S), RET(M918T), RET(R749T), RET (R813Q), RET(V804L), RET(V804M), RET(Y791F), TIF2 (R849W), TIF2(Y897S), and TIF2(Y1108F).

In another aspect of the invention, the subject compounds may be administered in combination with one or more targeted anti-cancer agents that modulate non-kinase biological targets, pathway, or processes. Such targets pathways, or processes include but not limited to heat shock proteins (e.g., HSP90), poly-ADP (adenosine diphosphate)-ribose polymerase (PARP), hypoxia-inducible factors (HIF), proteasome, Wnt/Hedgehog/Notch signaling proteins, TNF-alpha, matrix metalloproteinase, farnesyl transferase, apoptosis pathway (e.g., Bcl-xL, Bcl-2, Bcl-w), histone deacetylases (HDAC), histone acetyltransferases (HAT), and methyltransferase (e.g., histone lysine methyltransferases, histone arginine methyltransferase, DNA methyltransferase, etc.).

In another aspect of the invention, the compounds of the invention are administered in combination with one or more of other anti-cancer agents that include, but are not limited to, gene therapy, RNAi cancer therapy, chemoprotective agents (e.g., amfostine, mesna, and dexrazoxane), antibody conjugate (e.g., brentuximab vedotin, ibritumomab tioxetan), cancer immunotherapy such as Interleukin-2, cancer vaccines (e.g., sipuleucel-T) or monoclonal antibodies (e.g., Bevacizumab, Alemtuzumab, Rituximab, Trastuzumab, etc.).

In another aspect of the invention, the subject compounds are administered in combination with radiation therapy or surgeries. Radiation is commonly delivered internally (implantation of radioactive material near cancer site) or externally from a machine that employs photon (x-ray or gamma-ray) or particle radiation. Where the combination therapy further comprises radiation treatment, the radiation treatment may be conducted at any suitable time so long as a beneficial effect from the co-action of the combination of the therapeutic agents and radiation treatment is achieved. For example, in appropriate cases, the beneficial effect is still achieved when the radiation treatment is temporally removed from the administration of the therapeutic agents, perhaps by days or even weeks.

In certain embodiments, the compounds of the invention are administered in combination with one or more of radiation therapy, surgery, or anti-cancer agents that include, but are not limited to, DNA damaging agents, anti-metabolites, topoisomerase inhibitors, anti-microtubule agents, kinase inhibitors, epigenetic agents, HSP90 inhibitors, PARP inhibitors, and antibodies targeting VEGF, HER2, EGFR, CD50, CD20, CD30, CD33, etc.

In certain embodiments, the compounds of the invention are administered in combination with one or more of abarelix, abiraterone acetate, aldesleukin, alemtuzumab, altretamine, anastrozole, asparaginase, bendamustine, bevacizumab, bexarotene, bicalutamide, bleomycin, bortezombi, brentuximab vedotin, busulfan, capecitabine, carboplatin, carmustine, cetuximab, chlorambucil, cisplatin, cladribine, clofarabine, clomifene, crizotinib, cyclophosphamide, dasatinib, daunorubicin liposomal, decitabine, degarelix, denileukin diftitox, denileukin diftitox, denosumab, docetaxel, doxorubicin, doxorubicin liposomal, epirubicin, eribulin mesylate, erlotinib, estramustine, etoposide phosphate, everolimus, exemestane, fludarabine, fluorouracil, fotemustine, fulvestrant, gefitinib, gemcitabine, gemtuzumab ozogamicin, goserelin acetate, histrelin acetate, hydroxyurea, ibritumomab tiuxetan, idarubicin, ifosfamide, imatinib mesylate, interferon alfa 2a, ipilimumab, ixabepilone, lapatinib ditosylate, lenalidomide, letrozole, leucovorin, leuprolide acetate, levamisole, lomustine, mechlorethamine, melphalan, methotrexate, mitomycin C, mitoxantrone, nelarabine, nilotinib, oxaliplatin, paclitaxel, paclitaxel protein-bound particle, pamidronate, panitumumab, pegaspargase, peginterferon alfa-2b, pemetrexed disodium, pentostatin, raloxifene, rituximab, sorafenib, streptozocin, sunitinib maleate, tamoxifen, temsirolimus, teniposide, thalidomide, toremifene, tositumomab, trastuzumab, tretinoin, uramustine, vandetanib, vemurafenib, vinorelbine, zoledronate, radiation therapy, or surgery.

The invention further provides methods for the prevention or treatment of a neoplastic disease. In one embodiment, the invention relates to a method of treating a neoplastic disease, in a subject in need of treatment comprising administering to said subject a therapeutically effective amount of a compound of the invention. In one embodiment, the invention further provides for the use of a compound of the invention in the manufacture of a medicament for halting or decreasing a neoplastic disease.

In certain embodiments, the neoplastic disease is a lung cancer, head and neck cancer, central nervous system cancer, prostate cancer, testicular cancer, colorectal cancer, pancreatic cancer, liver cancer, stomach cancer, biliary tract cancer, esophageal cancer, gastrointestinal stromal tumor, breast cancer, cervical cancer, ovarian cancer, uterine cancer, leukemia, lymphomas, multiple myeloma, melanoma, basal cell carcinoma, squamous cell carcinoma, bladder cancer, renal cancer, sarcoma, mesothelioma, thymoma, myelodysplastic syndrome, or myeloproliferative disease.

It should be understood that the invention is not limited to the particular embodiments shown and described herein, but that various changes and modifications may be made without departing from the spirit and scope of the invention as defined by the claims.

The compounds according to the present invention may be synthesized according to a variety of reaction schemes. Necessary starting materials may be obtained by standard procedures of organic chemistry. The compounds and processes of the present invention will be better understood in connection with the following representative synthetic schemes and examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, and/or methods of the invention may be made without departing from the spirit of the invention and the scope of the appended claims.

A typical approach to synthesize of Formula (I) compounds

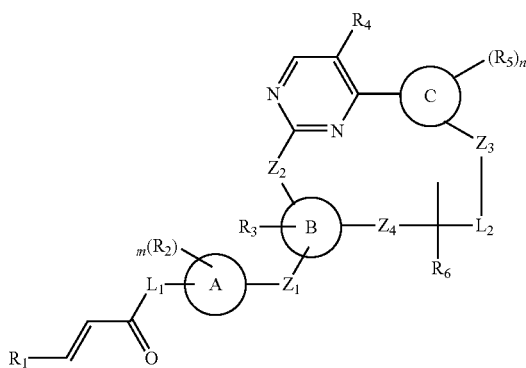

Formula (I)

in which $Z_1$ is CONH, $Z_2$ is NH, $L_2$ is —CH=CH—, and $R_6$ is attached to $Z_4$, is described in Scheme A. A, B, C, $R^1$, $R_1$, $R_2$, $R_3$, $R_4$, $R_5$, $R_6$, m, n, $Z_3$, $Z_4$, and $L_1$ in Scheme A are the same as those described in the Summary section above. This general procedure can be modified to produce other compounds of the invention with different values for $Z_1$, $Z_2$, $L_2$, and $R_6$ by appropriate modification of the reagents and starting materials used. A skilled addressee would readily be able to make these changes.

Scheme A

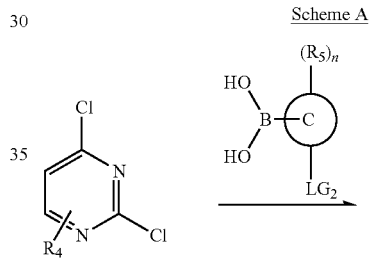

A-1

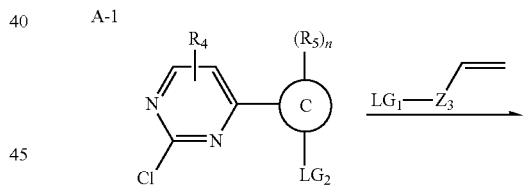

A-2

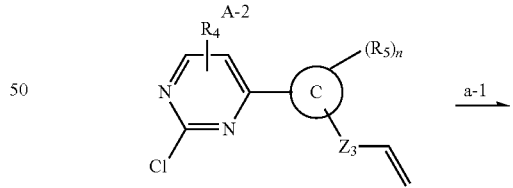

A-3

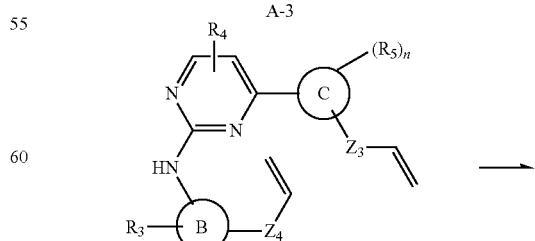

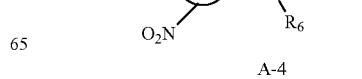

A-4

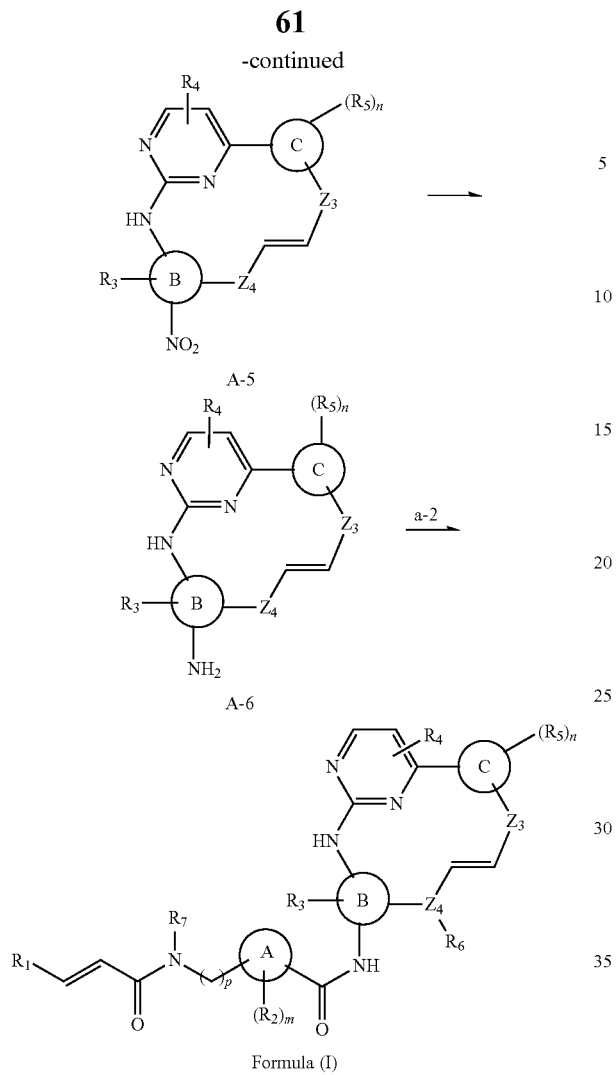

A-5 a-2 →

A-6

Formula (I)

As can be seen in Scheme A, an appropriately substituted 2,4-dichloropyrimidine (A-1) is treated under Suzuki coupling conditions with a suitably functionalized boronic acids of type to afford biaryl compounds of A-2, which on treatment with an appropriate alkene in the presence of a base such as Cs$_2$CO$_3$ to obtain A-3. Both the compound of A-2 and the alkene are functionalized with appropriate leaving group LG$_2$ and LG$_1$ groups respectively to produce the desired Z$_3$ group after reaction. Variation of the identity of the groups LG$_2$ and LG$_1$ easily allows for entry into the wide range of different Z$_3$ groups contemplated by the present invention. Substitution with an appropriately functionalized amine (a-1) under standard conditions affords terminal alkenes A-4, a key intermediate ready for ring closing metathesis (RCM). Once again, selection of the appropriately substituted amine (a-1) allows entry into a wide range of possible Z$_4$ groups contemplated by the present invention. Employing Grubbs 2$^{nd}$ generation catalyst RCM furnishes A-5 as a mixture of trans- and cis-isomers which can be separated by chromatography. After that, the nitro group of A-5 can be reduced to NH$_2$ group under standard conditions, which can couple with carboxylic acid a-2 to form the compounds of Formula (I).

The amine (a-1) in Scheme A

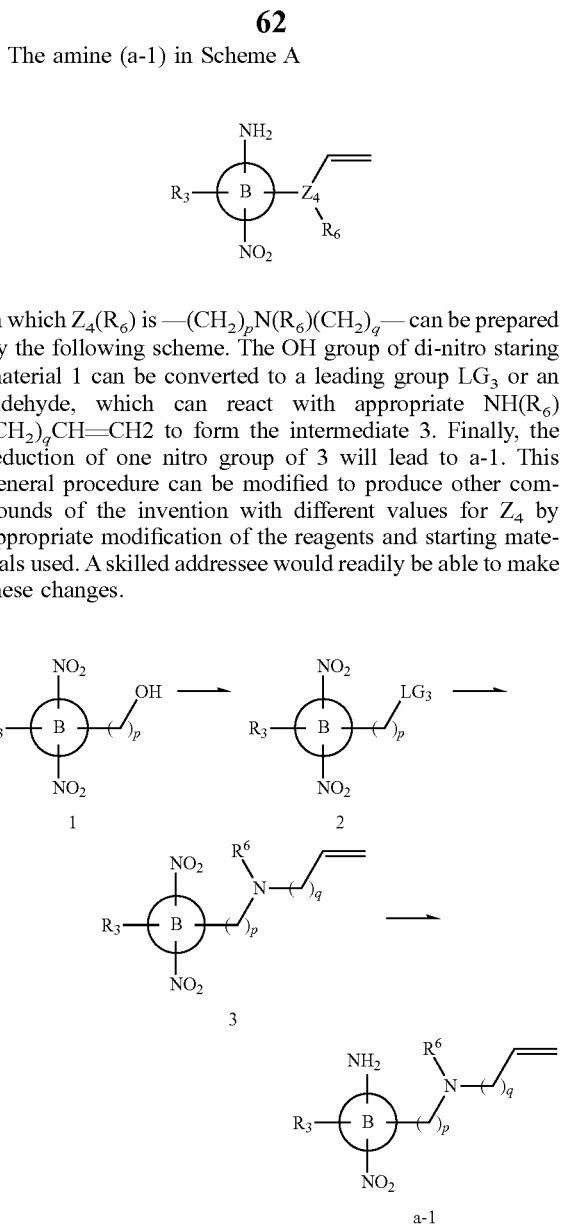

in which Z$_4$(R$_6$) is —(CH$_2$)$_p$N(R$_6$)(CH$_2$)$_q$— can be prepared by the following scheme. The OH group of di-nitro staring material 1 can be converted to a leading group LG$_3$ or an aldehyde, which can react with appropriate NH(R$_6$)(CH$_2$)$_q$CH=CH2 to form the intermediate 3. Finally, the reduction of one nitro group of 3 will lead to a-1. This general procedure can be modified to produce other compounds of the invention with different values for Z$_4$ by appropriate modification of the reagents and starting materials used. A skilled addressee would readily be able to make these changes.

The carboxylic acid a-2 in Scheme A can be prepared by the reaction of amino acid with appropriate acryloyl chloride, as shown the scheme below.

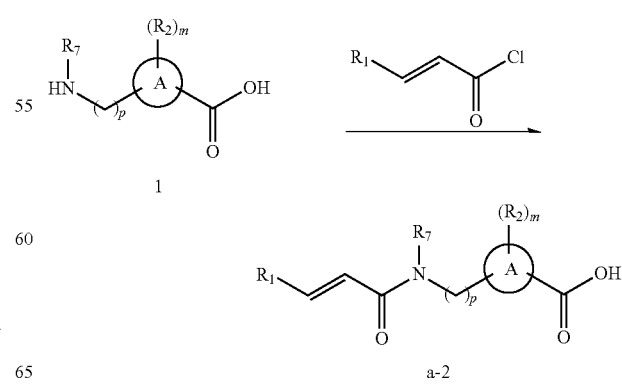

A typical approach to synthesize of Formula (II) compounds

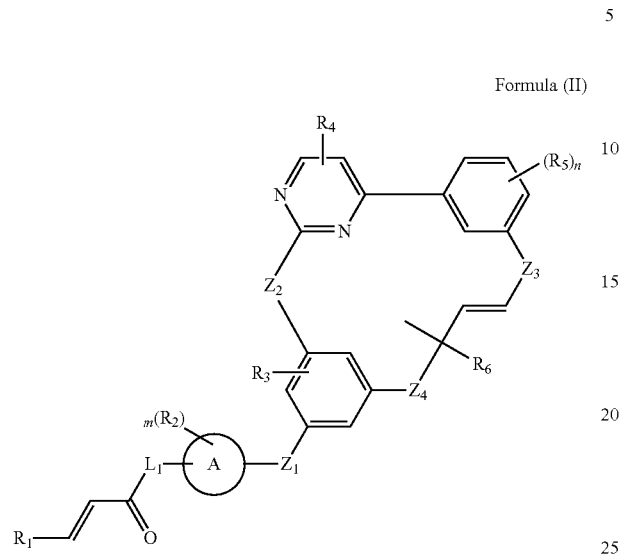

Formula (II)

in which $Z_1$ is CONH, $Z_2$ is NH, and $R_6$ is attached to $Z_4$, is described in Scheme B. A, $R_1$, $R_2$, $R_3$, $R_4$, $R_5$, $R_6$, m, n, $Z_3$, $Z_4$, and $L_1$, in Scheme A are the same as those described in the Summary section above. This general procedure can be modified to produce other compounds of the invention with different values for $Z_1$, $Z_2$, and $R_6$ by appropriate modification of the reagents and starting materials used. A skilled addressee would readily be able to make these changes.

Scheme B

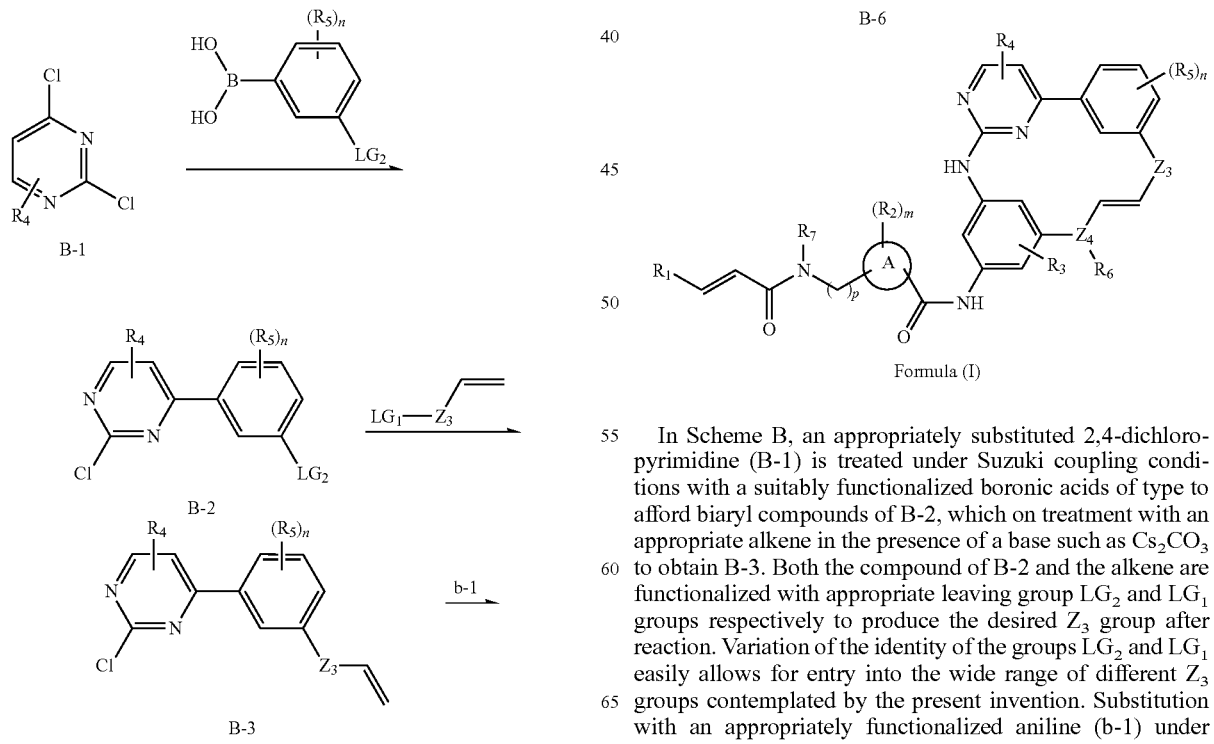

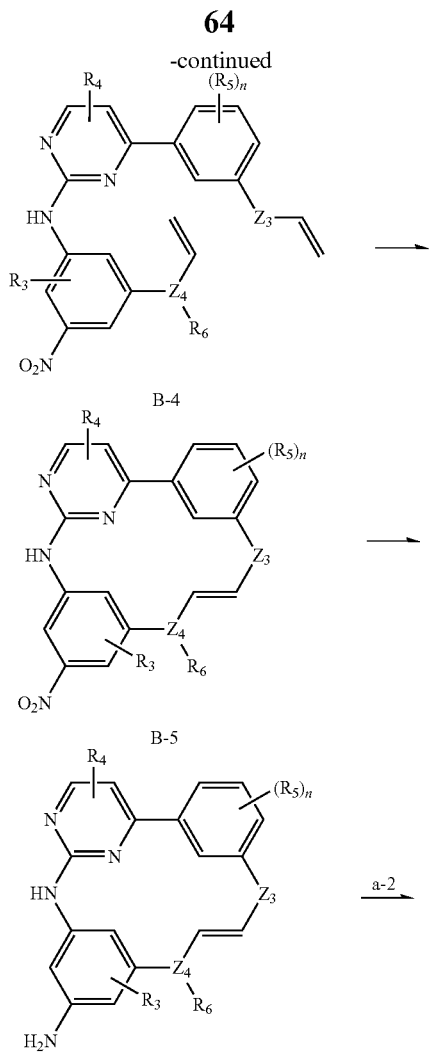

Formula (I)

In Scheme B, an appropriately substituted 2,4-dichloropyrimidine (B-1) is treated under Suzuki coupling conditions with a suitably functionalized boronic acids of type to afford biaryl compounds of B-2, which on treatment with an appropriate alkene in the presence of a base such as $Cs_2CO_3$ to obtain B-3. Both the compound of B-2 and the alkene are functionalized with appropriate leaving group $LG_2$ and $LG_1$ groups respectively to produce the desired $Z_3$ group after reaction. Variation of the identity of the groups $LG_2$ and $LG_1$ easily allows for entry into the wide range of different $Z_3$ groups contemplated by the present invention. Substitution with an appropriately functionalized aniline (b-1) under standard conditions affords terminal alkenes B-4, a key intermediate ready for ring closing metathesis (RCM). Once again selection of the appropriately substituted aniline (b-1) allows entry into a wide range of possible $Z_4$ groups contemplated by the present invention. Employing Grubbs $2^{nd}$ generation catalyst RCM furnishes B-5 as a mixture of trans- and cis-isomers which can be separated by chromatography. After that, the nitro group of B-5 can be reduced to $NH_2$ group under standard conditions, which can couple with carboxylic acid a-2 to form the compounds of Formula (II).

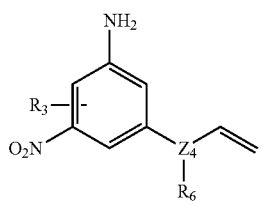

The aniline (b-1) in Scheme B in which $Z_4(R_6)$ is —$(CH_2)_p N(R_6)(CH_2)_q$— can be prepared by the following scheme. The OH group of di-nitro staring material 1 can be converted to a leading group $LG_3$ or an aldehyde, which can react with appropriate $NH(R_6)(CH_2)_q CH = CH2$ to form the intermediate 3. Finally, the reduction of one nitro group of 3 will lead to b-1. This general procedure can be modified to produce other compounds of the invention with different values for $Z_4$ by appropriate modification of the reagents and starting materials used. A skilled addressee would readily be able to make these changes.

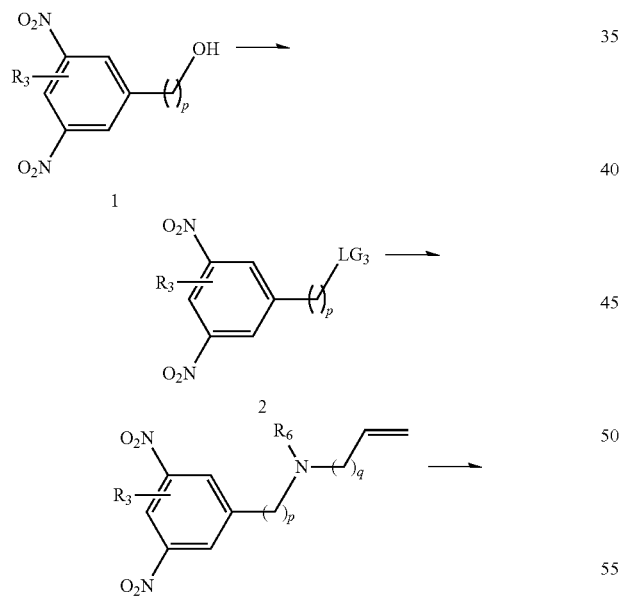

A typical approach to synthesize of Formula (III) compounds

Formula (III)

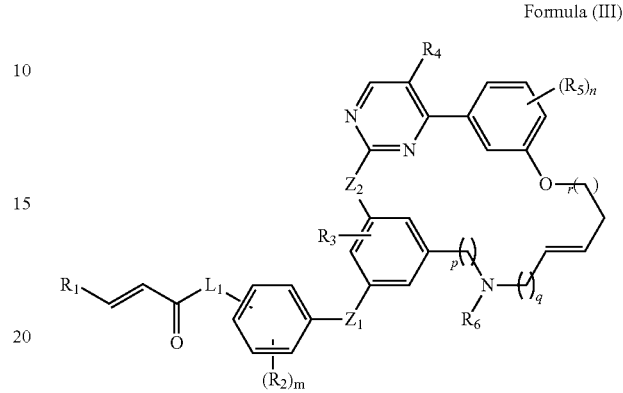

in which $Z_1$ is CONH, $Z_2$ is NH is described in Scheme C. $R_1$, $R_2$, $R_3$, $R_4$, $R_5$, $R_6$, m, n, p, q, r, and $L_1$ in Scheme C are the same as those described in the Summary section above. This general procedure can be modified to produce other compounds of the invention with different values for $Z_1$, and $Z_2$ by appropriate modification of the reagents and starting materials used. A skilled addressee would readily be able to make these changes.

Scheme C

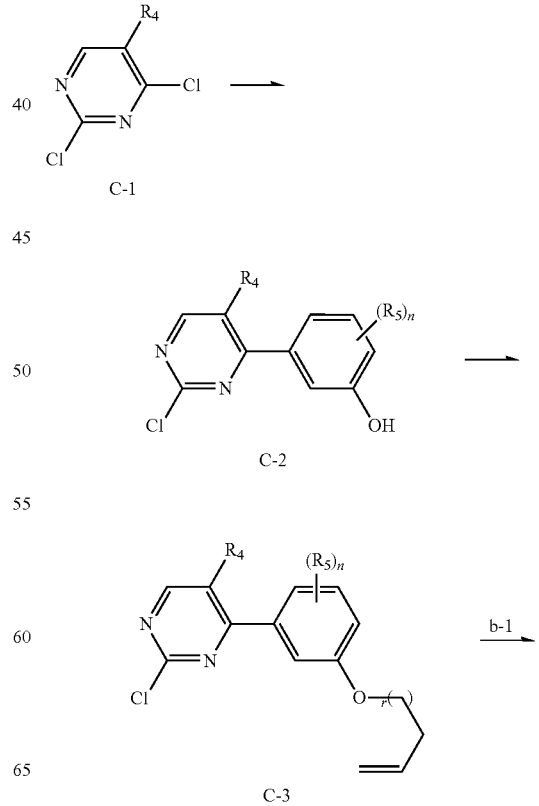

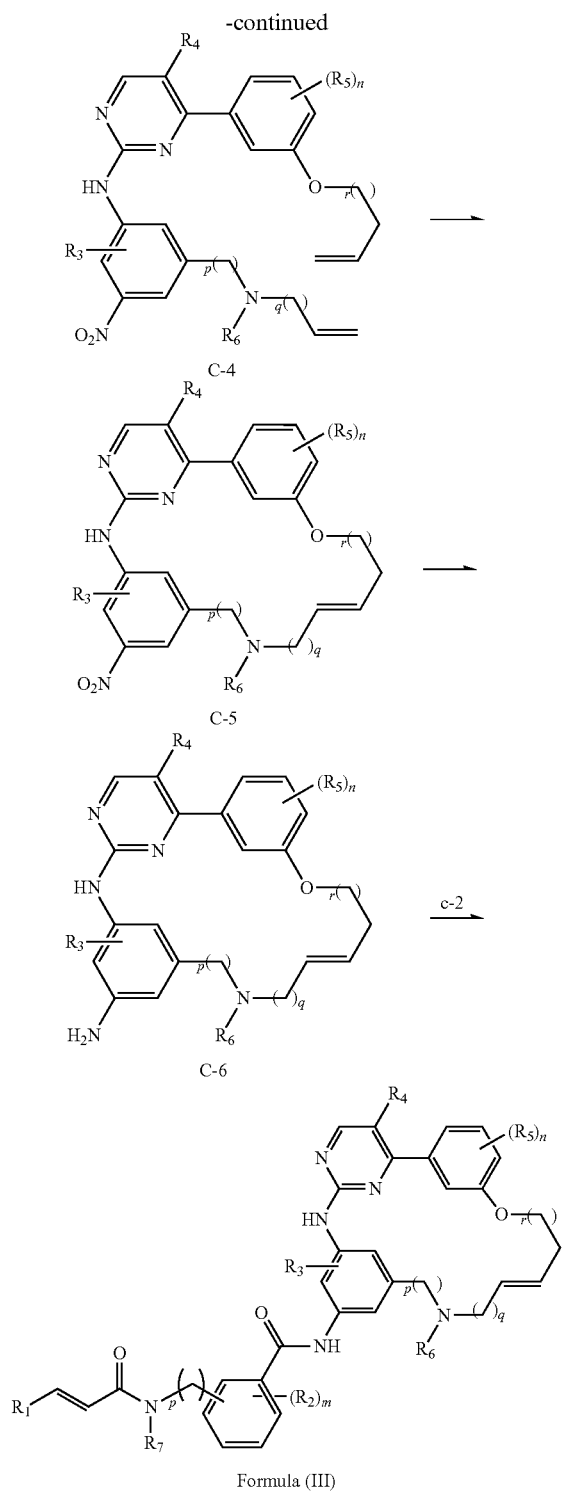

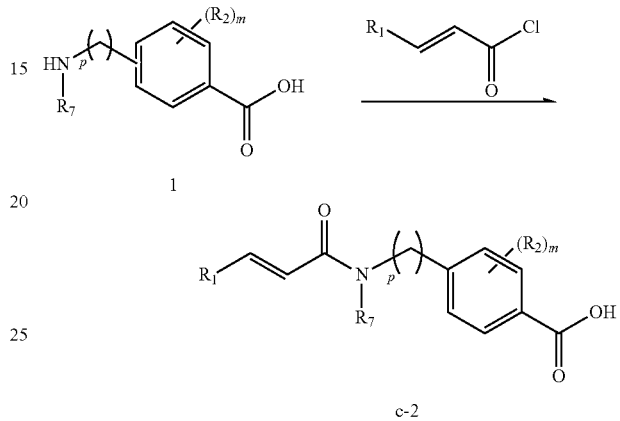

wide range of possible analogues contemplated by the present invention. Employing Grubbs $2^{nd}$ generation catalyst RCM furnishes C-5 as a mixture of trans- and cis-isomers which can be separated by chromatography. After that, the nitro group of C-5 can be reduced to $NH_2$ group under standard conditions, which can couple with carboxylic acid c-2 to form the compounds of Formula (III).

The carboxylic acid c-2 in in Scheme C can be prepared by the reaction of amino acid with appropriate acryloyl chloride, as shown the scheme below.

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

A typical approach to synthesize of the intermediate IM-16-(I) is described in Scheme I. $R_4$, $R_5$, n, and r in Scheme I are the same as those described in the Summary section above.

Scheme I

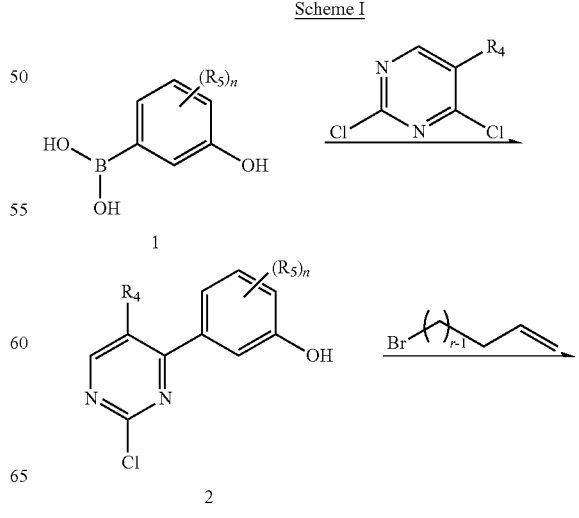

In Scheme C, an appropriately substituted 2,4-dichloropyrimidine (C-1) is treated under Suzuki coupling conditions with a suitably functionalized boronic acids of type to afford biaryl compounds of C-2, which on treatment with an appropriate alkenyl bromide in the presence of a base such as $Cs_2CO_3$ to obtain C-3. Substitution with an appropriately functionalized aniline (b-1) under standard conditions affords terminal alkenes C-4, a key intermediate ready for ring closing metathesis (RCM). Once again, selection of the appropriately substituted aniline (b-1) allows entry into a

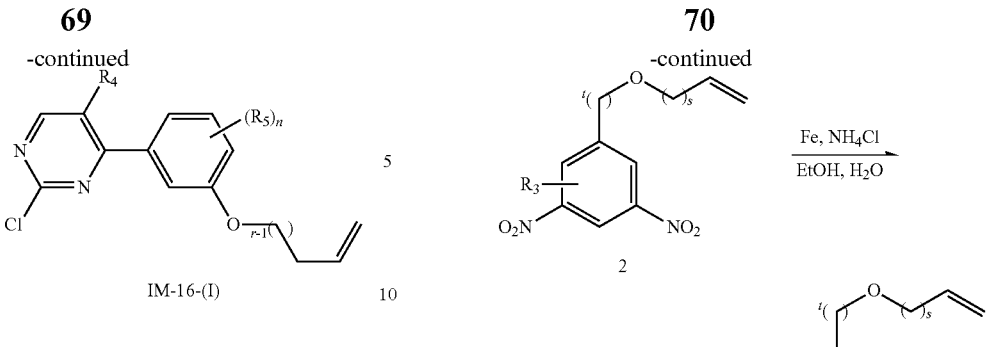

IM-16-(I)

In Scheme 1, an appropriately substituted 2,4-dichloropyrimidine is treated under Suzuki coupling conditions with a suitably functionalized boronic acids of type to afford biaryl compounds of 2, which on treatment with an appropriate alkene in the presence of a base such as $Cs_2CO_3$ to obtain IM-16-(I).

This general procedure of IM-16-(I) can be easily modified to produce other intermediates such as IM-16-(I)-1 and IM-16-(I)-2 by appropriate starting materials and modification of the reagents used. A skilled addressee would readily be able to make these changes. IM-16-(I)-1, and IM-16-(I)-2 are shown below:

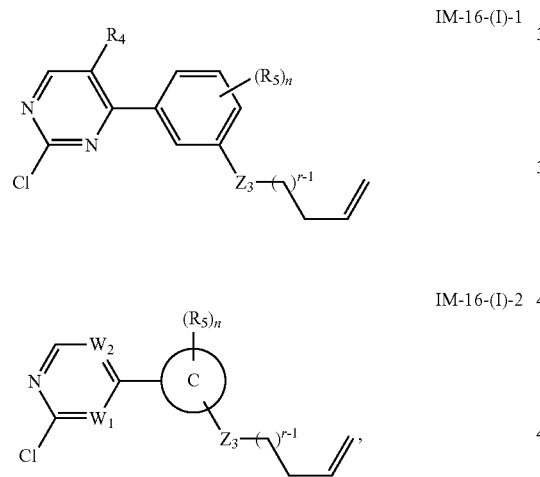

IM-16-(I)-1

IM-16-(I)-2 in which C, $R_5$, $R_4$, $Z_3$, $W_1$, $W_2$, n, r, and s are the same as those described in the Summary section above.

A typical approach to synthesize of the intermediate IM-16-(II)-1 is described in Scheme II-1. $R_3$, t, and s in Scheme 11-2 are the same as those described in the Summary section above.

Scheme II-1

In Scheme II-1, The OH group of di-nitro staring material 1 can react with appropriate $Br(CH_2)_sCH=CH2$ to form the intermediate 2, after that the reduction of nitro groups will lead to IM-16-(II)-1.

A typical approach to synthesize the intermediate IM-16-(II)-2 is described in Scheme II-2. $R_3$, t, and s in Scheme II are the same as those described in the Summary section above.

Scheme II-2

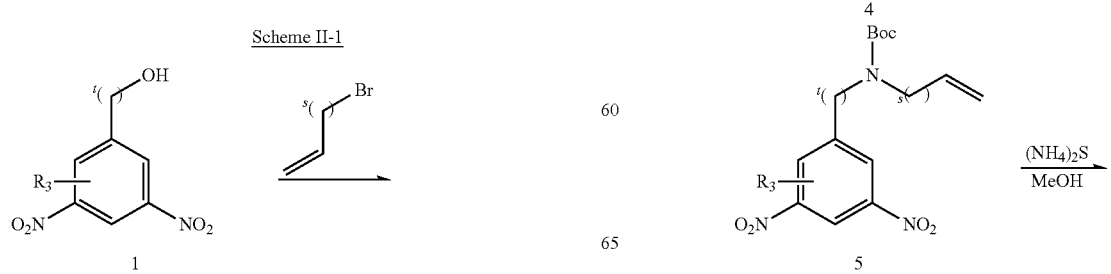

-continued

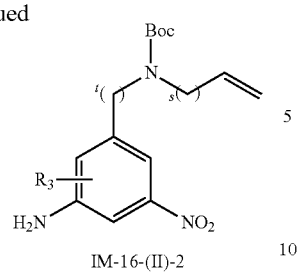

IM-16-(II)-2

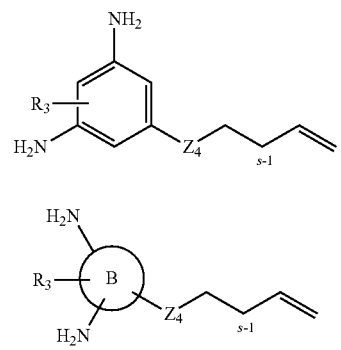

IM-16-(II)-4

IM-16-(II)-5

IM-16-(II)-6

In Scheme 11-2, The OH group of di-nitro staring material 1 can be oxidized to intermediate 2, which undergoes a reductive aminiation to form intermediate 4. After Boc protection, one of the nitro group of intermediate 4 can be reduced to form the intermediate IM-16-(II)-2.

A typical approach to synthesize the intermediate IM-16-(II)-3 is described in Scheme II-3. $R_3$, t, and s in Scheme 11-3 are the same as those described in the Summary section above.

Scheme 3

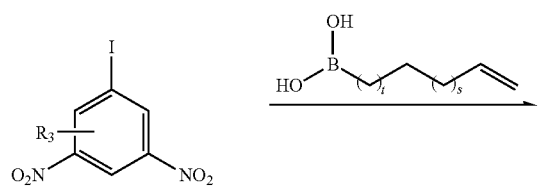

1

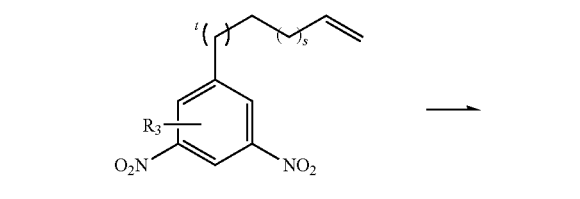

2

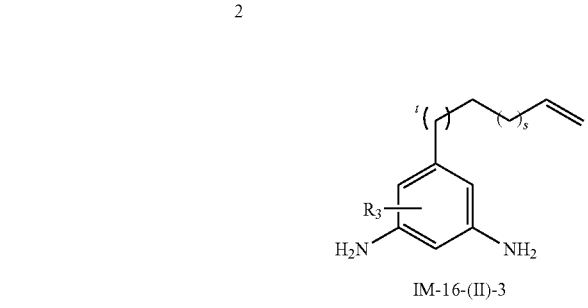

IM-16-(II)-3 in which B, $R_3$, $Z_4$, $Z_2$, and s are the same as those described in the Summary section above.

A typical approach to synthesize of the IM-16-(III)

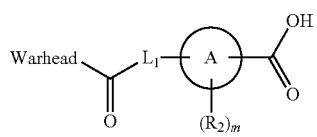

in which $L_1$ is $N(R_7)$ is described in Scheme III-1. $R_2$, A, m, and Warhead in Scheme III-1 are the same as those described in the Summary section above.

Scheme III-1

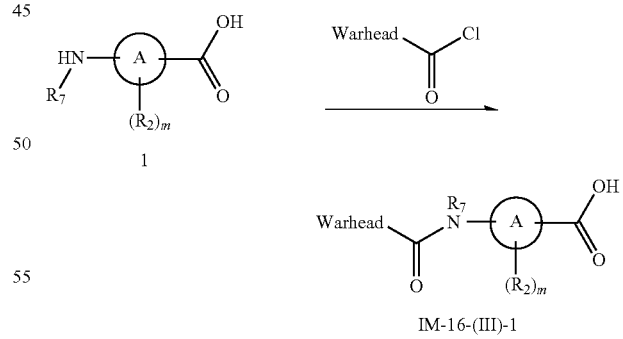

IM-16-(III)-1

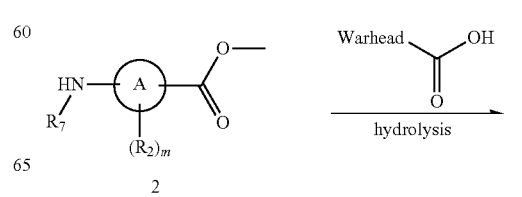

In Scheme 11-3, an appropriately substituted starting material 1 is treated under Suzuki coupling conditions with a suitably functionalized boronic acid to afford intermediate 2. After that, the nitro groups of 2 can be reduced to form the intermediate IM-16-(II)-3.

This general procedure of IM-16-(II)-1/2/3 can be used to produce other intermediates such as IM-16-(II)-4, IM-16-(II)-5, and IM-16-(II)-6 by appropriate starting materials and modification of the reagents used. A skilled addressee would be readily able to make these changes. IM-16-(II)-4, IM-16-(II)-5, and IM-16-(II)-6 are shown below:

-continued

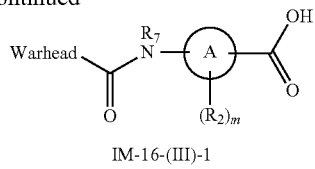

IM-16-(III)-1

In Scheme III-1, one step reaction of amine 1 and appropriate acyl chloride will lead to IM-16-(III)-1. Alternatively, the coupling of amine 1 and appropriate carboxylic acid followed by an ester hydrolysis will lead to IM-16-(III)-1.

Similarly, a typical approach to synthesize of the IM-16-(III)

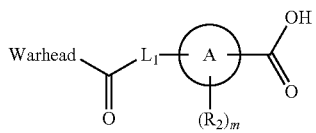

in which $L_1$ is a direct bond is described in Scheme H. $R_2$, $R_7$, A, m, and Warhead in Scheme 111-2 are the same as those described in the Summary section above.

Scheme III-2

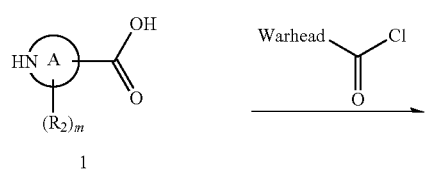

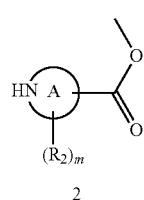

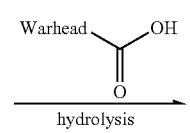

In Scheme 111-2, one step reaction of amine 1 and appropriate acyl chloride will lead to IM-16-(III)-2. Alternatively, the coupling of amine 2 and appropriate carboxylic acid followed by an ester hydrolysis will lead to IM-16-(III)-2.

This general procedure of IM-16-(III)-1 and IM-16-(III)-2 can be modified to produce other intermediates such as IM-16-(III)-3/4/5/6 by appropriate starting materials and modification of the reagents used. A skilled addressee would readily be able to make these changes. Similar intermediates are shown below:

IM-16-(III)-3

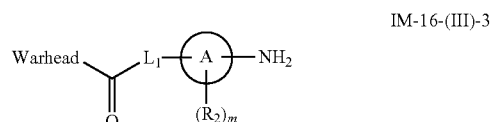

IM-16-(III)-4

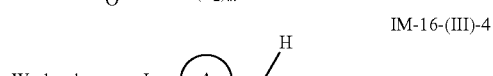

IM-16-(III)-5

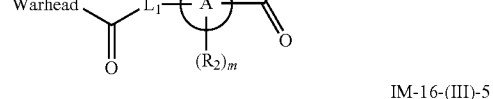

IM-16-(III)-6

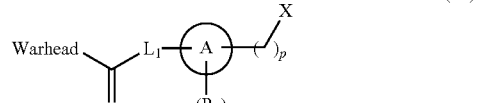

in which Warhead, $L_1$, A, $R_2$, p and m are the same as those described in the Summary section above.

A typical approach to synthesize of the IM-16-(IV) in which M is 0

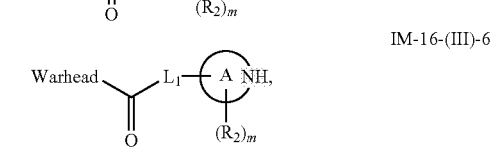

is described in Scheme IV. $R_3$, $R_4$, $R_5$, t, r, and s in Scheme H are the same as those described in the Summary section above.

Scheme IV

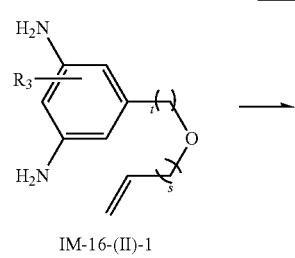

IM-16-(II)-1

-continued

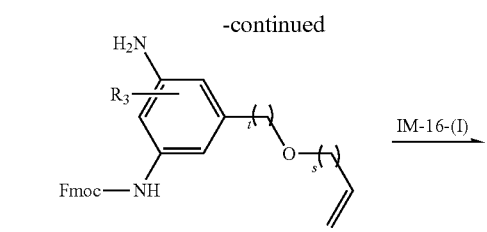

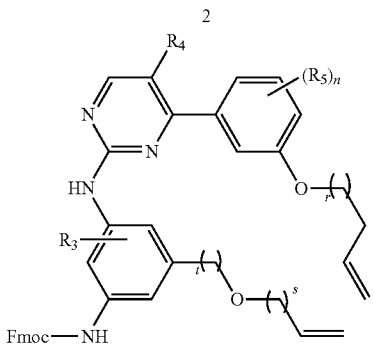

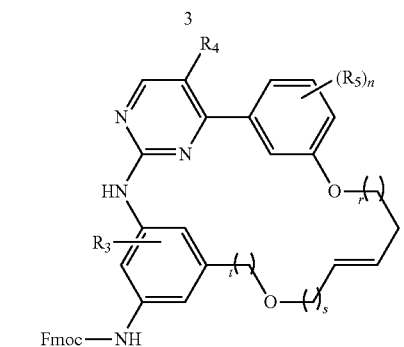

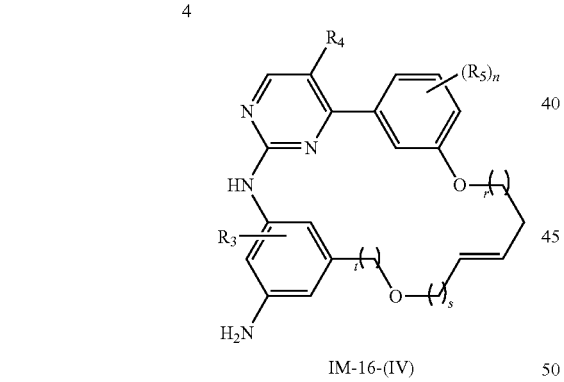

In Scheme IV, the starting material of IM-16-(II)-1 undergoes a Fmoc protection to form intermediate 2, followed by a substitution with IM-16-(I1)-1 under standard conditions affords terminal alkenes 3, a key intermediate ready for ring closing metathesis (RCM). Employing Grubbs $2^{nd}$ generation catalyst RCM furnishes 4 as a mixture of trans- and cis-isomers which can be separated by chromatography. After that, the de-protection of Fmoc of intermediate will lead to the key intermediate IM-16-(IV).

This general procedure of IM-16-(IV) can be modified to produce other similar intermediate with different values for M by using different starting materials such as IM-16-(II)-2 and IM-16-(II)-3 and appropriate modification of the reagents used. A skilled addressee would readily be able to make these changes.

Furthermore, as shown in the following scheme, IM-16-(IV) can be converted to other intermediate IM-16-(IV)-1 by standard organic reactions, in which X can be halo, —CHO, COOH, etc.

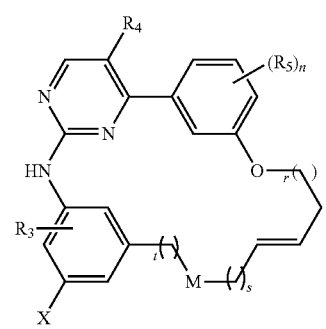

A typical approach to synthesize of Formula (III) compounds

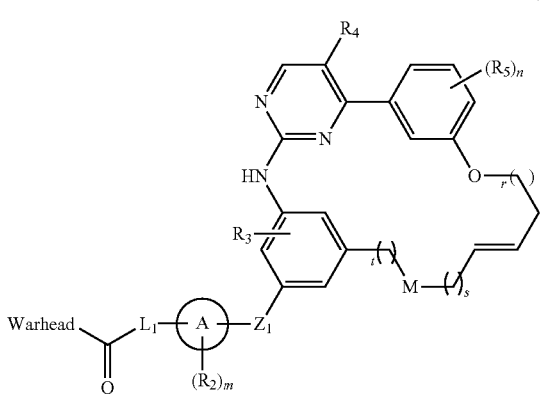

in which $Z_1$ is CONH is described in Scheme 1. $R_2$, $R_3$, $R_4$, $R_5$, m, n, s, t, r, and $L_1$ in Scheme 1 are the same as those described in the Summary section above.

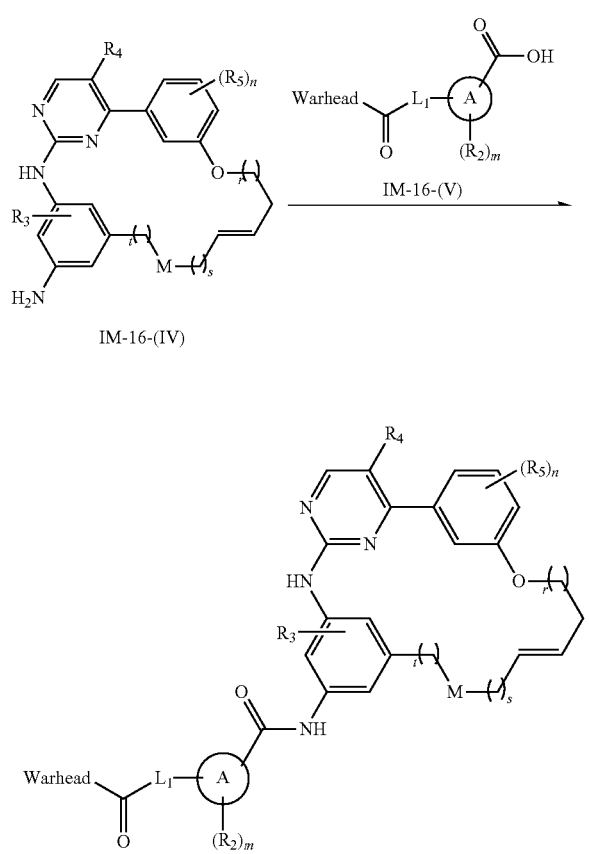

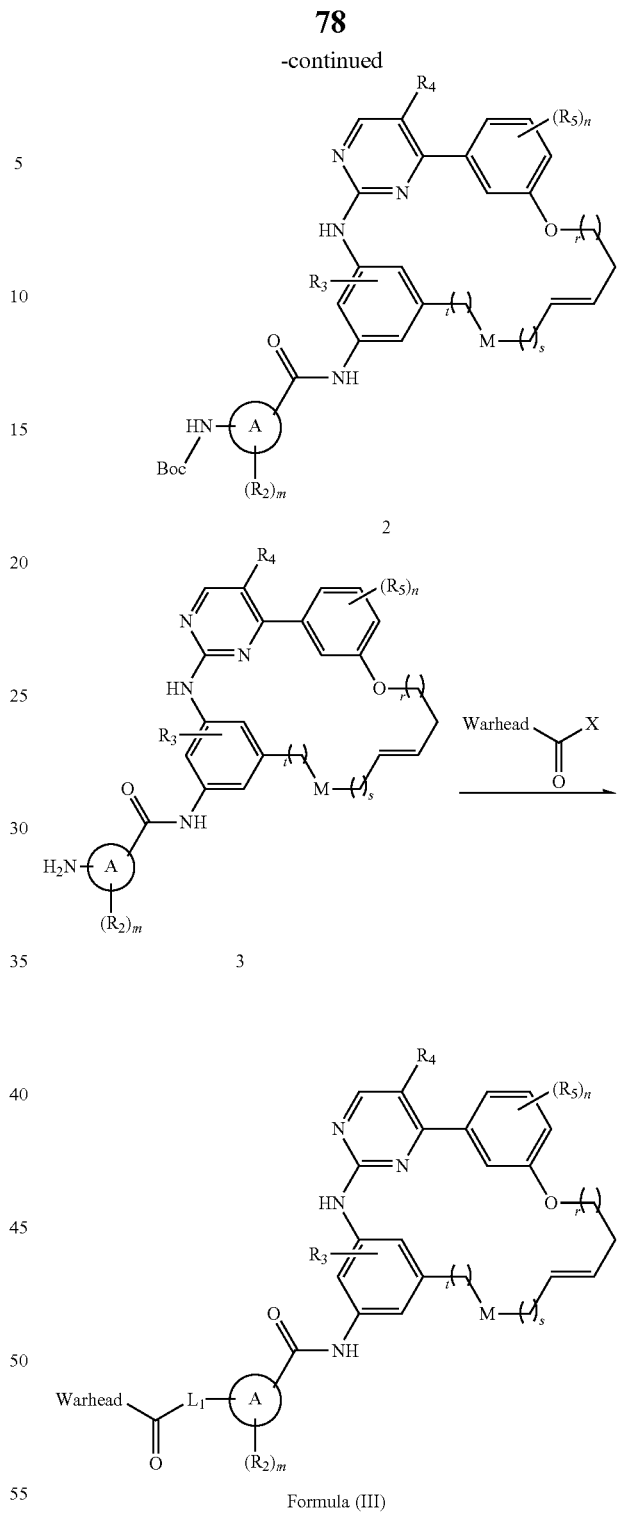

In Scheme 1, one step coupling reaction of IM-16-(IV) with IM-16-(III) will lead to the target molecules of Formula (III).

Alternatively, Formula (III) compounds in which $L_1$ is NH can be prepared by the Scheme 2 as shown below. $R_2$, $R_3$, $R_4$, $R_5$, m, n, s, t, and r in Scheme 2 are the same as those described in the Summary section above.

Scheme 2

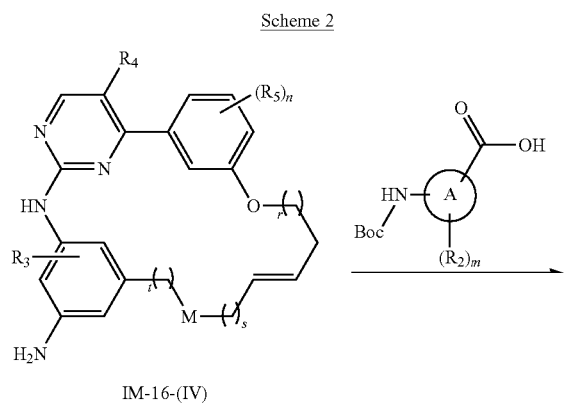

In Scheme 2, the coupling reaction of IM-16-(IV) with appropriate carboxylic acid will afford intermediate 2, which can be de-protected to form the amine intermediate 3. Finally, 3 can react with appropriate acyl chloride or carboxylic acid to form the Formulation (III) compounds.

Alternatively, Formula (III) compounds in which $L_1$ is a direct bond can be prepared by the Scheme 3 as shown below. $R_2$, $R_3$, $R_4$, $R_5$, m, n, s, t, and r in Scheme 3 are the same as those described in the Summary section above

Scheme 3

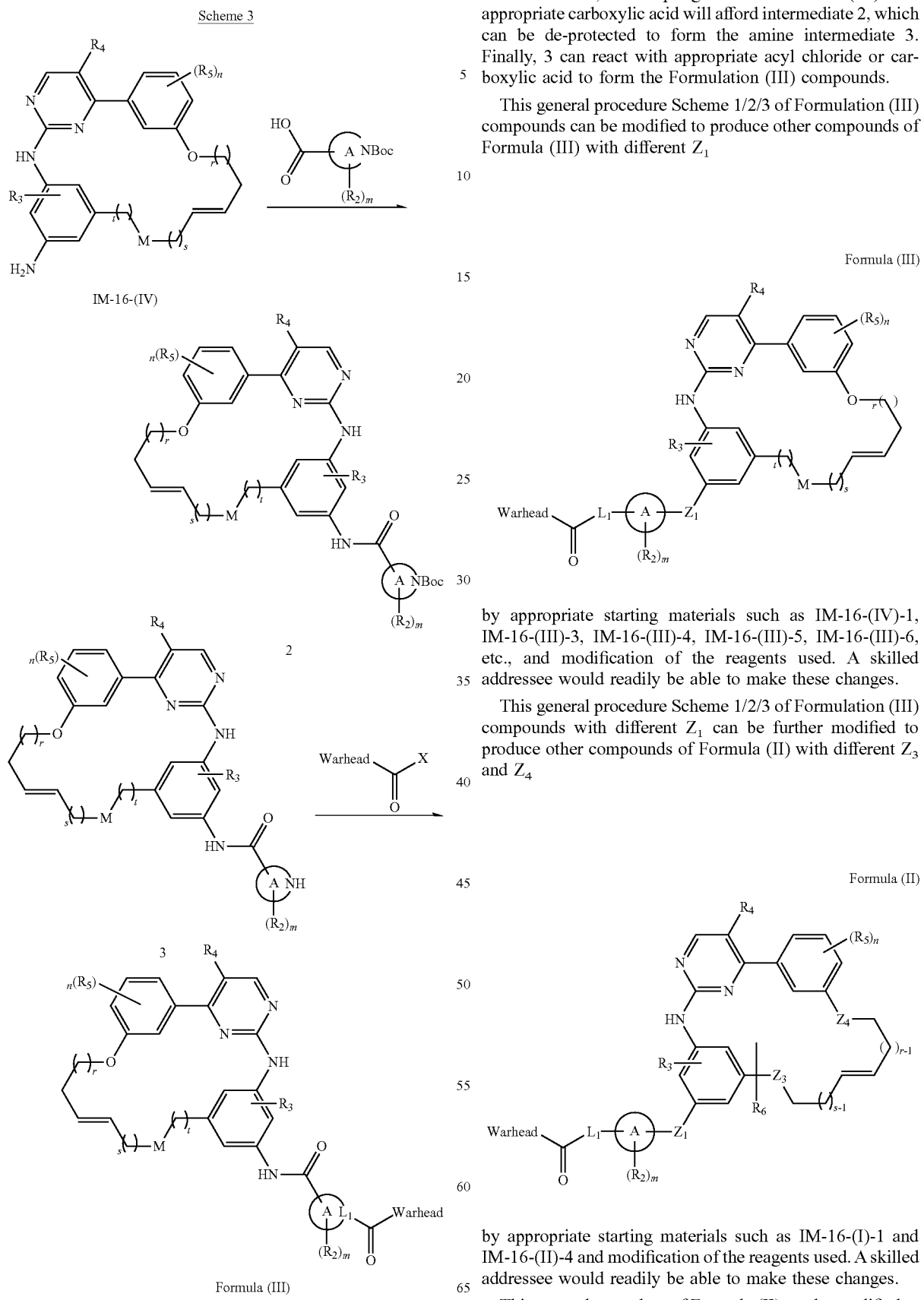

In Scheme 3, the coupling reaction of IM-16-(IV) with appropriate carboxylic acid will afford intermediate 2, which can be de-protected to form the amine intermediate 3. Finally, 3 can react with appropriate acyl chloride or carboxylic acid to form the Formulation (III) compounds.

This general procedure Scheme 1/2/3 of Formulation (III) compounds can be modified to produce other compounds of Formula (III) with different $Z_1$ by appropriate starting materials such as IM-16-(IV)-1, IM-16-(III)-3, IM-16-(III)-4, IM-16-(III)-5, IM-16-(III)-6, etc., and modification of the reagents used. A skilled addressee would readily be able to make these changes.

This general procedure Scheme 1/2/3 of Formulation (III) compounds with different $Z_1$ can be further modified to produce other compounds of Formula (II) with different $Z_3$ and $Z_4$ by appropriate starting materials such as IM-16-(I)-1 and IM-16-(II)-4 and modification of the reagents used. A skilled addressee would readily be able to make these changes.

This general procedure of Formula (II) can be modified to produce other compounds of Formula (I)

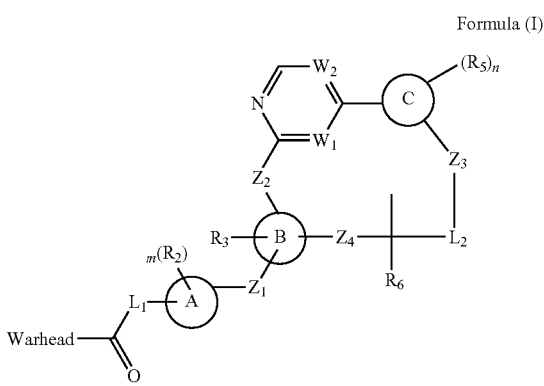

Formula (I)

with different $L_2$, B, C, $Z_3$ and $Z_4$ by appropriate starting materials such as IM-16-(I)-2 and IM-16-(II)-5/6 and modification of the reagents used. A skilled addressee would readily be able to make these changes.

Where NMR data are presented, $^1$H spectra were obtained on XL400 (400 MHz) and are reported as ppm down field from Me$_4$Si with number of protons, multiplicities, and coupling constants in Hertz indicated parenthetically. Where HPLC data are presented, analyses were performed using an Agilent 1100 system. Where LC/MS data are presented, analyses were performed using an Applied Biosystems API-100 mass spectrometer and Shimadzu SCL-10A LC column.

Synthesis Example 1: Preparation of Intermediate 4 (IM-16-1)

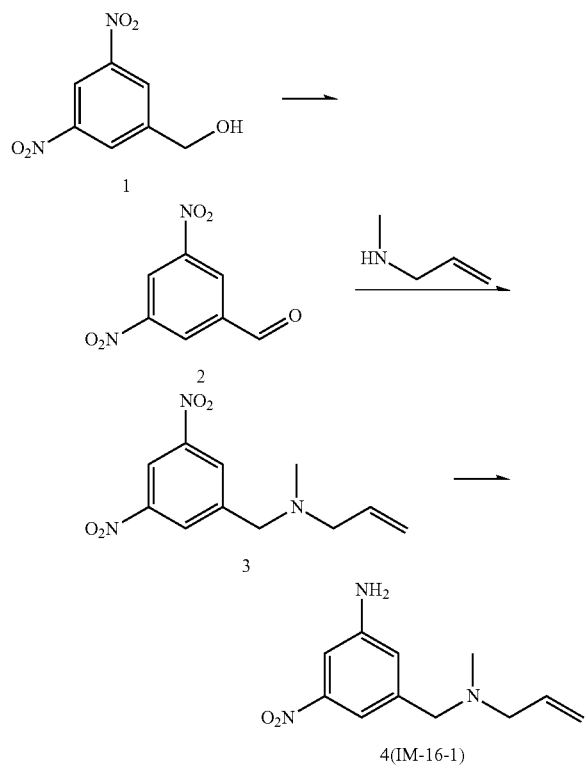

Step 1: an oven dried 250 mL round bottom flask that was dried under nitrogen with a magnetic stir bar was charged with 10 mmol of 3,5-dinitrobenzyl alcohol and 25 mL of freshly distilled (over calcium hydride) dichloromethane was added. The mixture was allowed to stir at room temperature under nitrogen until most of the alcohol was dissolved. Subsequently, 16 mmol of pyridinium chlorochromate was added rapidly to the flask and an additional 25 mL of freshly distilled dichloromethane was also transferred to the reaction mixture. The flask was placed under nitrogen and was allowed to stir vigorously at room temperature overnight. After the reaction mixture was allowed to stir overnight, the flask was observed to contain a large amount of brown to black precipitate on the sides of the flask. At this time a TLC (1:1 EtOAc:hexanes) was taken of the crude mixture. The reaction mixture was then removed from stirring and its contents were vacuum filtered over 1-2 inches of silica gel (pre-eluted with ~5-10 mL of anhydrous diethyl ether) with 100 mL of diethyl ether into a clean oven dried 250 mL round bottom flask. The tan brown crude mixture was rotary evaporated and dried under house vacuum to yield a powder like light brown intermediate 2. Yield 53%. $^1$H NMR (400 MHz, CDCl$_3$, δ ppm): 10.23 ppm, 1H, s, (J=4.0 Hz), 9.31 ppm, 1H, t, (J=4.0 Hz), 9.06 ppm, 2H, d, (J=4.0 Hz); $^{13}$C NMR (400 MHz, CDCl$_3$, δ ppm): 187.4 ppm, 149.4 ppm, 138.7 ppm, 128.9 ppm, 123.5 ppm; [MH]$^+$=197.

Step 2: To solution of intermediate 2 (10 mmol) in CH$_2$Cl$_2$ (60 mL) was added N-methyl allyl amine (12.4 mmol), the reaction mixture was stirred for 2 h. Na(OAc)$_3$BH (20 mmol) was then added portionwise over 5 mins. The resulting mixture was stirred at ambient temperature overnight and then quenched with saturated NH$_4$Cl. The product was extracted with CH$_2$Cl$_2$ thrice and the combined organic extracts were washed brine, dried over Na$_2$SO4 and concentrated under reduced pressure. The crude mixture was column purified (EtOAc/Hexane) to furnish form intermediate 3. [MH]$^+$=252. $^1$H NMR (400 MHz, CDCl$_3$) δ 8.93 (t, J=1.9 Hz, 1H), 8.56 (d, J=1.8 Hz, 2H), 5.91 (ddt, J=16.8, 10.2, 6.4 Hz, 1H), 5.30-5.18 (m, 2H), 3.71 (s, 2H), 3.12 (d, J=6.4 Hz, 2H), 2.25 (s, 3H).

Step 3: To a solution of intermediate 3 (1.2 mmol) in MeOH/CH$_2$Cl$_2$ (1:1, 10 mL) at ambient temperature was added SnCl$_2$.2H$_2$O (3.6 mmol) and the resulting mixture was stirred overnight. The reaction mixture was cooled to 0° C. and quenched with saturated Na$_2$CO$_3$. The product was extracted with CH$_2$Cl$_2$ thrice and the combined organic extracts were washed with H$_2$O followed by brine, dried over Na$_2$SO$_4$ and concentrated under reduced pressure to furnish an oil, which was purified by column chromatography (EtOAc/Hexane) to obtain intermediate 4, [MH]$^+$=222, $^1$H NMR (400 MHz, CD$_3$Cl): δ 2.197 (s, 3H), 3.044 (d, 2H), 3.459 (s, 2H), 3.965 (s, 2H), 5.164-5.239 (m, 2H), 5.845-5.946 (m, 1H), 6.978 (s, 1H), 7.378 (t, 1H), 7.540 (s, 1H).

Synthesis Example 2: Preparation of Intermediate IM-16-1-Boc

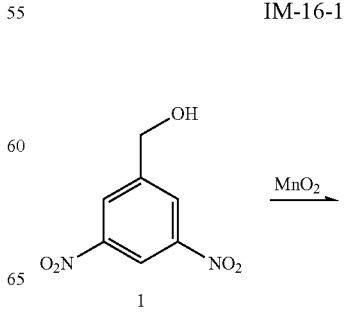

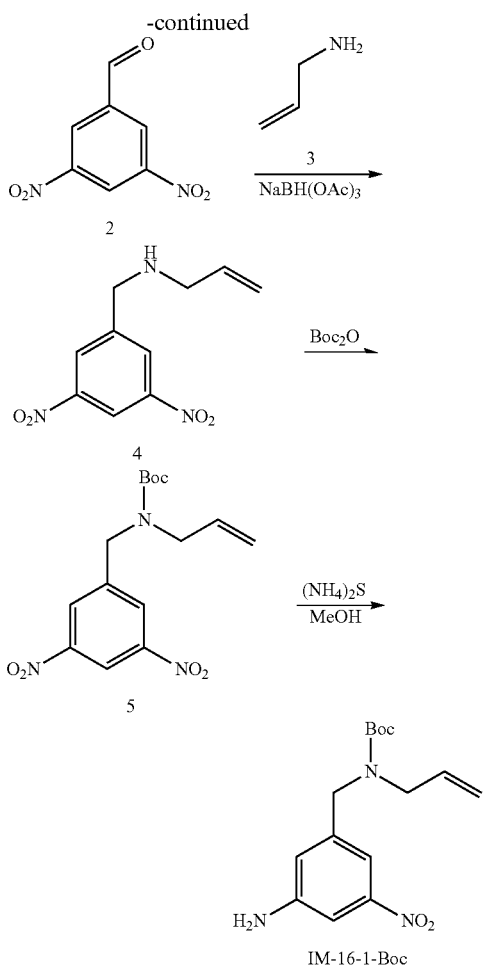

To a solution of compound 1(150.0 g, 2 mol) in DCM (7.0 L) was added MnO₂ (4.0 kg, 46.0 mol, 22.8 eq), the reaction was stirred at 46° C. for 36 hrs. TLC showed compound 1 (DCM:MeOH=10:1, $R_f$=0.35) was consumed completely and two main spots (DCM: MeOH=10:1, $R_f$=0.1, $R_f$=0.89) was detected. The reaction mixture was filtered and washed with DCM (4 L, four times). After that, the filter was concentrated. The residue was diluted with NaOH (1 L, 1M) and extracted with DCM (2 L), and the combined organic layers were washed with brine (800 mL), dried over Na₂SO₄, filtered and concentrated under reduced pressure to give the product 1. Then alkaline solutions was adjust pH to 6 by addition HCl (1M) and extracted with DCM (2 L), washed with brine (800 mL), dried over Na₂SO₄, filtered and concentrated under reduced pressure to give compound 2. Afforded compound 2 (150.0 g, 764.8 mmol, 37.9% yield) as a yellow solid. ¹H NMR: EW3684-1-P1D 400 MHz CDCl₃ δ10.23 (s, 1H), 9.29 (s, 1H), 9.05 (d, J=2 Hz, 2H)

To a solution of compound 2 (130.0 g, 662.9 mmol, 1.0 eq) in DCM (800.0 mL) was added compound 3 (54.6 g, 957.1 mmol, 71.9 mL, 1.4 eq) and NaBH(OAc)₃ (351.2 g, 1.7 mol, 2.5 eq) then stirred at 25° C. for 16 hrs. TLC showed compound 2 (PE:EA=5:1, $R_f$=0.85) was consumed completely and the desired compound (PE:EA=5:1, $R_f$=0.3, the control spot was from EW3684-3-P1) was detected. The reaction mixture was quenched by addition water (1 L), and then adjusted pH to 8 by addition NaHCO₃ and extracted with DCM (1500 mL). The combined organic layers were washed with brine (700 mL), dried over Na₂SO₄, filtered and concentrated under reduced pressure to give compound 4 (181.0 g, crude) an oil. And the oil was used for nest step.

To a solution of compound 4 (167.0 g, 563.2 mmol, 1.0 eq) in DCM (2.0 L) was added TEA (62.7 g, 619.5 mmol, 85.9 mL, 1.1 eq) and Boc2O (135.2 g, 619.5 mmol, 142.3 mL, 1.1 eq), the reaction was stirred at 25° C. for 16 hrs. TLC showed compound 4 (PE:EA=5:1, $R_f$=0.3) was consumed completely and the desired compound 5 (PE:EA=5:1, $R_f$=0.87) was detected. The reaction mixture was partitioned between water (2 L) and DCM (4 L). The organic phase was separated, washed with brine (1 L), dried over Na₂SO₄, filtered and concentrated under reduced pressure to give a residue. The residue was purified by column chromatography (SiO₂, PE:EA=20:1 to 15:1, PE:EA=20:1, $R_f$=0.15) afforded compound 5 (174.0 g, 515.8 mmol, 91.6% yield) as a yellow oil. ¹H NMR: EW3684-8-P1A 400 MHz DMSO-d₆ δ 8.74 (s, 1H), 8.51 (s, 2H), 5.83-5.73 (m, 1H), 5.13 (d, J=10.4 Hz, 2H), 4.59 (s, 2H), 3.88 (s, 2H), 1.42 (m, 9H)

To a solution of compound 5 (174.0 g, 515.8 mmol, 1.0 eq) in MeOH (1.3 L) was added (NH₄)₂S/H₂O (390.1 g, 5.7 mol, 390.1 mL, 11.1 eq, V/V=40%~48%), the reaction was stirred at 65° C. for 5 hrs. TLC showed almost of compound 5 (PE:EA=5:1, $R_f$=0.87) was consumed and IM-16-1 (PE: EA=5:1, $R_f$=0.75) was detected. The reaction mixture was filtered and washed with MeOH (500 mL), and then the filter was concentrated. The residue with EW3684-9-P1 were purified by column chromatography (SiO₂, PE:EA=2:1 to 15:1) together (PE:EA=20:1, $R_f$=0.15). Afforded IM-16-1 (102.0 g, 323.6 mmol, 62.73% yield, 97.5% purity) as a yellow liquid. And there were two batches, batch 1 (75.0 g) and batch 2 (27.0 g). ¹H NMR: EW3684-9-P1A 400 MHz DMSO-d₆ δ 7.28 (t, J=2.1 Hz, 1H), 7.19 (s, 1H), 6.81 (s, 1H), 5.86 (s, 2H), 5.81-5.70 (m, 1H), 5.13 (d, J=10.2 Hz, 2H), 4.29 (br. s., 2H), 3.77 (d, J=18.9 Hz, 2H), 1.42 (d, J=12.5 Hz, 9H). ¹H NMR: EW3684-9-P1B 400 MHz DMSO-d₆ δ 7.32-7.09 (m, 2H), 6.81 (s, 1H), 5.90-5.69 (m, 3H), 5.20-4.99 (m, 2H), 4.30 (br. s., 2H), 3.78 (d, J=12.0 Hz, 2H), 1.52-1.26 (m, 9H).

Synthesis Example 3: Preparation of Intermediate 7 (IM-16-2)

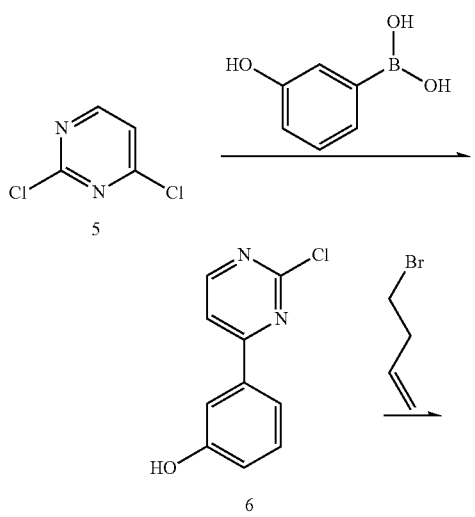

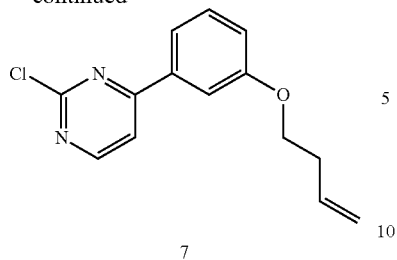

7

Step 1: to a degassed solution of 2,4-dichloropyrimidine (7 mmol) and (3-hydroxyphenyl)boronic acid (8 mmol) in 1,2 dimethoxy ethane (10 mL) was added sequentially, aqueous $Na_2CO_3$ (10 mmol) and $Pd(PPh_3)_4$ (0.335 mmol). The resultant mixture was stirred at 80-85° C. for 4 h, cooled to 0° C. and quenched with saturated aqueous $NH_4Cl$ solution. The product was extracted with $CH_2Cl_2$ thrice and the combined organic extracts were washed with brine, dried over $Na_2SO_4$ and concentrated under reduced pressure. The crude mixture was column purified (EtOAc/Hexane) to obtain 0.45g of intermediate 5. $^1H$ NMR (400 MHz, $CDCl_3$): δ 9.74 (s, 1H), 9.23 (d, 1H), 8.83 (d, 1H), 8.01 (dd, 1H), 7.60-7.65 (m, 1H), 7.35 (t, 1H), 6.94-6.99 (m, 1H). MS (m/z): 207 $[MH]^+$.

Step 2: to a mixture of intermediate 5 (10 mmol) and 4-bromobut-1-ene (6 mmol) in dry DMF (10 mL) at ambient temperature was added Cesium carbonate (44 mmol) and the resulting mixture was stirred at 40° C. for 6 h. The reaction mixture was cooled to 0° C. and quenched with $H_2O$. The product was extracted with $CH_2Cl_2$ thrice and the combined organic extracts were washed with $H_2O$ followed by brine, dried over $Na_2SO_4$ and concentrated under reduced pressure to furnish an oil, which was purified by column (EtOAc/Hexane) to obtain 1.6g of intermediate 7. $^1H$ NMR (400 MHz, DMSO $d_6$): δ 8.82 (d, 1H), 8.12 (d, 1H), 7.77 (d, 1H), 7.70 (br s, 1H), 7.48 (t, J=8.0 Hz, 1H), 7.18 (dd, 1H), 5.86-5.98 (m, 1H), 5.16-5.24 (m, 1H), 5.09-5.13 (m, 1H), 4.13 (t, 2H), 2.49-2.56 (m, 2H). MS (m/z): 261 $[MH]^+$.

Synthesis Example 4: Preparation of IM-16-3

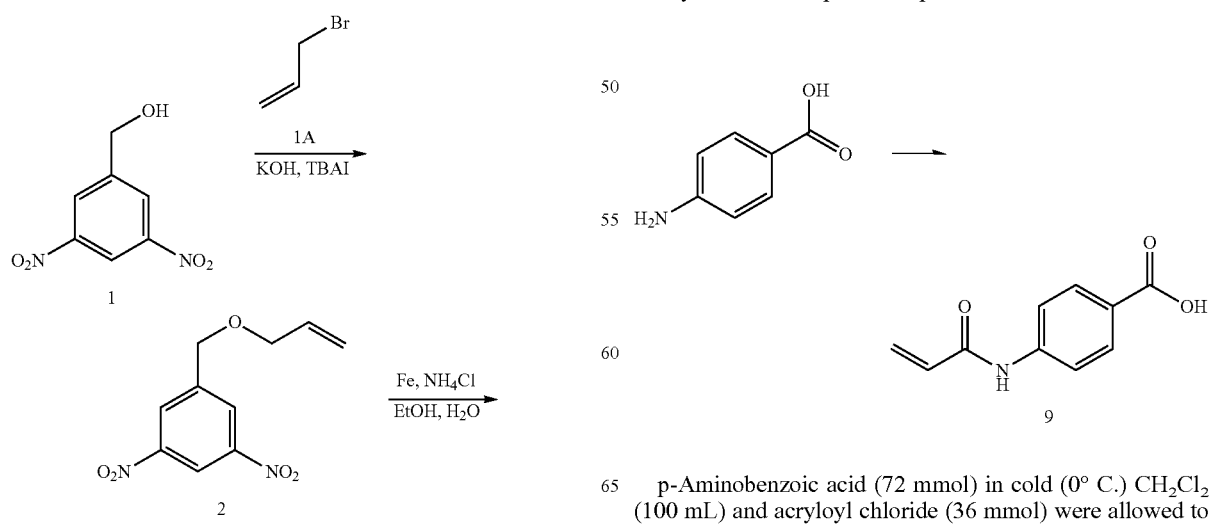

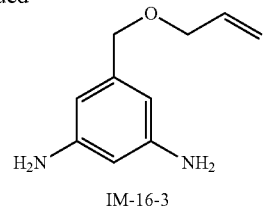

IM-16-3

To a solution of compound 1 (150 g, 749 mmol, 1.00 eq) was added $Bu_4NI$ (14.6 g, 37.5 mmol, 0.05 eq) and KOH (106 g, 1.87 mol, 2.50 eq). After addition, then 3-bromoprop-1-ene (750 mL) was added dropwise at −78° C. The mixture was stirred at 15° C. for 12 hrs. TLC (petroleum ether/ethyl acetate=5/1, Rf-p=0.54) indicated ~0% of Reactant 1 was remained. Two reactions were combined to purify. The reaction mixture was purified by column chromatography ($SiO_2$, Petroleum ether/Ethyl acetate=100/1 to 10:1, Rf-p=0.54) to give compound 2 (180.00 g, 680.10 mmol, 90% purity) as a yellow oil. $^1H$ NMR: 400 MHz $CDCl_3$, δ 8.92 (s, 1H), 8.52 (d, J=1.76 Hz, 2H), 5.88-6.00 (m, 1H), 5.34 (dd, J=17.20, 1.76 Hz, 1H), 5.27 (dd, J=10.36, 1.10 Hz, 1H), 4.69 (s, 2H), 4.14 (d, J=5.73 Hz, 2H)

To a solution of compound 2 (180 g, 756 mmol, 1.00 eq) in EtOH (2.00 L) and $H_2O$ (400 mL) was added Fe (426 g, 7.56 mol, 10.0 eq) and $NH_4Cl$ (816 g, 15.1 mol, 20.00 eq). The mixture was stirred at 80° C. for 12 hours. LC-MS (ET8719-17-P1A, RT=0.104 was product) showed ~0% of Reactant 1 was remained. The reaction mixture was filtered and concentrated under reduced pressure to remove EtOH. The residue was diluted with $H_2O$ 1 L and extracted with DCM 500 mL (500 mL*5). The combined organic layers were washed with brine 500 mL, dried over $Na_2SO_4$, filtered and concentrated under reduced pressure to give a residue. The residue was purified by column chromatography ($Al_2O_3$, Petroleum ether/Ethyl acetate=20/1 to ethyl acetate), then the purified product was added 500 mL HCl/EA and stirred for 12 hrs. The mixture was filtered to give compound 3 (120 g, 533 mmol, 97.4% purity, as a HCl salt) LCMS: (M+H$^+$=179.1)$^1H$ NMR: 400 MHz MeOD, δ 7.16 (s, 2H), 7.10 (d, J=2.21 Hz, 1H), 5.89-6.01 (m, 1H), 5.33 (dd, J=17.20, 1.32 Hz, 1H), 5.21 (dd, J=10.58, 1.32 Hz, 1H), 4.55 (s, 2H), 4.08 (d, J=5.29 Hz, 2H)

Synthesis Example 5: Preparation of Intermediate 9 p-Aminobenzoic acid (72 mmol) in cold (0° C.) $CH_2Cl_2$ (100 mL) and acryloyl chloride (36 mmol) were allowed to react in a literature procedure (Patel, K. et al., *Makromol.*

Chem., Macromol. Symp. Phys., 1985, 186:1151-1156). 5.5 g (80%) of the product amide as pale yellow crystals (recrystallized from acetone/H$_2$O). $^1$H NMR (200 MHz, CD$_3$OD) δ 5.72 (q, 1H), 6.30 (m, 2H), 7.62 (d, 2H), 7.86 (d, 2H); $^{13}$C NMR (50 MHz, CD$_3$OD) δ 120.4, 127.1, 128.8, 131.8, 132.1, 144.1, 166.4, 169.6. MS (m/z): 192 [MH]$^+$.

Synthesis Example 6: Preparation of Intermediate 11

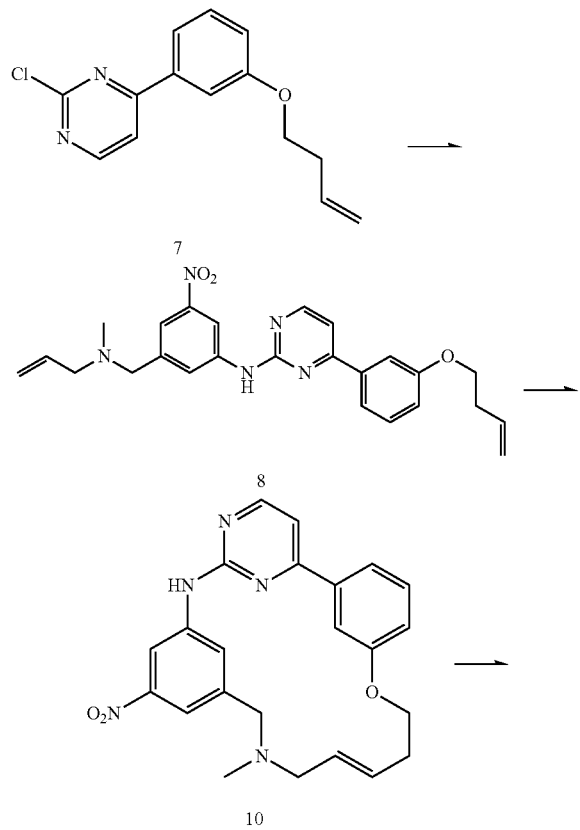

Step 1: to a mixture of intermediate 7 (4.5 mmol) and intermediate 4 (6.8 mmol) in n-butanol (15 mL) at ambient temperature was added 1N HCl (5.0 mL) and the resulting mixture was stirred at 100° C. for overnight. The reaction mixture was cooled to 0° C. and quenched with H$_2$O. The product was extracted with CH$_2$Cl$_2$ thrice and the combined organic extracts were washed with saturated NaHCO$_3$ followed by brine, dried over Na$_2$SO4 and concentrated under reduced pressure to furnish an oil, which was purified by column (EtOAc/Hexane) to obtain intermediate 8, MS (m/z): 446 [MH]$^+$. $^1$H NMR: CDCL$_3$ 400 MHz. δ 8.622 (d, J=5.6 Hz, H), 7.66 (s, H), 7.623 (d, J=5.6 Hz, 2H), 7.407 (t, J=8.0 Hz, H), 7.078 (dd, J=8.0 Hz, H), 5.897-5.965 (m, H), 5.124-5.222 (m, 2H), 4.111 (t, J=6.4 Hz 2H), 2.561-2.610 (m, 2H).

Step 2: To a degassed solution of intermediate 8 (3 mmol) and TFA (7.5 mmol) in CH$_2$Cl$_2$ (1000 mL) at ambient temperature was added Grubbs 2$^{nd}$ generation catalyst (0.3 mmol). The resulting mixture was stirred at 50° C. for overnight. The reaction mixture was cooled and concentrated under reduced pressure to furnish an oil, which was purified by preparative HPLC to obtain intermediate 10, MS (m/z): 418 [MH]$^+$. $^1$H NMR (400 MHz, DMSO-d$_6$) 0.85 (t, J=7.50 Hz, 1H) 1.10-1.33 (m, 1H) 1.42-1.78 (m, 1H) 2.00-2.39 (m, 3H) 4.05-4.22 (m, 2H) 5.03-5.22 (m, 1H) 5.72 (s, 2H) 7.07-7.24 (m, 1H) 7.39-7.56 (m, 2H) 7.62 (d, J=7.50 Hz, 1H) 7.70-7.85 (m, 2H) 8.03-8.17 (m, 1H) 8.60 (d, J=4.41 Hz, 1H)

Step 3: To a solution of intermediate 10 (1 mmol) in MeOH/CH$_2$Cl$_2$ (1:1, 10 mL) at ambient temperature was added SnCl$_2$.2H$_2$O (3 mmol) and the resulting mixture was stirred overnight. The reaction mixture was cooled to 0° C. and quenched with saturated Na$_2$CO$_3$. The product was extracted with CH$_2$Cl$_2$ thrice and the combined organic extracts were washed with H$_2$O followed by brine, dried over Na$_2$SO$_4$ and concentrated under reduced pressure to furnish an oil, which was purified by column chromatography (EtOAc/Hexane) to obtain intermediate 11, [MH]$^+$=388. 1H NMR (400 MHz, METHANOL-d4) 8.73 (s, 1H), 8.50 (d, J=5.1 Hz, 1H), 8.00-7.95 (m, 1H), 7.58 (d, J=7.8 Hz, 1H), 7.47 (t, J=8.0 Hz, 1H), 7.38 (d, J=5.5 Hz, 1H), 7.18 (dd, J=2.3, 7.8 Hz, 1H), 6.87 (t, J=2.0 Hz, 1H), 6.78 (s, 1H), 6.26-6.16 (m, 1H), 5.82 (td, J=7.6, 15.0 Hz, 1H), 4.62 (d, J=11.7 Hz, 1H), 4.34-4.18 (m, 2H), 4.05 (br. s., 1H), 3.91 (d, J=13.3 Hz, 1H), 3.80 (br. s., 1H), 2.72-2.61 (m, 5H)

Synthesis Example 7: Preparation of IM-16-4

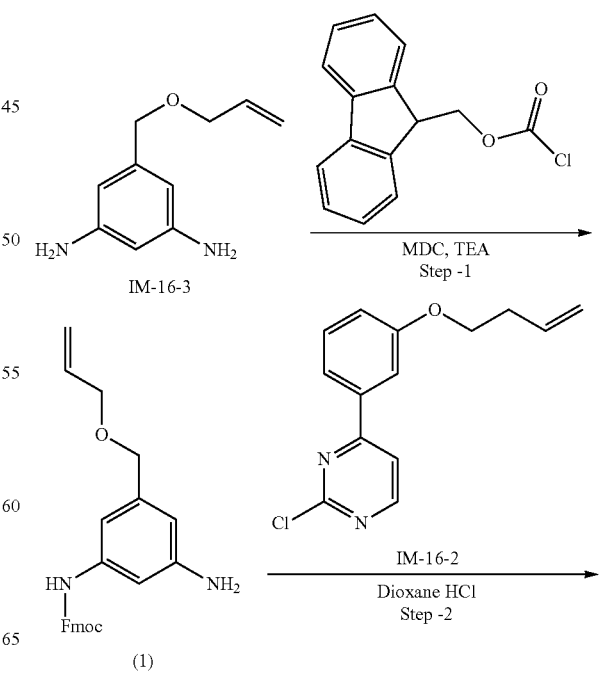

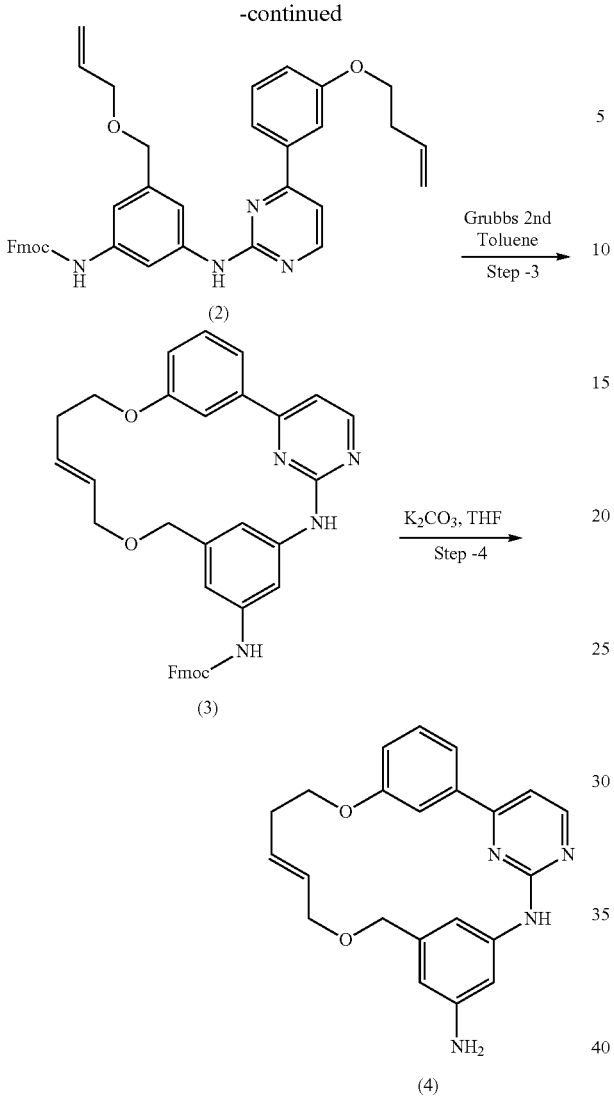

(2)

Grubbs 2nd Toluene
Step -3

(3)

K₂CO₃, THF
Step -4

(4)

To a suspension of compound IM-16-3 (12 g, 67.37 mmol, 1.0 eq) in MDC (100.0 mL) was added FMOC chloride (15.6 g, 60.0 mmol, 0.9 eq) portion wise and allow to stir for 5 mins, then TEA (61.29 g, 605 mmol, 3.0 eq) was added to it drop wise, the mixture was stirred at room temperature for 10 mins There are two spot generated on TLC (mono-Fmoc and Di-Fmoc) TLC (Ethyl acetate/Hexane=5:5, $R_{f\text{-}SM(IM\text{-}16\text{-}3)}$=0.16, $R_f(\text{mono})_P$=0.33, $R_f(\text{Di})_P$=0.63) indicated the starting material was consumed. The organic solvents concentrated in vacuum, residue was extracted with DCM (50 mL*3). The combined organic phase was washed with brine (100 mL*2), dried with anhydrous Na₂SO₄, filtered and concentrated in vacuum to get crude material which was purified by column chromatography, product eluted at 50% ethyl acetate in n-hexane. After purification, intermediate-1 (8.0 g, crude), was obtained as a light yellow solid. LCMS: (M+H⁺): 401.2

To a solution of Intermediate 2 (9 g, 14 mmol, 1.00 eq) in toluene (9.00 L) was added GRUBBSCATALYST2NDGENERATION (1.22 g, 1.14 mmol, 0.1 eq) under N₂. The reaction mixture was refluxed at 80° C. for 16 h. TLC (Ethyl acetate/n-hexane=5:5, $R_{f\text{-}SM(Int\text{-}2)}$=0.73, $R_{f\text{-}P}$=0.43) indicated the starting material was consumed. The residue was concentrated to give Intermediate 3 (6 g, containing catalyst) was obtained as black solid. LCMS: (M+H⁺): 597.38

To a solution of Intermediate-3 (6 g, 10.0 mmol, 1.0 eq) in THF (500 mL) was added K₂CO₃ (4.17 g, 30.7 mmol, 3.07 eq) was stirred at reflux temperature for 16 hr. TLC (Neat Ethyl acetate, $R_{f\text{-}SM(Int\text{-}3)}$=0.81, $R_{f\text{-}P}$=0.42) indicated the starting material was consumed. The mixture was quenched with water, extracted with Ethyl acetate (250 mL*2). The combined organic phase was washed with brine (100 mL*2), dried with anhydrous Na₂SO₄, filtered and concentrated in vacuum, then crude material was dissolved in 2N HCL, allowed to stir and sonicate for 30 mins and mixture was filtered though celite bed to remove black color impurities of GRUBB'S CATALYST, filtrate was extracted with Ethyl acetate (125 mL*2). So in non-polar impurities can be easily removed, followed by aqueous solution was neutralized with solid NaHCO₃ till PH 7 to 8 and extracted with Ethyl acetate (125 mL*2) to give intermediate-4 (2 g, crude) which was obtained as a light yellow solid, which was purified by preparing HPLC using following method. From preparation, HPLC (1.05g of Intermediate-4) was obtained which containing trans isomer (0.9 g, 85.71%) of trans isomer and cis isomer (0.15g, 14.29%). ¹H NMR: for Cis-isomer DMSO 400 MHz δ 9.44 (s, 1H), 8.509-8.497 (d, J=4.8 Hz, 1H), 7.981-7.971 (t, J=1.6 Hz, 1H), 7.846 (s, H), 7.642-7.622 (d, J=8.0 Hz, 1H), 7.442-7.378 (m, 2H), 7.083-7.057 (dd, J=2.4 Hz, J=2 Hz, 1H), 6.349-6.339 (t, J=2.0 Hz, 1H), 6.226 (s, 1H), 5.736-5.646 (m, 2H), 4.996 (s, 2H), 4.346-4.325 (d, J=8.4 Hz, 2H), 4.225-4.209 (d, J=6.4 Hz, 2H), 4.040-4.012 (t, J=5.6 Hz, 2H). ¹H NMR: for trans-isomer DMSO 400 MHz δ 9.487 (s, 1H), 8.512-8.499 (d, J=5.2 Hz 1H), 7.933-7.917 (m, 2H), 7.629-7.607 (dd, J=0.8 Hz, J=8 Hz 2H), 7.478-7.438 (t, J=5.6 Hz, 1H), 7.364-7.351 (d, J=5.2 Hz, 1H), 7.207-7.181 (dd, J=2.4 Hz, J=8 Hz, 1H), 6.306-6.302 (d, J=1.6 Hz, 2H), 5.799-5.744 (m, 1H), 5.641-5.596 (m, 1H), 4.981 (s, 1H), 4.346 (s, 2H), 4.171-4.144 (t, J=5.2 Hz, 2H), 4.041-4.025 (d, J=6.4 Hz, 2H).

Synthesis Example 8: Preparation of CY-16-1

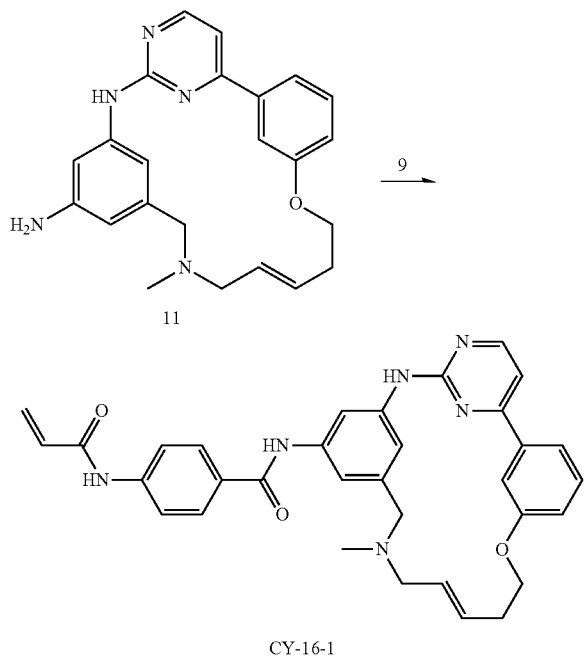

CY-16-1

Step 4: To a stirred solution of intermediate 11 (0.3 mmol) and intermediate 9 (0.4 mmol) in 10 mL pyridine was added 250 mg (0.4 mmol) propylphosphonic anhydride. The resulting solution was stirred at RT for 72 hr. The solvent was removed in vacuo and the residue was stirred with 50 mL water to give a yellow solid that was isolated by filtration. Purification of the crude product by silica gel chromatography using 5% $CH_3OH$—$CH_2Cl_2$ gave title compound, MS (m/z): 561 [MH]$^+$. 1H NMR (400 MHz, METHANOL-d4) 2.62-2.71 (m, 5H) 3.75-3.87 (m, 1H) 3.99 (dd, J=13.23, 7.94 Hz, 1H) 4.09 (dd, J=12.35, 5.73 Hz, 1H) 4.16-4.25 (m, 1H) 4.26-4.34 (m, 1H) 4.64-4.72 (m, 1H) 5.81 (dd, J=9.48, 2.43 Hz, 2H) 6.14-6.26 (m, 1H) 6.35-6.50 (m, 2H) 7.27 (td, J=8.82, 2.21 Hz, 1H) 7.51 (td, J=7.94, 5.29 Hz, 1H) 7.55-7.70 (m, 4H) 7.75 (s, 1H) 7.81 (d, J=8.82 Hz, 1H) 7.88-7.99 (m, 2H) 8.52 (d, J=5.73 Hz, 1H) 8.64 (br. s., 1H) 8.79 (s, 1H)

Synthesis Example 9: Alternative Route to Prepare CY-16-1

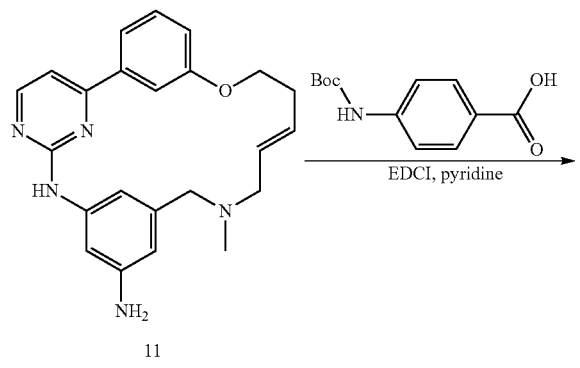

11

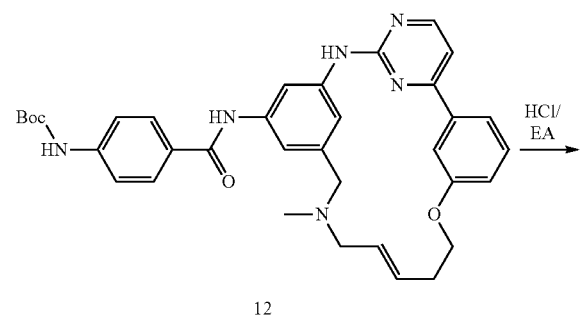

12

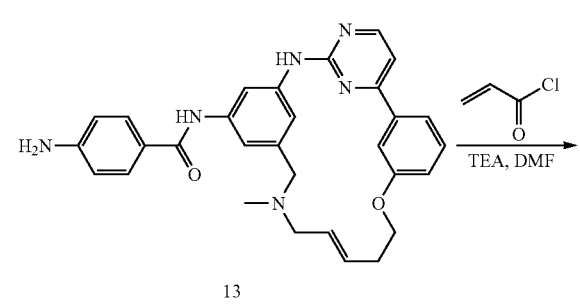

13

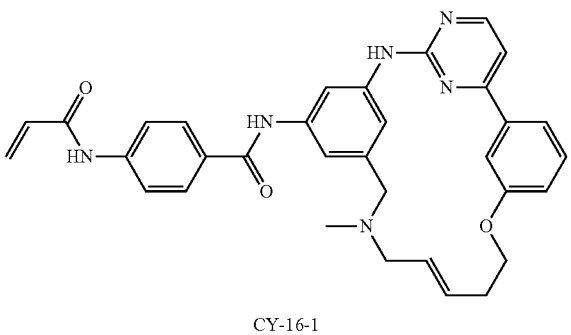

CY-16-1

The mixture of compound 11 (100.00 mg, 258.08 umol, 1.00 eq), 4-((tert-butoxycarbonyl)amino)benzoic acid (67.35 mg, 283.89 umol, 1.10 eq) and EDCI (59.37 mg, 309.70 umol, 1.20 eq) in Pyridine (2.00 mL) was stirred at 80° C. for 0.5 hr. TLC showed the reaction was complete. The mixture was concentrated. Compound 12 (130.00 mg, crude) was obtained as brown gum.

The mixture of compound 12 (130.00 mg, 214.27 umol, 1.00 eq) in EA (2.00 mL) was added HCl (g)/EtOAc (2.14 mmol, 10.00 eq) and stirred at 20° C. for 1 hr. TLC showed the reaction was complete. The mixture was concentrated. Compound 13 (100.00 mg, crude) was obtained as brown gum. To the solution of compound 13 (100.00 mg, 197.39 umol, 1.00 eq) and TEA (39.95 mg, 394.78 umol, 54.73 uL, 2.00 eq) in DMF (2.00 mL) was added prop-2-enoyl chloride (19.65 mg, 217.13 umol, 17.70 uL, 1.10 eq). The mixture was stirred at 20° C. for 1 h. LCMS showed the reaction was complete. The mixture was concentrated. The residue was purified by prep-HPLC (HCl condition). Compound CY-16-1 (16.00 mg, 26.80 umol, 13.58% yield, HCl salt) was obtained as yellow solid. $^1$H NMR (400 MHz, METHANOL-d4) 2.62-2.71 (m, 5H) 3.75-3.87 (m, 1H) 3.99 (dd, J=13.23, 7.94 Hz, 1H) 4.09 (dd, J=12.35, 5.73 Hz, 1H) 4.16-4.25 (m, 1H) 4.26-4.34 (m, 1H) 4.64-4.72 (m, 1H) 5.81 (dd, J=9.48, 2.43 Hz, 2H) 6.14-6.26 (m, 1H) 6.35-6.50 (m, 2H) 7.27 (td, J=8.82, 2.21 Hz, 1H) 7.51 (td, J=7.94, 5.29 Hz, 1H) 7.55-7.70 (m, 4H) 7.75 (s, 1H) 7.81 (d, J=8.82 Hz, 1H) 7.88-7.99 (m, 2H) 8.52 (d, J=5.73 Hz, 1H) 8.64 (br. s., 1H) 8.79 (s, 1H)

Synthesis Example 10: Preparation of CY-16-2

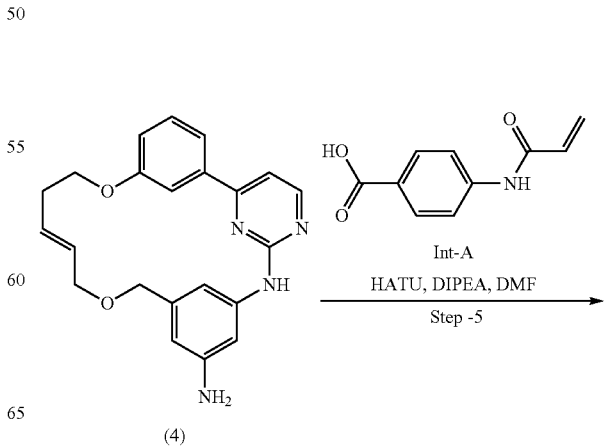

(4)

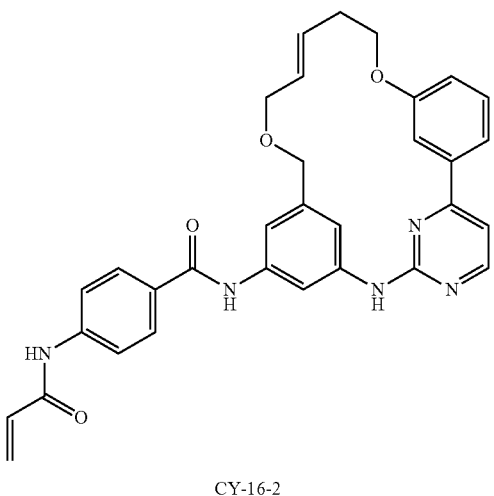

CY-16-2

To a solution of intermediate-A (0.07 g, 0.4 mmol, 1.5 eq) in DMF (5 mL) was added HATU (0.12 g, 0.3 mmol, 1.2 eq), DIPEA (0.1 g, 0.8 mmol, 3.0 eq) at 0° C., to it was added IM-16-4 (0.1 g, 0.27 mmol, 1.0 eq) and allow to stirred at same temperature for 1 hr. TLC (Chloroform: Methanol=9.5:0.5, $R_{f\text{-}SM(Int\text{-}4)}$=0.43, $R_{f\text{-}P}$=0.19) indicated the starting material was consumed. The reaction mixture was poured into cold water, solid material filtered; dry under vacuum to give intermediate-5 (0.120 g, crude) was obtained as a light yellow solid, which was purified by preparing HPLC using following method. After purification, NEWAVE-1604 (27.7 mg) was obtained as an off white solid. $^1$H NMR: DMSO 400 MHz δ 10.441 (s, 1H), 10.140 (s, 1H), 9.847 (s, 1H), 8.567-8.554 (d, J=5.2 Hz, 1H), 8.554 (s, 1H), 8.00-7.978 (d, J=8.8, 1H), 7.932 (s, 1H), 7.820-7.798 (d, J=8.8 Hz, 2H), 7.760-7.617 (t, J=7.6 Hz, 21H), 7.501-7.376 (m, 3H), 7.231-7.210 (t, J=5.6 Hz, 1H), 6.556 (s, 4H), 6.474-6.449 (d, J=10 Hz, 1H), 6.338-6.296 (dd, J=1.6 Hz, J=2 Hz, 1H), 5.836-5.806 (dd, J=2 Hz, J=2 Hz, 1H), 5.710 (m, 1H) 4.506 (s, 2H), 4.192-4.165 (t, J=5.6 Hz, 2H), 4.109-4.093 (t, J=6.4 Hz, 2H), The compounds below are prepared by methods substantially identical, similar, or analogous to those disclosed in the General Scheme and Examples 1-10.

| Example | Structure | m/z (MH$^+$) |
|---|---|---|
| CY-16-3 | 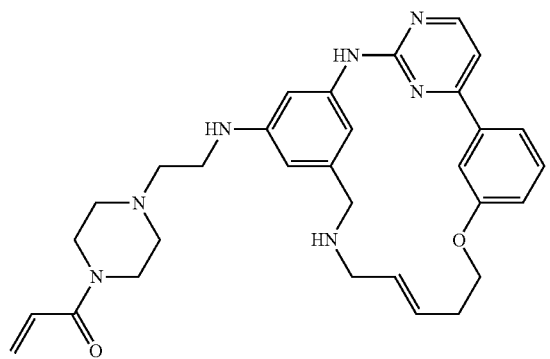 [SMILES: C=CC(=O)N1CCN(CCNc2cc3cc(c2)Nc2nccc(n2)-c2cccc(c2)OCC/C=C/CNC3)CC1] | 540 |
| CY-16-4 | 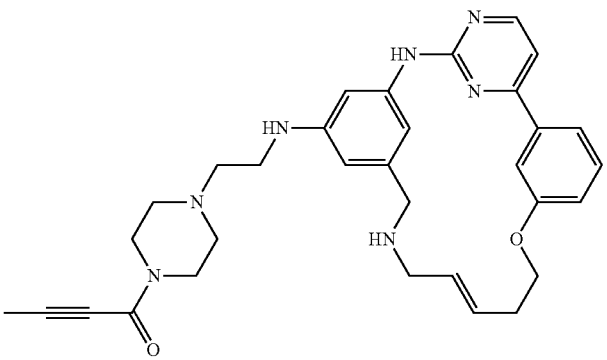 [SMILES: CC#CC(=O)N1CCN(CCNc2cc3cc(c2)Nc2nccc(n2)-c2cccc(c2)OCC/C=C/CNC3)CC1] | 552 |

| Example | Structure | m/z (MH⁺) |
|---|---|---|
| CY-16-5 | 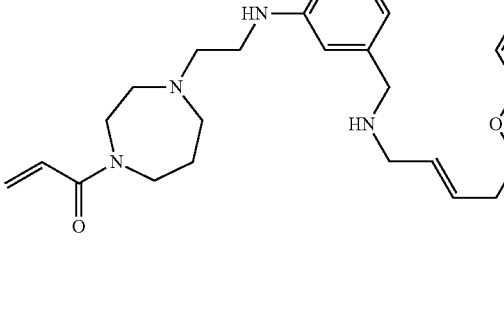 | 554 |
| CY-16-6 | 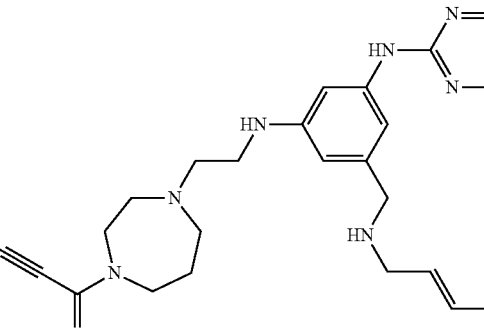 | 566 |
| CY-16-7 | 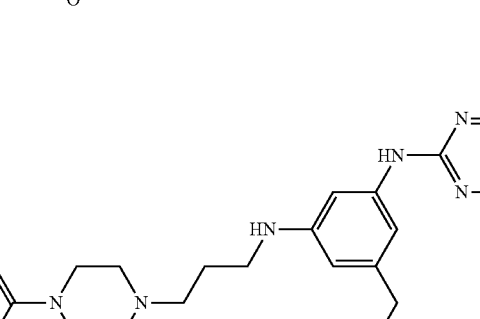 | 554 |
| CY-16-8 | 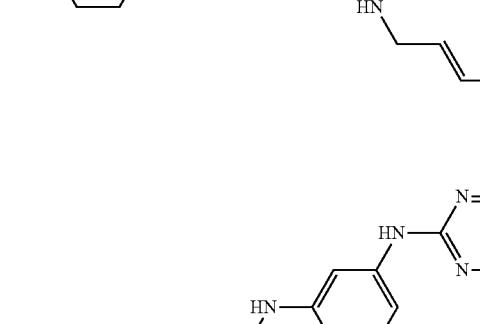 | 566 |

-continued

| Example | Structure | m/z (MH⁺) |
|---|---|---|
| CY-16-9 | 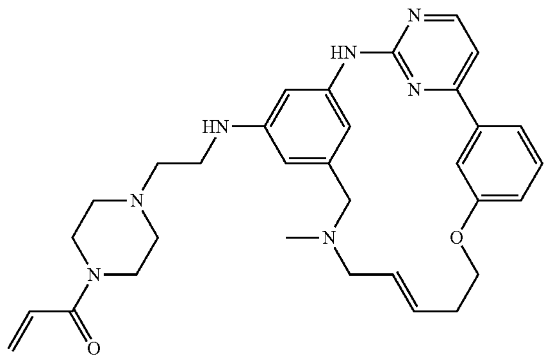 [SMILES: C=CC(=O)N1CCN(CCNc2cc3cc(c2)Nc2nccc(n2)-c2cccc(c2)OCC/C=C/CN(C)C3)CC1] | 554 |
| CY-16-10 | 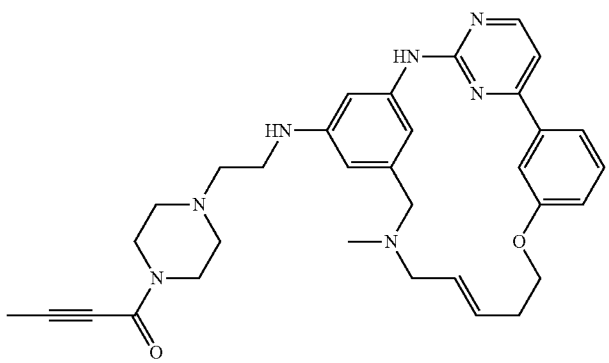 [SMILES: CC#CC(=O)N1CCN(CCNc2cc3cc(c2)Nc2nccc(n2)-c2cccc(c2)OCC/C=C/CN(C)C3)CC1] | 566 |
| CY-16-11 | 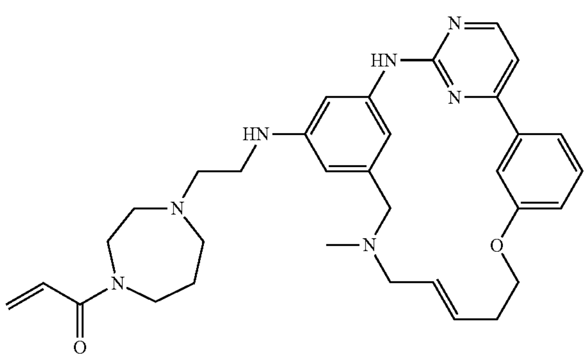 [SMILES: C=CC(=O)N1CCCN(CCNc2cc3cc(c2)Nc2nccc(n2)-c2cccc(c2)OCC/C=C/CN(C)C3)CC1] | 568 |
| CY-16-12 | 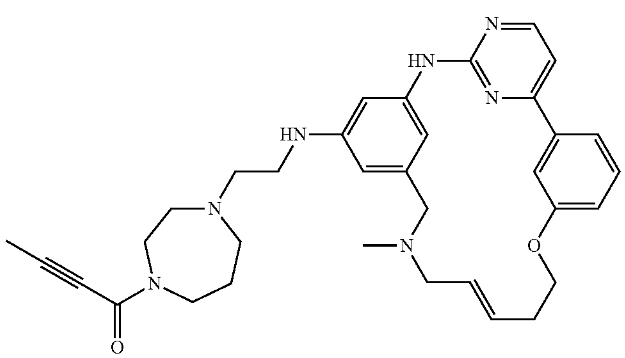 | 580 |

| Example | Structure | m/z (MH+) |
|---|---|---|
| CY-16-13 | 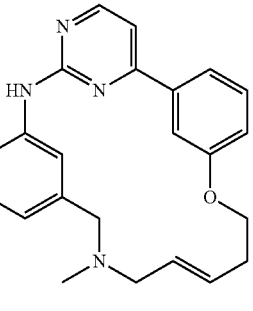 | 568 |
| CY-16-14 | 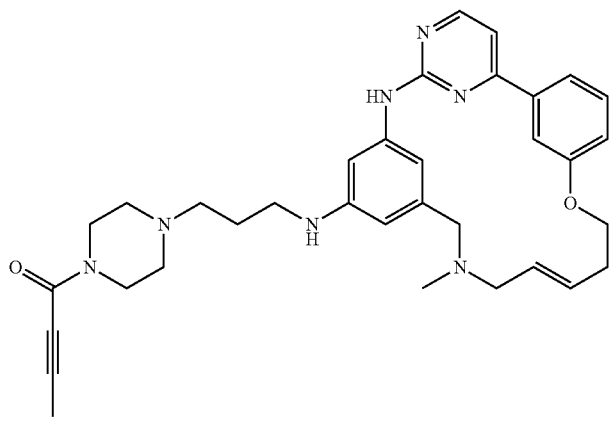 [SMILES: CC#CC(=O)N1CCN(CCCNc2cc3cc(c2)Nc2nccc(n2)-c2cccc(c2)OCC/C=C/CN(C)C3)CC1] | 580 |
| CY-16-15 | 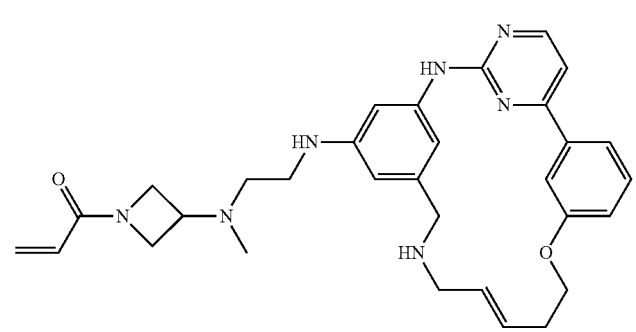 [SMILES: C=CC(=O)N1CC(N(C)CCNc2cc3cc(c2)Nc2nccc(n2)-c2cccc(c2)OCC/C=C/CNC3)C1] | 540 |
| CY-16-16 | 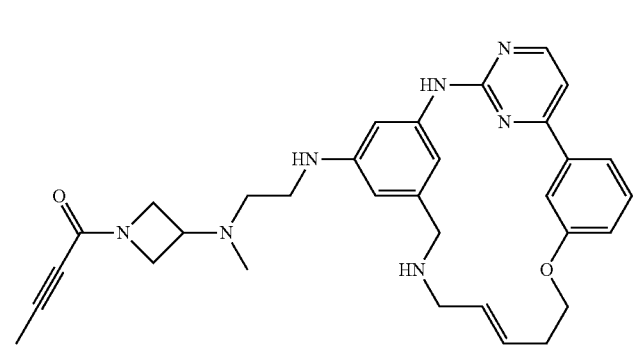 [SMILES: CC#CC(=O)N1CC(N(C)CCNc2cc3cc(c2)Nc2nccc(n2)-c2cccc(c2)OCC/C=C/CNC3)C1] | 552 |

-continued

| Example | Structure | m/z (MH+) |
|---|---|---|
| CY-16-17 | 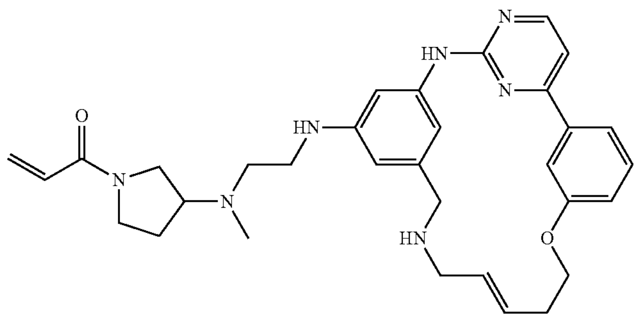 [SMILES: C=CC(=O)N1CCC(N(C)CCNc2cc3cc(c2)Nc2nccc(n2)-c2cccc(c2)OCC/C=C/CNC3)C1] | 554 |
| CY-16-18 | 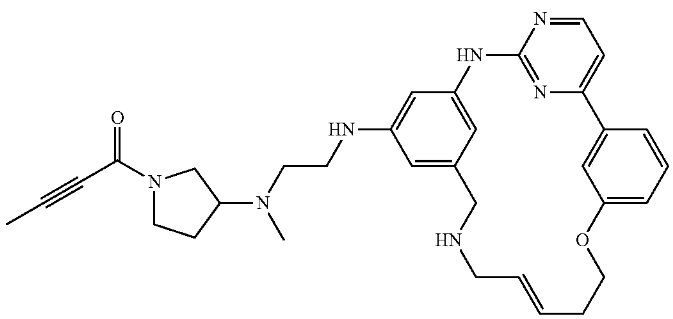 [SMILES: CC#CC(=O)N1CCC(N(C)CCNc2cc3cc(c2)Nc2nccc(n2)-c2cccc(c2)OCC/C=C/CNC3)C1] | 566 |
| CY-16-19 | 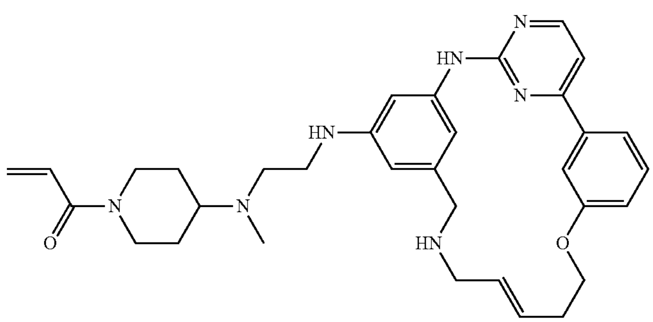 [SMILES: C=CC(=O)N1CCC(N(C)CCNc2cc3cc(c2)Nc2nccc(n2)-c2cccc(c2)OCC/C=C/CNC3)CC1] | 568 |
| CY-16-20 | 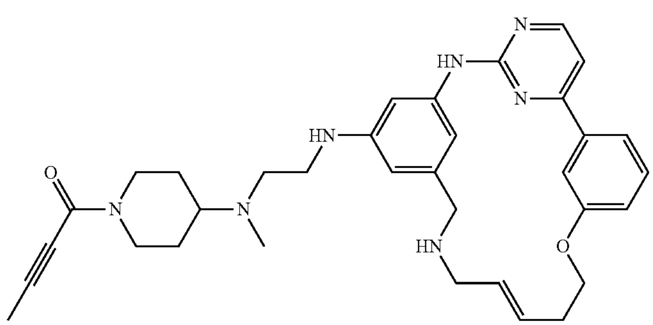 [SMILES: CC#CC(=O)N1CCC(N(C)CCNc2cc3cc(c2)Nc2nccc(n2)-c2cccc(c2)OCC/C=C/CNC3)CC1] | 580 |
| CY-16-21 | 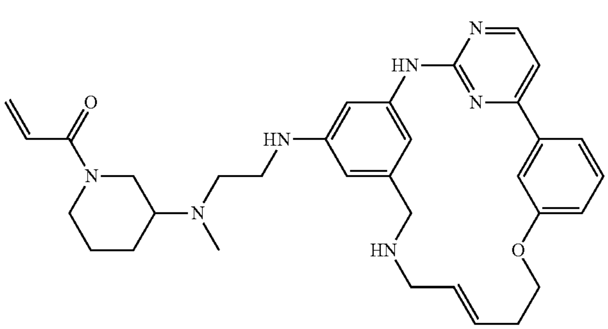 [SMILES: C=CC(=O)N1CCCC(N(C)CCNc2cc3cc(c2)Nc2nccc(n2)-c2cccc(c2)OCC/C=C/CNC3)C1] | 568 |

-continued
| Example | Structure | m/z (MH⁺) |
|---|---|---|
| CY-16-22 | 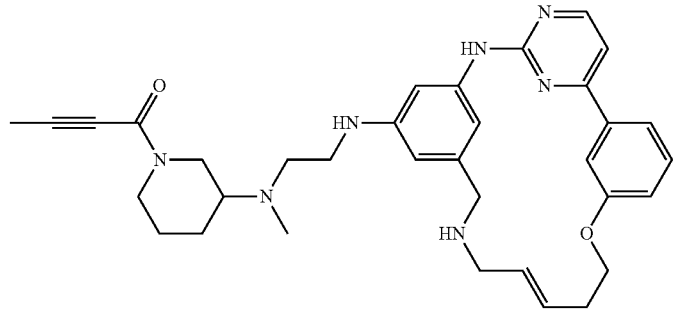 | 580 |
| CY-16-23 | 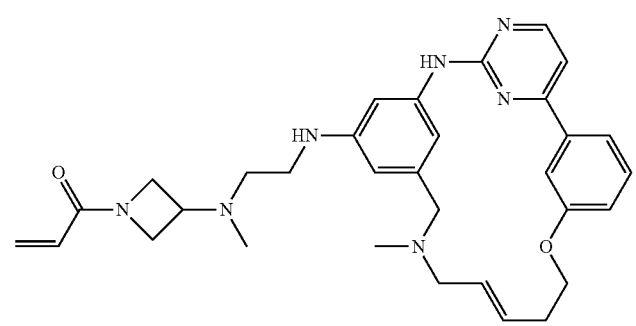 | 554 |
| CY-16-24 | 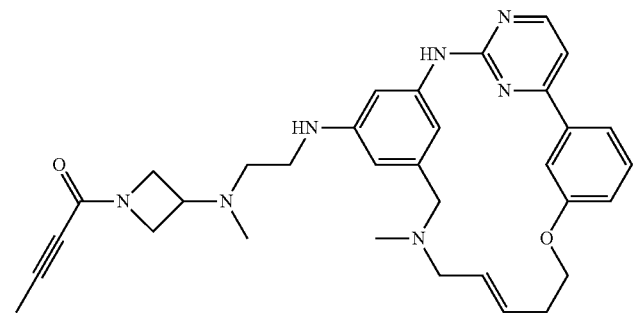 | 566 |
| CY-16-25 | 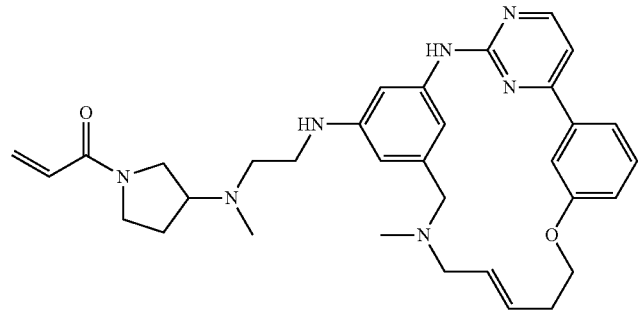 [SMILES: C=CC(=O)N1CCC(N(C)CCNc2cc3cc(c2)Nc2nccc(n2)-c2cccc(c2)OCC/C=C/CN(C)C3)C1] | 568 |
| CY-16-26 | 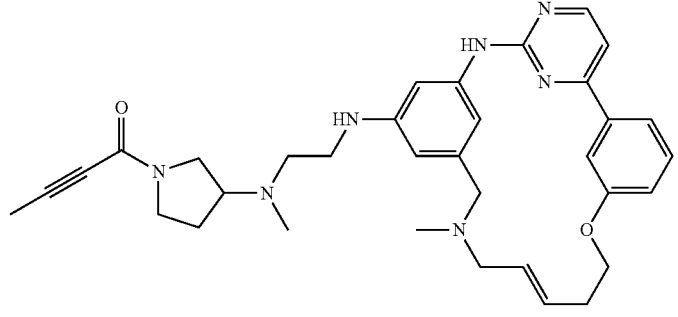 [SMILES: CC#CC(=O)N1CCC(N(C)CCNc2cc3cc(c2)Nc2nccc(n2)-c2cccc(c2)OCC/C=C/CN(C)C3)C1] | 580 |

-continued

| Example | Structure | m/z (MH+) |
|---|---|---|
| CY-16-27 | 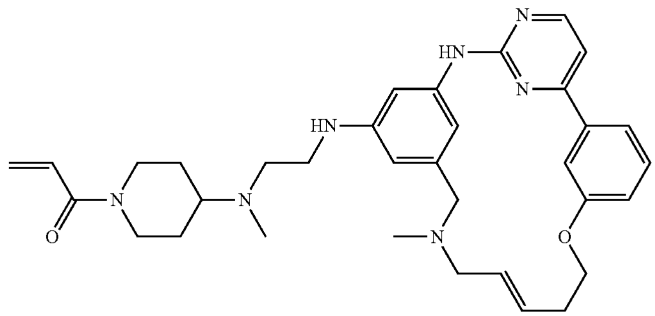 [SMILES: C=CC(=O)N1CCC(N(C)CCNc2cc3cc(c2)Nc2nccc(n2)-c2cccc(c2)OCC/C=C/CN(C)C3)CC1] | 582 |
| CY-16-28 | 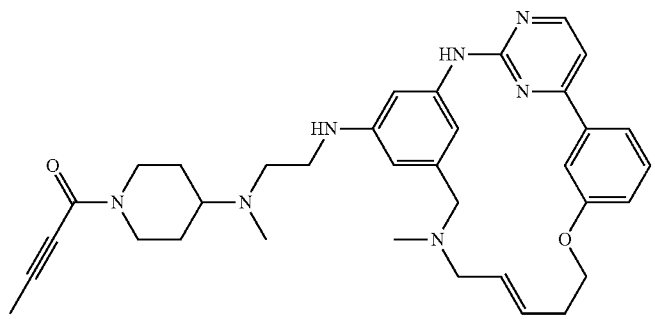 [SMILES: CC#CC(=O)N1CCC(N(C)CCNc2cc3cc(c2)Nc2nccc(n2)-c2cccc(c2)OCC/C=C/CN(C)C3)CC1] | 594 |
| CY-16-29 | 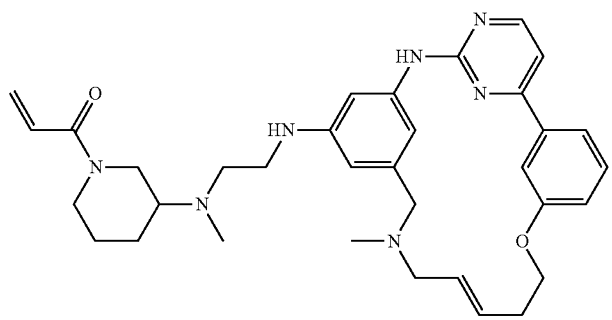 [SMILES: C=CC(=O)N1CCCC(N(C)CCNc2cc3cc(c2)Nc2nccc(n2)-c2cccc(c2)OCC/C=C/CN(C)C3)C1] | 582 |
| CY-16-30 | 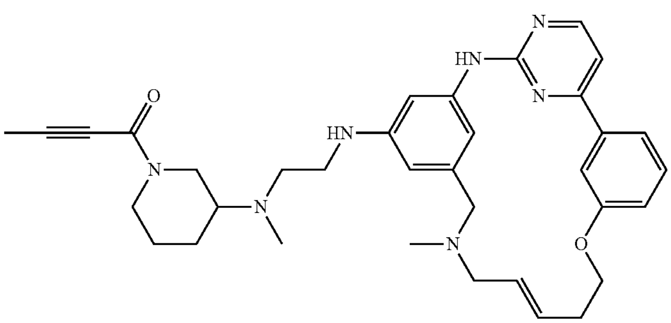 [SMILES: CC#CC(=O)N1CCCC(N(C)CCNc2cc3cc(c2)Nc2nccc(n2)-c2cccc(c2)OCC/C=C/CN(C)C3)C1] | 594 |

Biological Example 1: CDK7 Binding Constant ($K_d$) Determination

The $K_d$ of the compounds were determined by KINOMEscan™ assay, the industry's most comprehensive high-throughput system for screening compounds against large numbers of human kinases. KINOMEscan™ assay is based on a competition binding assay that quantitatively measures the ability of a compound to compete with an immobilized, active-site directed ligand. The assay is performed by combining three components: DNA-tagged kinase; immobilized ligand; and a test compound. The ability of the test compound to compete with the immobilized ligand is measured via quantitative PCR of the DNA tag.

The kinase-tagged T7 phage strains were prepared in an *E. coli* host derived from the BL21 strain. *E. coli* were grown to log-phase and infected with T7 phage and incubated with shaking at 32° C. until lysis. The lysates were centrifuged and filtered to remove cell debris. The remaining kinases were produced in HEK-293 cells and subsequently tagged with DNA for qPCR detection. Streptavidin-coated magnetic beads were treated with biotinylated small molecule ligands for 30 minutes at room temperature to generate affinity resins for kinase assays. The liganded beads were blocked with excess biotin and washed with blocking buffer (SeaBlock (Pierce), 1% BSA, 0.05% Tween 20, 1 mM DTT) to remove unbound ligand and to reduce non-specific binding. Binding reactions were assembled by combining kinases, liganded affinity beads, and test compounds in 1× binding buffer (20% SeaBlock, 0.17×PBS, 0.05% Tween 20, 6 mM DTT). All reactions were performed in polystyrene 96-well plates in a final volume of 0.135 ml. The assay plates were incubated at room temperature with shaking for 1 hour and the affinity beads were washed with wash buffer (1×PBS, 0.05% Tween 20). The beads were then re-suspended in elution buffer (1×PBS, 0.05% Tween 20, 0.5 µM nonbiotinylated affinity ligand) and incubated at room temperature with shaking for 30 minutes. The kinase concentration in the eluates was measured by qPCR. An 11-point 3-fold serial dilution of each test compound was prepared in 100% DMSO at 100×final test concentration and subsequently diluted to 1× in the assay (final DMSO concentration=1%).

Most $K_d$ were determined using a compound top concentration=30,000 nM. If the initial Kd determined was <0.5 nM (the lowest concentration tested), the measurement was repeated with a serial dilution starting at a lower top concentration. A $K_d$ value reported as 40,000 nM indicates that the $K_d$ was determined to be >30,000 nM. Binding constants ($K_d$s) were calculated with a standard dose-response curve using the Hill equation: Response=Background+(Signal−Background)/[1+($K_d^{Hill\ slope}$/Dose$^{Hill\ Slope}$)]. The Hill Slope was set to 1. Curves were fitted using a non-linear least square fit with the Levenberg-Marquardt algorithm. Such assays, carried out with a range of doses of test compounds, allow the determination of an approximate $K_d$ value. THZ-1 (a CDK-7 inhibitor reported in the literature) was used as reference compound As shown in the following table, the Kd value of CY-16-1 clearly shows that CY-16-1 is a potent CDK inhibitor.

|  | CY-16-1 | THZ-1 |
| --- | --- | --- |
| CDK7 | <1 nM | 48 nM |

Biological Example 2: Inhibition of CDK-7 Enzymatic Activity

Material: CDK7/cyclinHl/MNAT1 (Accession number for CDK7; NP 001790, for cyclinHl; NP 001230, for MNAT1; NP 002422.1) Recombinant Human Full-Length protein, Histidine-tagged CDK7 (MW=43.2 kDa), Histidine-tagged cyclin Hl (MW=42.6 kDa), Histidine-tagged MNAT1 (MW=40.5 kDa), were expressed in insect cells. Specific activity of recombinant enzyme complex was measured to be equal to 94 nmole of phosphate transferred to CDK7/9tide substrate (YSPTSPSYSPTSPSYSPTSPSK-KKK) per minute per mg of total protein at 30° C. Activity was determined with a final protein concentration at 3.33 µg/mL. Enzyme was stored at a concentration of 0.42 mg/ml in 50 mM Tris (pH 7.5), 150 mM NaCl, 0.5 mM EDTA, 0.02% Triton X-100, 2 mM DTT, 50% Glycerol.

For CDK7 activity assay, p33 ATP tracers were incubated with purified recombinant specific combination of purified CDK kinases, cyclins and substrates to monitor the enzyme activity. In these assays, individual reactions were carried out in specific conditions describe below with reaction buffer: 20 mM HEPES (pH 7.5), 10 mM $MgCl_2$, 1 mM EGTA, 0.02% Brij 35, 0.02 mg/ml BSA, 0.1 mM $Na_3VO_4$, 2 mM DTT. An equal volume of 25% TCA was added to stop the reaction and precipitate the labeled peptides. Precipitated proteins were trapped onto glass fiber B filterplates and excess unlabeled p33 ATP was washed off. The plates were allowed to air-dry prior to the addition of 30 uL/well of Packard Microscint 20. The amount of incorporated isotope was measured using a Perkin Elmer TopCount plate reader. Different concentrations of compounds were added to reaction to assess the activity of compounds to inhibit PDGF-beta kinase. IC50 was calculated using Prism software with sigmoidal dose-response curve fitting. CDK7/cyclinHl/MNAT1:100 nM CDK7/cyclinHl/MNAT1 and 20 µM Histon Hl were mixed in the reaction buffer with 1 µM ATP and 1% DMSO. Reaction was incubated for 2 hours at room temperature and conversion rate of ATP was measured to be 5.5%. Staurosporine and THZ-1(a CDK-7 inhibitor reported in the literature) was used as reference compound. Such assays, carried out with a range of doses of test compounds, allow the determination of an approximate IC50 value. Although the inhibitory properties of the compounds of the present invention vary with structural change as expected, the activity generally exhibited by these agents is in the range of IC50=0.1-1000 nM.

As shown in the following table, the IC50 value of CY-16-1 clearly shows that CY-16-1 is a potent CDK inhibitor.

|  | CY-16-1 | THZ-1 |
| --- | --- | --- |
| CDK7 | <15 nM | <15 nM |

Biological Example 3: In Vitro Irreversible Kinetics Study

Covalent kinase inhibitors have several characteristics that functionally differentiate themselves from their reversible counterparts. Generally, (1) covalent kinase inhibitors have electrophilic substituents that react covalently with nucleophilic centers on their target kinase; (2) covalent kinase inhibitors exhibit two-step inhibitory kinetics marked by a fast reversible binding event, followed by a slow covalent (irreversible) binding event, which causes the overall kinetics of target inactivation to be slow relative to noncovalent inhibitors; and (3) once covalently bound, covalent kinase inhibitors are impervious to washout of the inhibitors and are no longer ATP-competitive. The scanKINETIC™ assay is used to determine whether the compound is an irreversible inhibitor or reversible inhibitor. Four sets of dose-response curve study Arms (A, B, C, D) comprise a scanKINETIC experiment. Arm A addresses association and dissociation kinetics; Arm B addresses dissociation kinetics; Arm C (in concert with Arm A) addresses association kinetics; and Arm D addresses dissociation kinetics & serves as a control for reagent dilution.

In Arm A, compound and kinase are combined and equilibrated for six hours ($t_1+t_2$). In Arm B, compound and kinase are combined and equilibrated for 1 hour ($t_1$), and the samples are then diluted (30-fold) in reaction buffer (described above) and equilibrated for 5 hours ($t_2$). In Arm C, compound and kinase are combined and equilibrated for 1 hour ($t_1$). In Arm D, compound and kinase are combined and immediately diluted 30-fold in reaction buffer. The reaction is then allowed to equilibrate for 6 hours ($t_1+t_2$). Postequilibration, each study arm sample is combined briefly with liganded affinity beads. All reactions are subsequently washed, eluted, read-out by qPCR, and the data are fit to the Hill equation to calculate apparent $K_d$ values, as described above. Curve fitting intentionally ignores test compound dilution in Arms B&D. For irreversible inhibitors, the Kd values for Arm A&B are equivalent, since for Arm B, the inhibitor fails to dissociate after the reaction dilution step.

Biological Example 4: In Vitro Irreversible Dialysis Assay 700 nM CY-16-1 compound was pre-incubated with 50 nM CDK7/CycH/MAT1 enzyme for 2 h in a buffer comprising: 100 mM HEPES pH7.5, 0.1% BSA, 5 mM MgCl2, 1 mM DTT, 0.01% Triton X-100 and dialyzed at RT against the same buffer for a total time of 24 h (3 changes of the dialysis buffer, nominal cumulative dialysis factor: 30,000). Control samples included: DMSO+50 nM CDK7 dialyzed in the identical manner Un-dialyzed samples with compound were assembled and incubated for 24 h at RT. Following dialysis, the CDK7 activity was measured in real-time format in the presence of 100 uM ATP and 1 uM substrate peptide. Initial velocity was determined in the samples. The dialysis assay of CY-16-1 clearly shows that CY-16-1 is an irreversible inhibitor of CDK7

Biological Example 5: In Vitro Anti-Proliferation Assay

Cell antiproliferation is assayed by PerkinElmer ATPlite™ Luminescence Assay System. Briefly, the various test cancer cell lines are plated at a density of about $1\times10^4$ cells per well in Costar 96-well plates, and are incubated with different concentrations of compounds for about 72 hours in medium supplemented with 5% FBS. One lyophilized substrate solution vial is then reconstituted by adding 5 mL of substrate buffer solution, and is agitated gently until the solution is homogeneous. About 50 μL of mammalian cell lysis solution is added to 100 μL of cell suspension per well of a microplate, and the plate is shaken for about five minutes in an orbital shaker at ~700 rpm. This procedure is used to lyse the cells and to stabilize the ATP. Next, 50 μL substrate solution is added to the wells and microplate is shaken for five minutes in an orbital shaker at ~700 rpm. Finally, the luminescence is measured by a PerkinElmer TopCount® Microplate Scintillation Counter. Such assays, carried out with a range of doses of test compounds, allow the determination of the cellular anti-antiproliferative $IC_{50}$ of the compounds of the present invention.

As shown in the following table, the CY-16-1 has potent anticancer activity in small cell lung cancer (SCLC) cell lines. Cisplatin, the first line treatment of SCLC, was used as a reference drug in this assay:

| SCLC Cell line | CY-16-1 (uM) | Cisplatin (uM) |
| --- | --- | --- |
| NCI-H209 | 0.030 | 0.274 |
| NCI-H69 | 0.032 | 6.996 |
| NCI-H69 | 0.018 | 7.700 |
| NCI-H82 | 0.028 | 4.508 |
| NCI-H446 | 0.019 | 7.452 |
| DMS 114 | 0.029 | 5.954 |

Biological Example 6: In Vivo Xenograft Studies

Typically, athymic nude mice (CD-1 nu/nu) or SCID mice are obtained at age 6-8 weeks from vendors and acclimated for a minimum 7-day period. The cancer cells are then implanted into the nude mice. Depending on the specific tumor type, tumors are typically detectable about two weeks following implantation. When tumor sizes reach ~100-200 mm$^3$, the animals with appreciable tumor size and shape are randomly assigned into groups of 8 mice each, including one vehicle control group and treatment groups. Dosing varies depending on the purpose and length of each study, which typically proceeds for about 3-4 weeks. Tumor sizes and body weight are typically measured three times per week. In addition to the determination of tumor size changes, the last tumor measurement is used to generate the tumor size change ratio (T/C value), a standard metric developed by the National Cancer Institute for xenograft tumor evaluation. In most cases, % T/C values are calculated using the following formula: % T/C=100×ΔT/AC if ΔT>0. When tumor regression occurred (ΔT<0), however, the following formula is used: % T/T0=100×ΔT/T0. Values of <42% are considered significant.

What is claimed is:

1. A compound of Formula (I), or an N-oxide thereof, or a pharmaceutically acceptable salt, polymorph, tautomer, stereoisomer, or an isotopic form thereof:

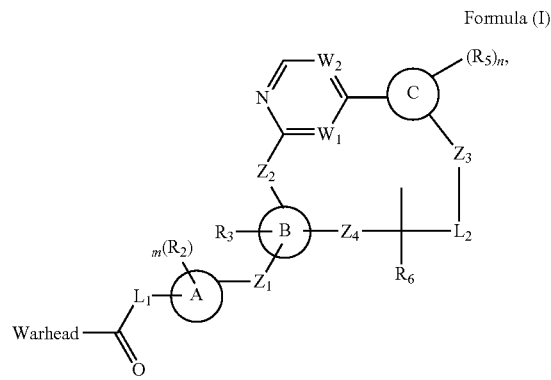

Formula (I)

wherein

A is cycloalkyl, heterocycloalkyl, cycloalkenyl, heterocycloalkenyl, aryl, heteroaryl, fused hetero-bicyclic, or spiro-heterocyclic;

each of B, and C, independently, is cycloalkyl, cycloalkenyl, heterocycloalkyl, heterocycloalkenyl, aryl, or heteroaryl;

each of $Z_1$, $Z_2$, $Z_3$, and $Z_4$ independently, is a bond, $(CR^aR^b)_p$, $(CR^aR^b)_pN(R^a)(CR^aR^b)_q$, $N(R^a)(CR^aR^b)_qN(R^a)$, $(CR^aR^b)_pO(CR^aR^b)_q$, $(CR^aR^b)_pC=C(CR^aR^b)_q$, $(CR^aR^b)_pC\equiv C(CR^aR^b)_q$, $C(R^a)=N$, O, S, C(O), N($R^a$), S($O_2$), OC(O), C(O)O, OSO$_2$, S($O_2$)O, C(O)S, SC(O), C(O)C(O), C(O)N($R^a$), N($R^a$)C(O), S($O_2$)N($R^a$), N($R^a$)S($O_2$), OC(O)O, OC(O)S, OC(O)N($R^a$), OC(O)N($R^a$)(CR$^a$R$^b$)$_{p+1}$N($R^a$)(CR$^a$R$^b$)$_q$, N($R^a$)C(O)O, N($R^a$)

C(O)S, N(R$^a$)C(O)N(R$^b$), (CR$^a$R$^b$)$_p$N(R$^a$)C(O)(CR$^a$R$^b$)$_q$, or (CR$^a$R$^b$)$_p$C(O)N(R$^a$)(CR$^a$R$^b$)$_q$;
each of m, n, p, and q independently, is 0, 1, 2, 3, or 4;
Warhead is

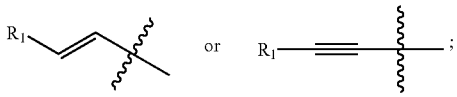

L$_1$ is N(R$_7$) if the atom which L$_1$ connects to ring A is a carbon atom; or L$_1$ is a direct bond if ring A is a heterocycloalkyl, heterocycloalkenyl, or heteroaryl and the atom which L$_1$ connects to ring A is a nitrogen atom;

L$_2$ is (CR$^a$R$^b$)$_s$CH=HC(CR$^a$R$^b$)$_r$ in which each of r, and s independently, is 1, 2, 3, or 4;

each of W$_1$, and W$_2$ independently, is C(R$_4$) or N;

each of R$_1$, R$_2$, R$_3$, R$_4$, R$_5$, R$_6$, and R$_7$, independently, is H, alkyl, alkenyl, alkynyl, cycloalkyl, cycloalkenyl, heterocycloalkyl, heterocycloalkenyl, aryl, heteroaryl, halo, nitro, oxo, cyano, —OR$_a$, —SR$_a$, —NR$_b$R$_c$, —C(O)R$_a$, —S(O)R$_a$, —SO$_2$R$_a$, —P(O)R$_b$R$_c$, —C(O)N(R$_b$)R$_c$, —N(R$_b$)C(O)R$_c$, —C(O)OR$_a$, —OC(O)R$_a$, —SO$_2$N(R$_b$)R$_c$, —N(R$_b$)SO$_2$R$_c$, -alkyl-R$_a$, -alkyl-C(O)R$_a$, -alkyl-NR$_b$R$_c$, -alkyl-C(O)N(R$_b$)R$_c$, -alkyl-N(R$_b$)C(O), or -alkyl-N(R$_b$)SO$_2$R$_c$; and each of R$^a$, R$^b$, R$_a$, R$_b$, and R$_c$, independently, is H, alkyl, alkenyl, alkynyl, cycloalkyl, cycloalkenyl, heterocycloalkyl, heterocycloalkenyl, aryl, heteroaryl, halo, cyano, amine, nitro, hydroxy, —C(O)NHOH, alkoxy, alkoxyalkyl, haloalkyl, hydroxyalkyl, aminoalkyl, alkylcarbonyl, alkoxycarbonyl, alkylcarbonylamino, dialkylamino, or alkylamino.

2. The compound according to claim 1 or an N-oxide thereof, or a pharmaceutically acceptable salt, polymorph, tautomer, stereoisomer, or an isotopic form thereof, wherein the compound is represented by Formula (II)

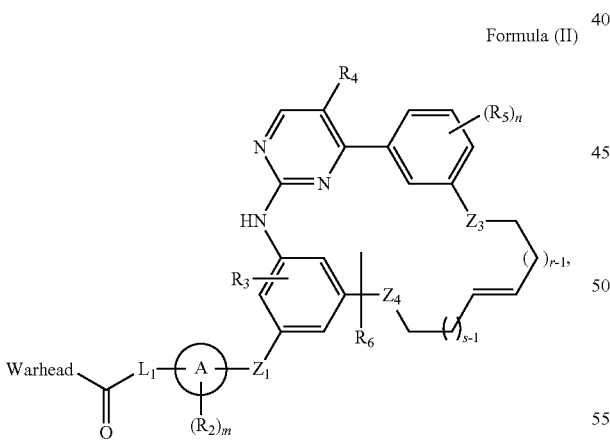

Formula (II)

in which each of Z$_1$, Z$_2$, Z$_3$, and Z$_4$ independently, is a bond, (CH$_2$)$_p$, (CH$_2$)$_p$NR$_a$(CH$_2$)$_q$, NR$_a$(CH$_2$)$_q$NR$_a$, (CH$_2$)$_p$O(CH$_2$)$_q$, CH=N, O, S, C(O), NH, S(O$_2$), OC(O), C(O)O, OSO$_2$, S(O$_2$)O, C(O)S, SC(O), C(O)C(O), C(O)NH, NHC(O), S(O$_2$)NH, NHS(O$_2$), OC(O)O, OC(O)S, OC(O)NH, OC(O)NH(CH$_2$)$_{p+1}$ NH(CH$_2$)$_q$, NHC(O)O, NHC(O)S, NHC(O)NH, (CH$_2$)$_p$NHC(O)(CH$_2$)$_q$, or (CH$_2$)$_p$C(O)NH(CH$_2$)$_q$; R$_1$ is H, alkyl, or alkyl-NR$_b$R$_c$; and each of R$_2$, R$_3$, R$_4$, R$_5$, R$_6$, and R$_7$, independently, is H, alkyl, alkenyl, alkynyl, cycloalkyl, cycloalkenyl, heterocycloalkyl, heterocycloalkenyl, halo, nitro, oxo, cyano, —OR$_a$, —SR$_a$, —NR$_b$R$_c$, —C(O)R$_a$, —SO$_2$R$_a$, —C(O)NHR$_c$, —NHC(O)R$_c$, —SO$_2$NHR$_c$, —NHSO$_2$R$_c$, -alkyl-R$_a$, -alkyl-C(O)R$_a$, -alkyl-NHR$_c$, -alkyl-C(O)NHR$_c$, -alkyl-NHC(O), or -alkyl-NHSO$_2$R$_c$.

3. The compound according to claim 2 or an N-oxide thereof, or a pharmaceutically acceptable salt, polymorph, tautomer, stereoisomer, or an isotopic form thereof, wherein the compound is represented by Formula (III)

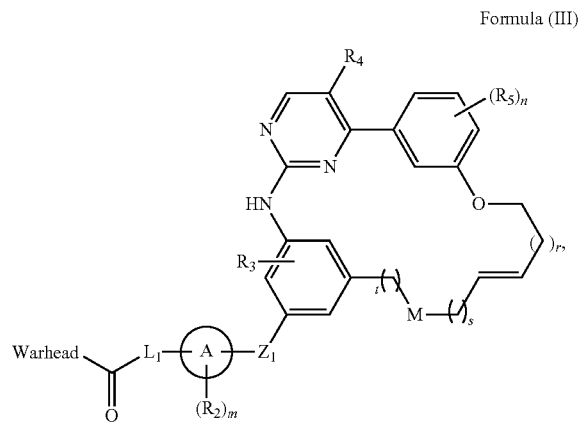

Formula (III)

in which t is 0, 1, 2, 3 or 4; R$_1$ is H, low alkyl, or low alkyl-NR$_b$R$_c$; each of R$_3$, R$_4$, and R$_5$, independently, is H, alkyl, alkenyl, alkynyl, halo, or haloalkyl; and M is (CH$_2$)$_p$, O, or N(R$_a$).

4. The compound according to claim 3 or an N-oxide thereof, or a pharmaceutically acceptable salt, polymorph, tautomer, stereoisomer, or an isotopic form thereof, wherein the compound is represented by Formula (IV)

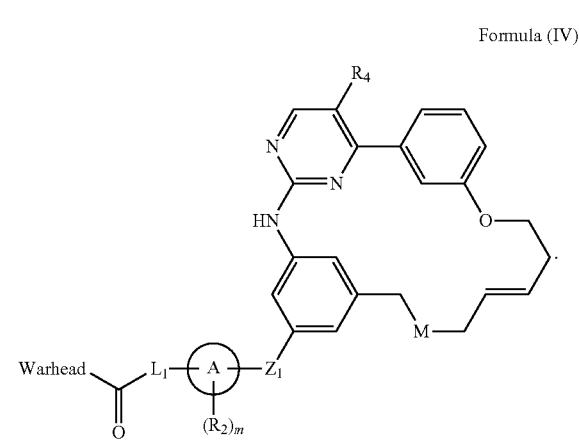

Formula (IV)

5. The compound according to claim 4 or an N-oxide thereof, or a pharmaceutically acceptable salt, polymorph, tautomer, stereoisomer, or an isotopic form thereof, wherein R$_1$ is H, —CH$_3$, or CH$_2$—N(CH$_3$)CH$_3$; R$_4$ is H, CH$_3$, CF$_3$, CN, or halo.

6. The compound according to claim 1 or an N-oxide thereof, or a pharmaceutically acceptable salt, polymorph, tautomer, stereoisomer, or an isotopic form thereof, wherein the compound is

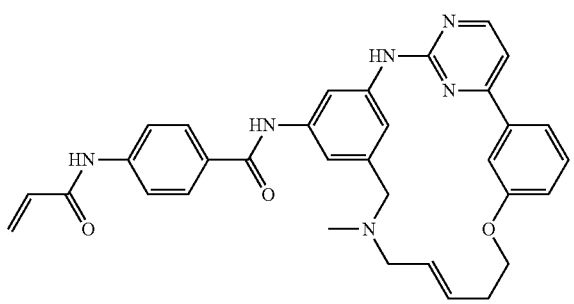
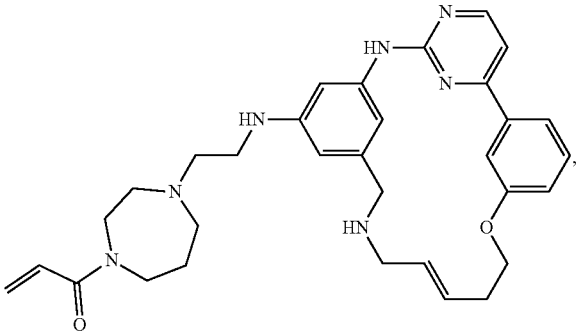
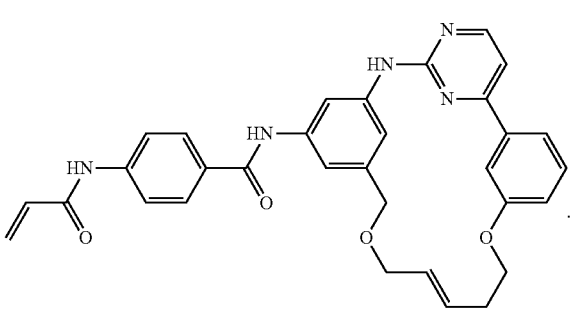
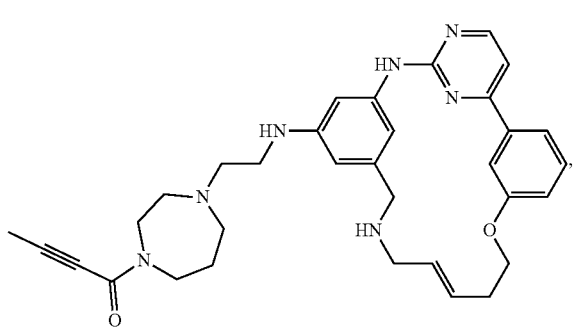
7. The compound according to claim 1 or an N-oxide thereof, or a pharmaceutically acceptable salt, polymorph, tautomer, stereoisomer, or an isotopic form thereof, wherein the compound is
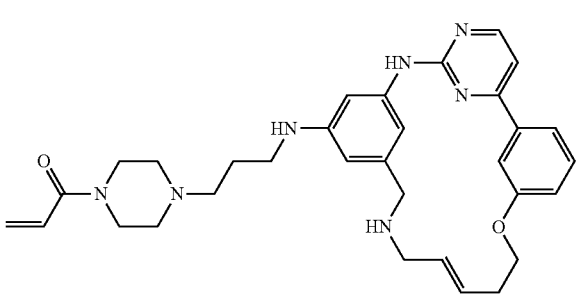
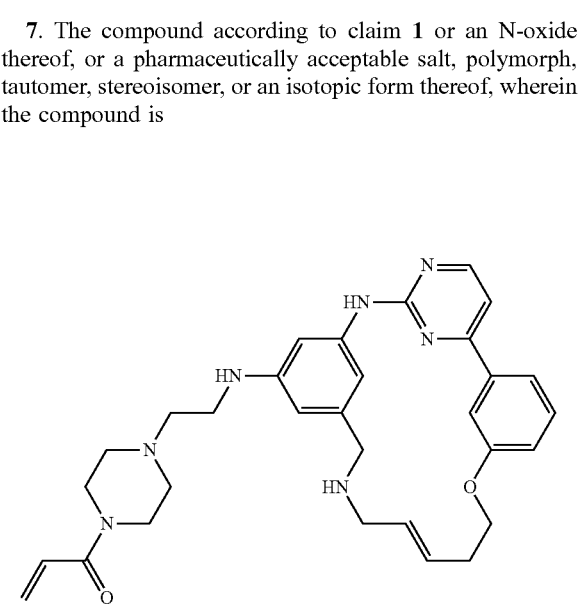
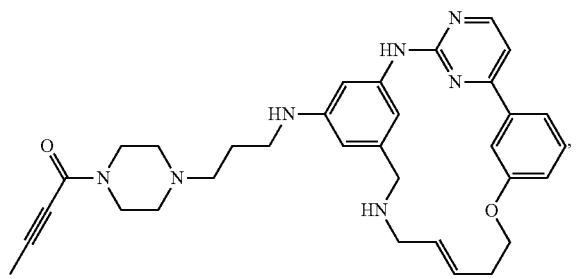
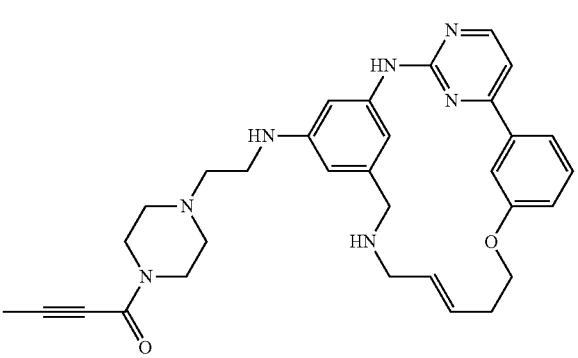
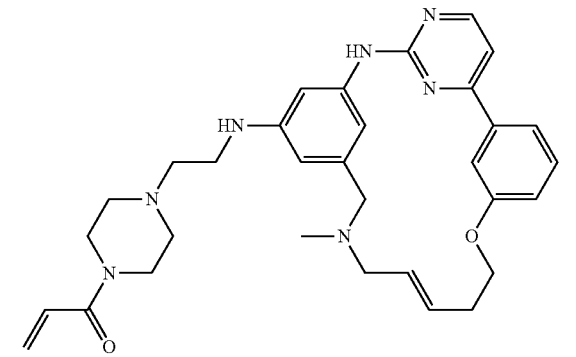

-continued
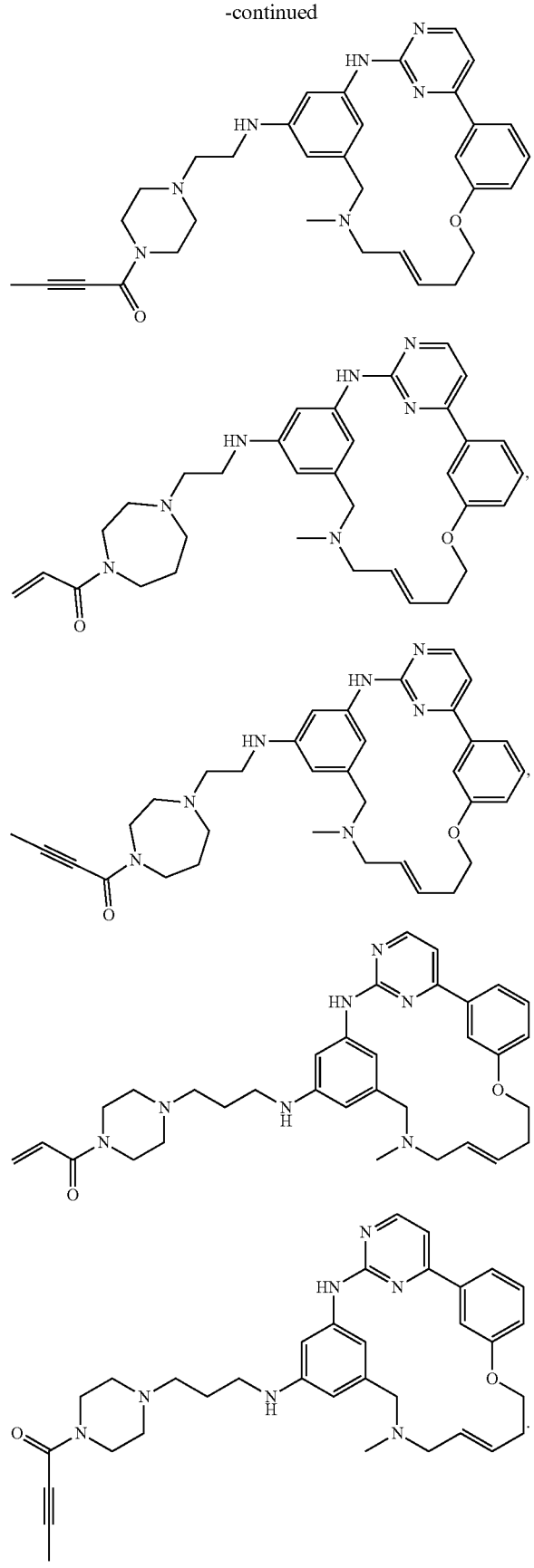
8. The compound according to claim 1 or an N-oxide thereof, or a pharmaceutically acceptable salt, polymorph, tautomer, stereoisomer, or an isotopic form thereof, wherein the compound is
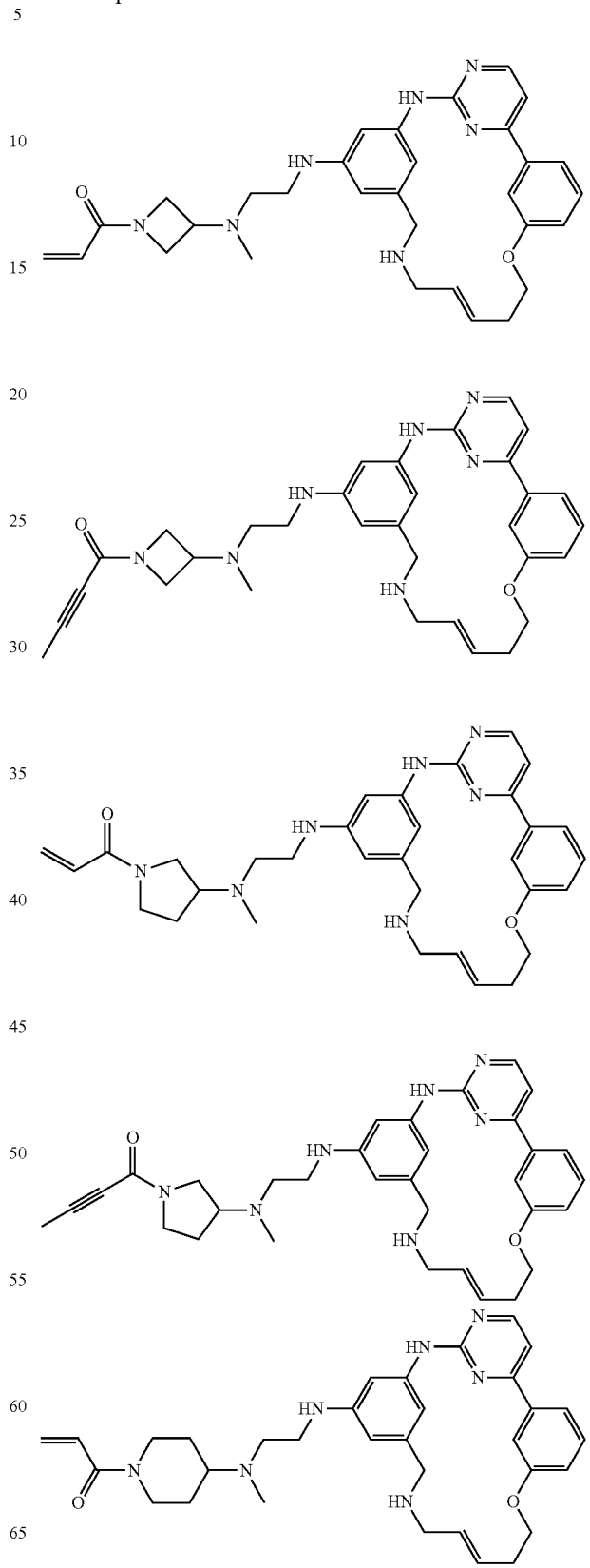

117
-continued

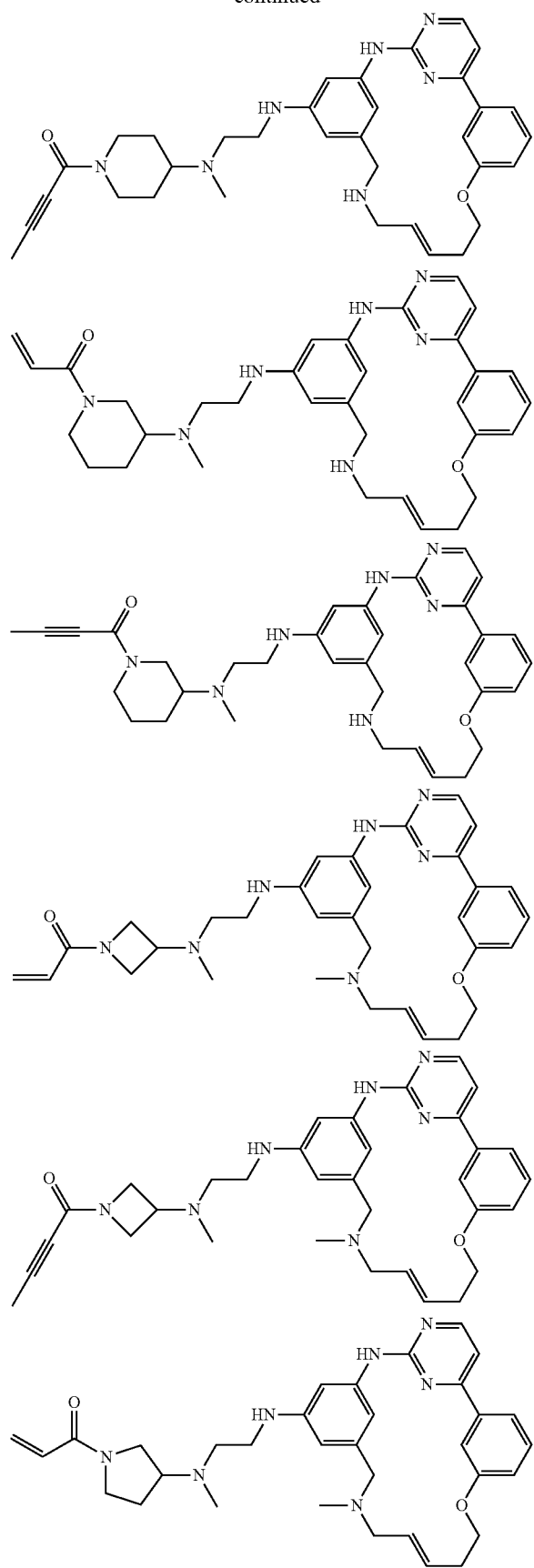

118
-continued

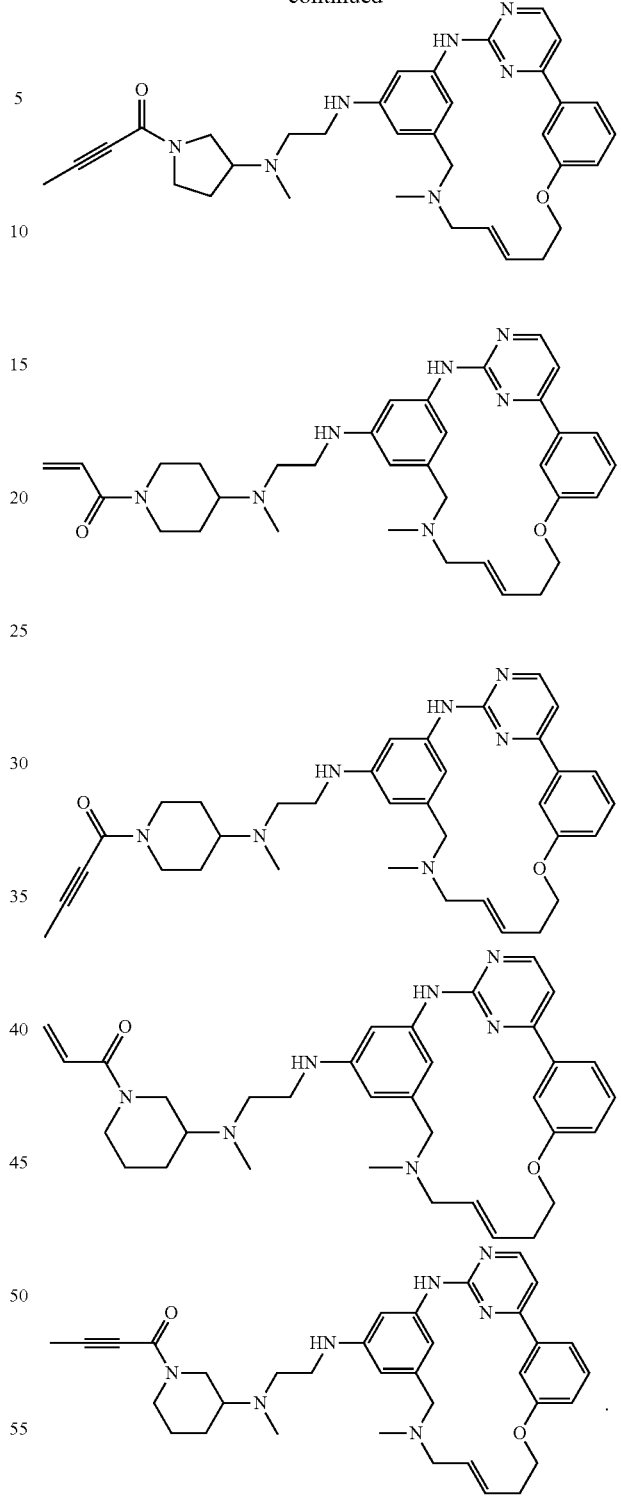

9. A pharmaceutical composition comprising a compound of Formula (I) or an N-oxide thereof as defined in claim 1, or a pharmaceutically acceptable salt, polymorph, tautomer, stereoisomer, or an isotopic form thereof, and a pharmaceutically acceptable diluent or carrier.

10. A compound or an N-oxide thereof, or a pharmaceutically acceptable salt, polymorph, tautomer, stereoisomer, or an isotopic form thereof, wherein the compound is

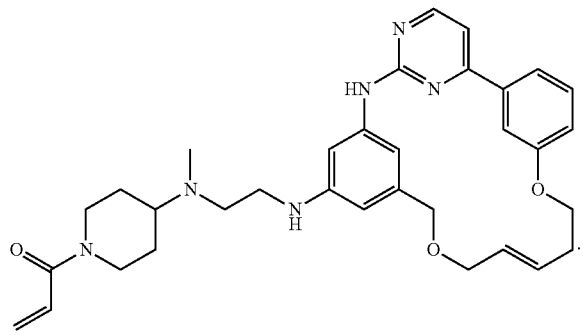 [SMILES: C=CC(=O)N1CCC(N(C)CCNc2cc3cc(c2)Nc2nccc(n2)-c2cccc(c2)OCC/C=C/COC3)CC1]

11. A compound, wherein the compound is

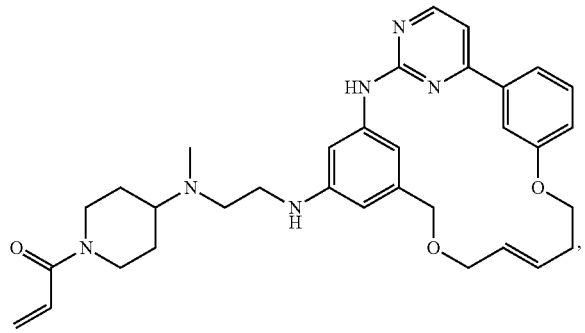 [SMILES: C=CC(=O)N1CCC(N(C)CCNc2cc3cc(c2)Nc2nccc(n2)-c2cccc(c2)OCC/C=C/COC3)CC1]

or a pharmaceutically acceptable salt thereof.

12. A pharmaceutical composition comprising a compound of claim 11 or a pharmaceutically acceptable salt thereof, and a pharmaceutically acceptable diluent or carrier.

13. The compound according to claim 2 or an N-oxide thereof, or a pharmaceutically acceptable salt thereof, wherein the compound is represented by Formula (III)

Formula (III)

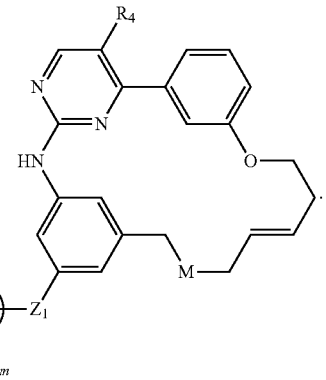

in which t is 0, 1, 2, 3 or 4; $R_1$ is H, low alkyl, or low alkyl-$NR_bR_c$; each of $R_3$, $R_4$, and $R_5$, independently, is H, alkyl, alkenyl, alkynyl, halo, or haloalkyl; and M is O or $N(R_a)$.

14. The compound according to claim 3 or an N-oxide thereof, or a pharmaceutically acceptable salt thereof, wherein the compound is represented by Formula (IV)

Formula (IV)

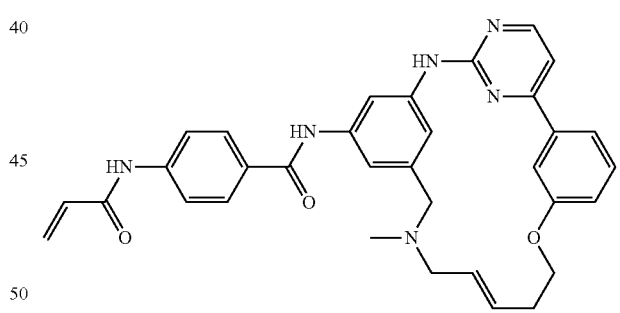

15. The compound according to claim 4 or an N-oxide thereof, or a pharmaceutically acceptable salt thereof, wherein $R_1$ is H, —$CH_3$, or $CH_2$—$N(CH_3)CH_3$; $R_4$ is H, $CH_3$, $CF_3$, CN, or halo.

16. The compound according to claim 1 or a pharmaceutically acceptable salt thereof, wherein the compound is

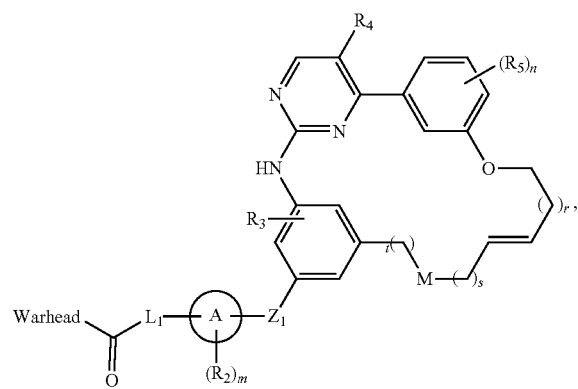

17. The compound according to claim 1 or a pharmaceutically acceptable salt thereof, wherein the compound is

121
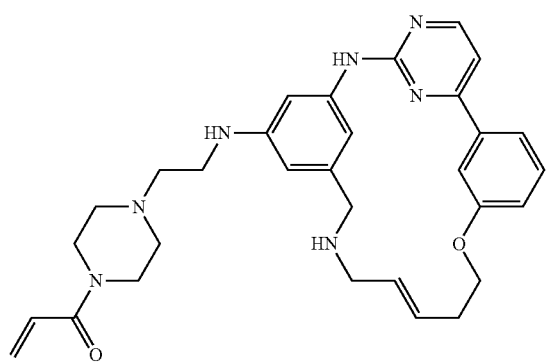
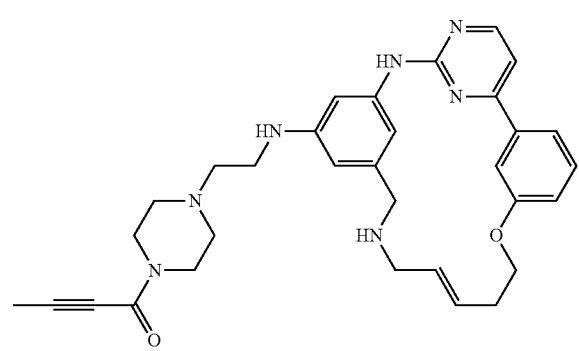
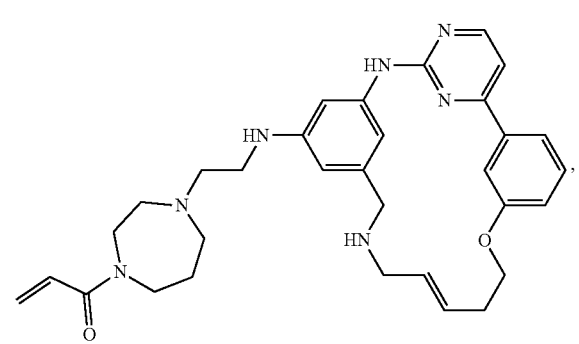
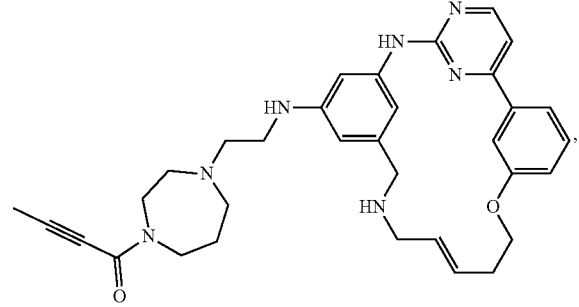
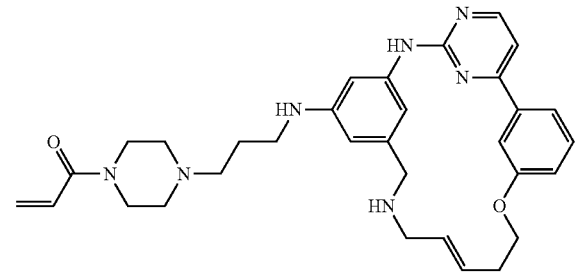
122
-continued
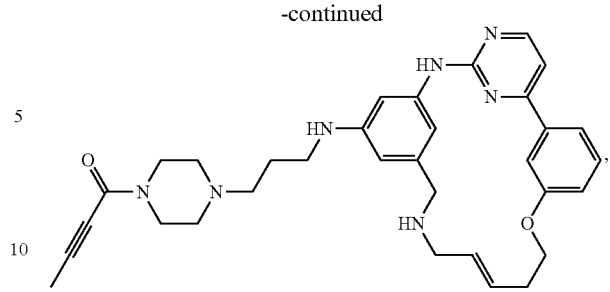
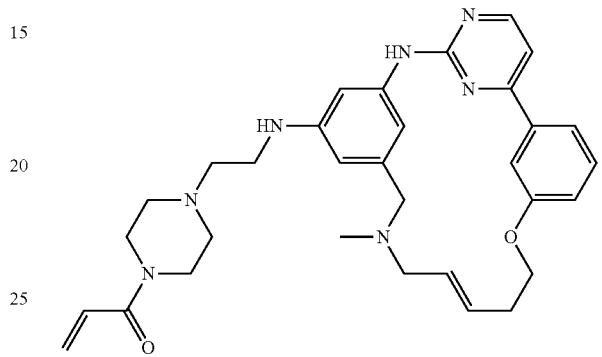
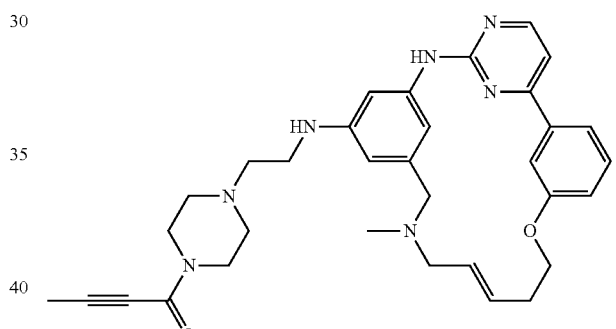
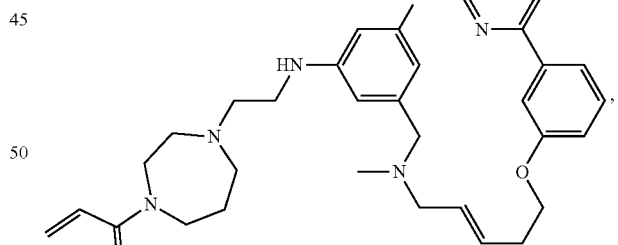
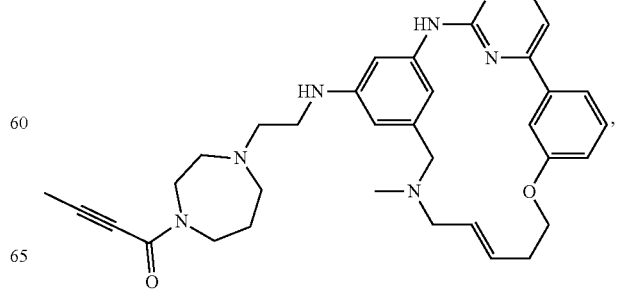

123
-continued
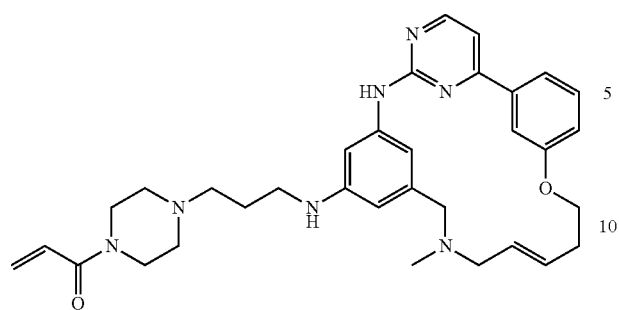
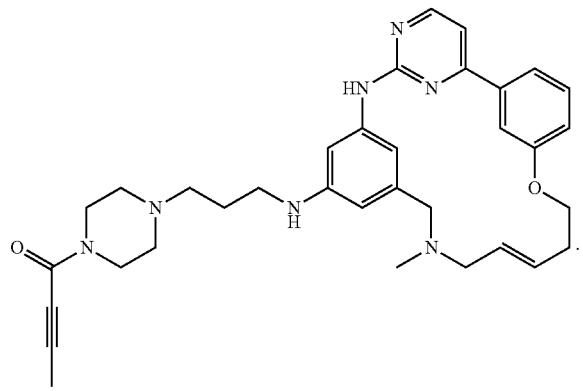
18. The compound according to claim 1 or a pharmaceutically acceptable salt thereof, wherein the compound is
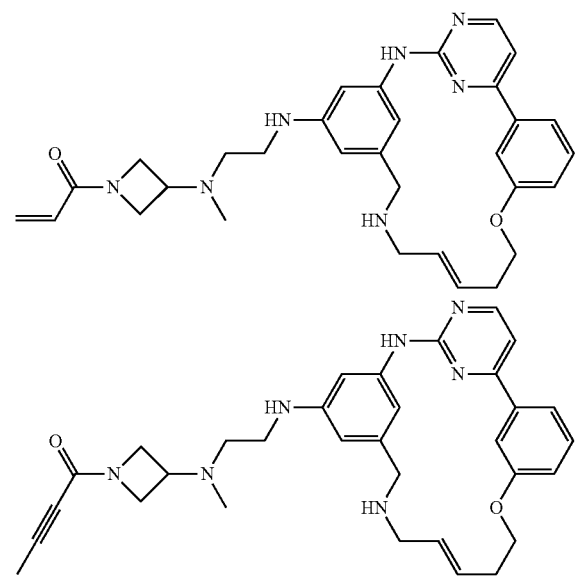
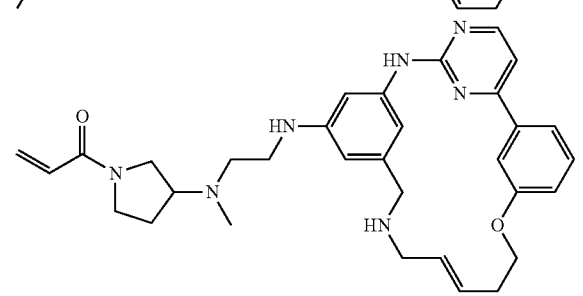
124
-continued
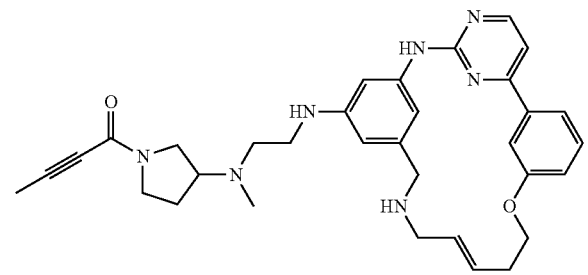
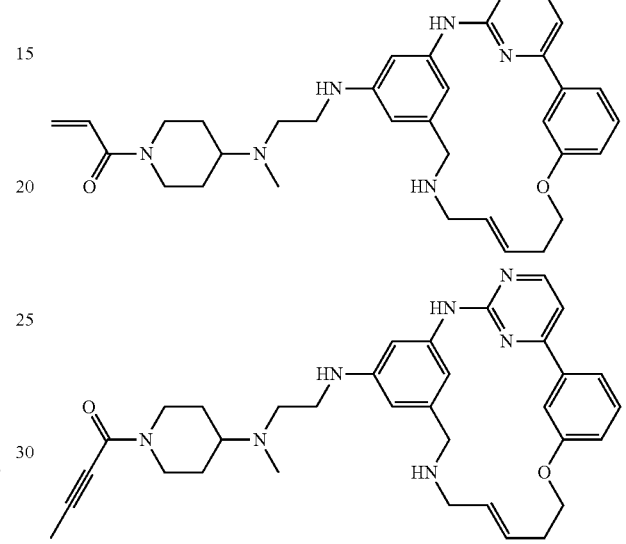
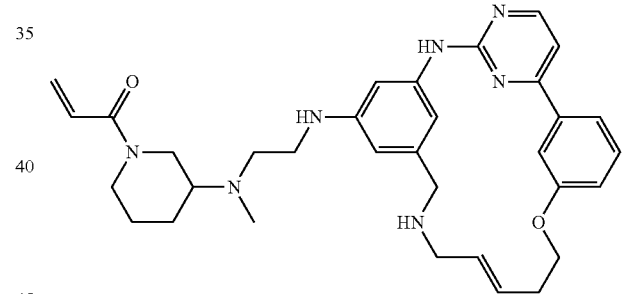
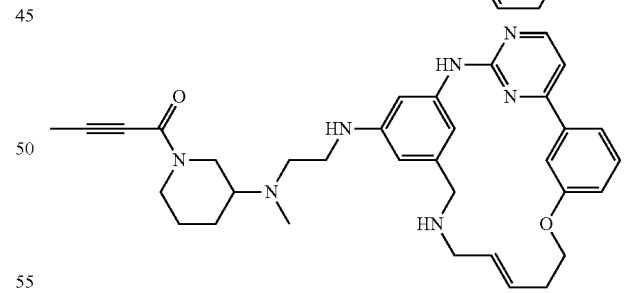
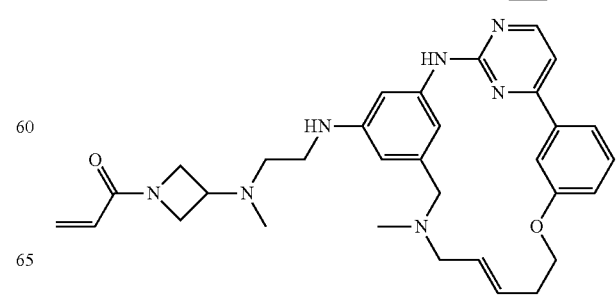

125
-continued
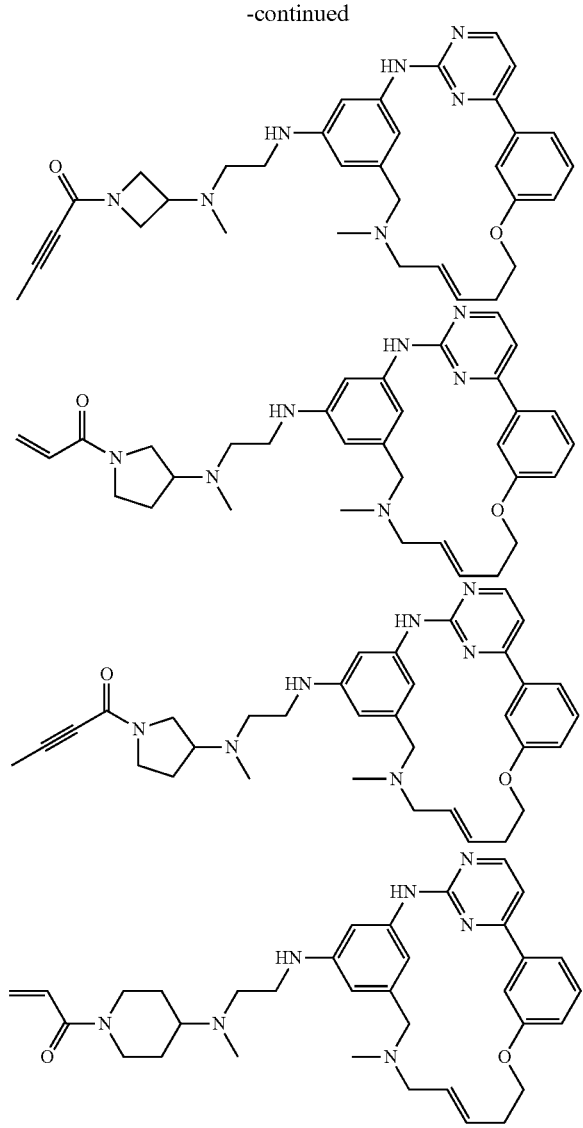
126
-continued
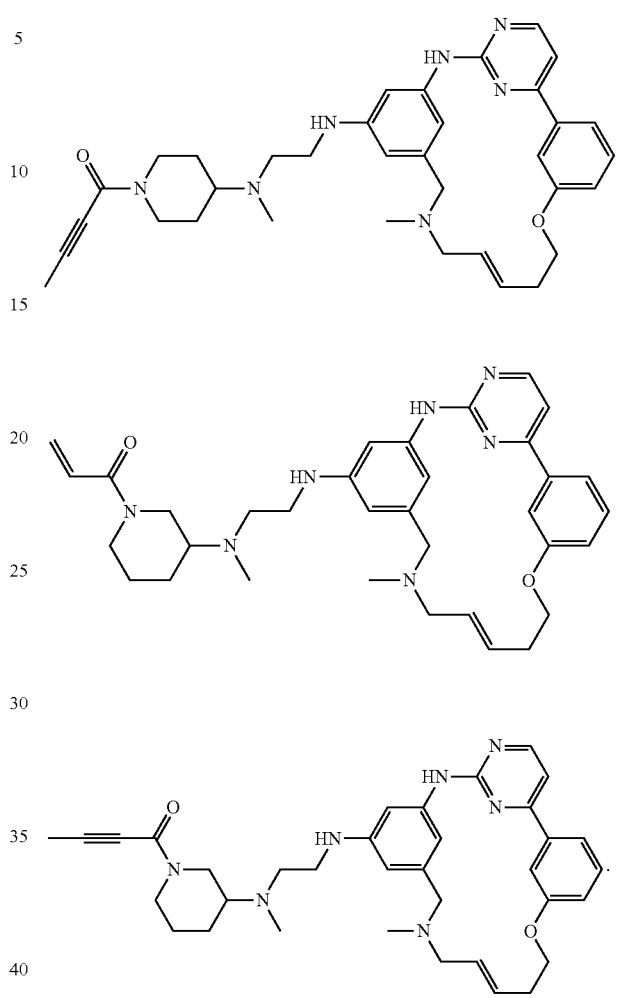
* * * * *